United States Patent
Png et al.

(10) Patent No.: US 11,945,865 B2
(45) Date of Patent: *Apr. 2, 2024

(54) BLOCKADE OF CD7 EXPRESSION AND CHIMERIC ANTIGEN RECEPTORS FOR IMMUNOTHERAPY OF T-CELL MALIGNANCIES

(71) Applicant: National University of Singapore, Singapore (SG)

(72) Inventors: Yi Tian Png, Singapore (SG); Natasha Vinanica, Singapore (SG); Takahiro Kamiya, Tokyo (JP); Dario Campana, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,292

(22) Filed: Jul. 14, 2022

(65) Prior Publication Data
US 2022/0348655 A1  Nov. 3, 2022

Related U.S. Application Data

(63) Continuation of application No. 15/821,153, filed on Nov. 22, 2017, now Pat. No. 11,440,958.

(60) Provisional application No. 62/425,398, filed on Nov. 22, 2016, provisional application No. 62/543,696, filed on Aug. 10, 2017.

(51) Int. Cl.
| | | |
|---|---|---|
| *A61K 38/00* | (2006.01) | |
| *A61K 35/17* | (2015.01) | |
| *A61K 39/00* | (2006.01) | |
| *A61P 35/02* | (2006.01) | |
| *C07K 14/705* | (2006.01) | |
| *C07K 14/725* | (2006.01) | |
| *C07K 16/28* | (2006.01) | |
| *C07K 16/30* | (2006.01) | |

(52) U.S. Cl.
CPC .......... *C07K 16/2803* (2013.01); *A61K 35/17* (2013.01); *A61K 39/001129* (2018.08); *A61P 35/02* (2018.01); *C07K 14/7051* (2013.01); *C07K 14/70517* (2013.01); *C07K 14/70578* (2013.01); *C07K 16/3061* (2013.01); *A61K 38/00* (2013.01); *A61K 2039/5156* (2013.01); *A61K 2039/5158* (2013.01); *A61K 2039/804* (2018.08); *C07K 2317/56* (2013.01); *C07K 2317/622* (2013.01); *C07K 2317/76* (2013.01); *C07K 2319/02* (2013.01); *C07K 2319/03* (2013.01); *C07K 2319/04* (2013.01); *C07K 2319/05* (2013.01); *C07K 2319/33* (2013.01); *C07K 2319/74* (2013.01)

(58) Field of Classification Search
None
See application file for complete search history.

(56) References Cited

U.S. PATENT DOCUMENTS

| | | |
|---|---|---|
| 6,326,193 B1 | 12/2001 | Liu et al. |
| 7,887,805 B2 | 2/2011 | Pedersen et al. |
| 8,580,714 B2 | 11/2013 | Almagro et al. |
| 8,614,307 B2 | 12/2013 | Moretta et al. |
| 8,697,359 B1 | 4/2014 | Zhang |
| 9,683,042 B2 | 6/2017 | Lee et al. |
| 10,273,280 B2 | 4/2019 | Ma et al. |
| 10,550,183 B2 | 2/2020 | Png et al. |
| 10,765,699 B2 | 9/2020 | Campana et al. |
| 11,440,958 B2 | 9/2022 | Png et al. |
| 11,648,269 B2 | 5/2023 | Campana et al. |
| 11,679,132 B2 | 6/2023 | Campana et al. |
| 2003/0105000 A1 | 6/2003 | Pero et al. |
| 2006/0034834 A1 | 2/2006 | Marasco et al. |
| 2007/0036773 A1 | 2/2007 | Cooper et al. |
| 2012/0282256 A1 | 11/2012 | Campana et al. |
| 2013/0266551 A1 | 10/2013 | Campana et al. |
| 2013/0287748 A1 | 10/2013 | June et al. |
| 2014/0068797 A1 | 3/2014 | Doudna et al. |
| 2014/0120622 A1 | 5/2014 | Gregory et al. |
| 2014/0186387 A1 | 7/2014 | Lauer et al. |
| 2016/0060341 A1* | 3/2016 | Lee ................ A61K 47/6849 435/320.1 |
| 2016/0256488 A1 | 9/2016 | Wu |
| 2016/0272999 A1 | 9/2016 | Duchateau et al. |
| 2016/0312182 A1 | 10/2016 | Sentman |
| 2017/0119820 A1 | 5/2017 | Moriarity et al. |
| 2017/0204372 A1 | 7/2017 | Mohler et al. |
| 2018/0086831 A1 | 3/2018 | Pule et al. |

(Continued)

FOREIGN PATENT DOCUMENTS

| | | |
|---|---|---|
| CA | 2937157 A1 | 1/2018 |
| CN | 103492406 A | 1/2014 |

(Continued)

OTHER PUBLICATIONS

Wheeler et al., Intrabody and Intrakine Strategies for Molecular Therapy 1\,IoLECGLAR Therapy vol. 8, No. 3, Sep. 2003; pp. 355-366.*
Arafat et al., Antineoplastic effect of anti-erbB-2 intrabody is not correlated with scFv affinity for its target Cancer Gene Therapy, vol. 7, No. 9, 2000: pp. 1250-1256.*
Png et al., Blockade ofCD7 expression in T cells fix efective chimeric antigen receptor targeting of T-cell malignancies Blood Adv. 2017;1(25):2348-2360.*
U.S. Appl. No. 15/548,577 Applicants' arguments made in Mar. 17, 2020 , pp. 6-12.*

(Continued)

*Primary Examiner* — Maria G Leavitt
(74) *Attorney, Agent, or Firm* — Wilson Sonsini Goodrich & Rosati

(57) ABSTRACT

The present invention provides compositions comprising an anti-CD7 chimeric activating receptor (CAR) and an anti-CD7 protein expression blocker, and methods of using such compositions in cancer therapy.

15 Claims, 25 Drawing Sheets

Specification includes a Sequence Listing.

(56) References Cited

U.S. PATENT DOCUMENTS

| | | |
|---|---|---|
| 2018/0179280 A1 | 6/2018 | Png et al. |
| 2018/0371052 A1 | 12/2018 | Ma et al. |
| 2019/0038733 A1 | 2/2019 | Campana et al. |
| 2021/0046112 A1* | 2/2021 | Campana ............... A61P 37/02 |
| 2021/0395779 A1 | 12/2021 | Ismail et al. |

FOREIGN PATENT DOCUMENTS

| | | |
|---|---|---|
| CN | 107709548 A | 2/2018 |
| JP | H03219896 A | 9/1991 |
| JP | H09501824 A | 2/1997 |
| JP | 2001516766 A | 10/2001 |
| JP | 2008506368 A | 3/2008 |
| JP | 2008518021 A | 5/2008 |
| JP | 2009511495 A | 3/2009 |
| JP | 2010537671 A | 12/2010 |
| JP | 2011510047 A | 3/2011 |
| JP | 2014507118 A | 3/2014 |
| JP | 2016508728 A | 3/2016 |
| JP | 2020530291 A | 10/2020 |
| JP | 6895380 B2 | 6/2021 |
| WO | WO-9914353 A2 | 3/1999 |
| WO | WO-0129058 A1 | 4/2001 |
| WO | WO-0196584 A2 | 12/2001 |
| WO | WO 03/051926 A2 * | 6/2003 |
| WO | WO-03051926 A2 | 6/2003 |
| WO | WO-2005017163 A2 | 2/2005 |
| WO | WO-2012079000 A1 | 6/2012 |
| WO | WO-2013126712 A1 | 8/2013 |
| WO | WO-2014098319 A1 | 6/2014 |
| WO | WO-2014124143 A1 | 8/2014 |
| WO | WO 2014/0938319 * | 10/2014 |
| WO | WO-2015075468 A1 | 5/2015 |
| WO | WO-2015121454 A1 | 8/2015 |
| WO | WO-2015150771 A1 | 10/2015 |
| WO | WO-2016055551 A1 | 4/2016 |
| WO | WO-2016102965 A1 | 6/2016 |
| WO | WO-2016126213 A1 | 8/2016 |
| WO | WO-2016138491 A1 | 9/2016 |
| WO | WO-2017149515 A1 | 9/2017 |
| WO | WO-2017213979 A1 | 12/2017 |
| WO | WO-2018027036 A1 | 2/2018 |
| WO | WO-2018098306 A1 | 5/2018 |
| WO | WO-2020102589 A1 | 5/2020 |

OTHER PUBLICATIONS

Aandahl et al., CD7 is a differentiation marker that identifies multiple CD8 T cell effector subsets, J Immunol 2003; 170:2349-2355.

Altschul et al. Basic local alignment search tool. J Mol Biol 215(3):403-410 (1990).

Appelbaum. Haematopoietic cell transplantation as immunotherapy. Nature, vol. 411, pp. 385-389 (2001).

Applicants' arguments for U.S. Appl. No. 15/821,170, pp. 6-10; filed Jun. 27, 2019.

Böldicke et al., Blocking translocation of cell surface molecules from the ER to the cell surface by intracellular antibodies targeted to the ER, J. Cell. Mol. Med., 11(1):54-70 (2007).

Boettcher et al, Choosing the Right Tool for the Job: RNAi, TALEN, or CRISPR, Mol Cell. May 21, 2015;58:575-85.

Bonilla et al., Targeted gene disruption of murine CD7, Int Immunol. Dec. 1997;9(12):1875-83.

Brentjens et al. Eradication of systemic B-cell tumors by genetically targeted human T lymphocytes co-stimulated by CD80 and interleukin-15. Nat Med. Mar. 2003;9(3):279-86.

Brentjens et al., "Genetically Targeted T Cells Eradicate Systemic Acute Lymphoblastic Leukemia Xenografts," Clin Cancer Res I 3(18):5426-5435, Sep. 15, 2007.

Burgess et al. Possible dissociation of the heparin-binding and mitogenic activities of heparin-binding (acidic fibroblast) growth factor-1 from its receptor-binding activities by site-directed mutagenesis of a single lysine residue. J Cell Biol. 111:2129-2138 (1990).

Campana et al. 4-1BB chimeric antigen receptors. Cancer J. Mar.-Apr. 2014;20(2):134-40.

Campana et al., Minimal residual disease-guided therapy in childhood acute lymphoblastic leukemia. Blood. Apr. 6, 2017;129(14):1913-1918, Epub Feb. 6, 2017.

Chang et al. A chimeric receptor with NKG2D specificity enhances natural killer cell activation and killing of tumor cells. Cancer Res 73(6):1777-86 (Mar. 15, 2013). Published online Jan. 9, 2013.

Clift, Dean, et al "A Method for the Acute and Rapid Degradation of Endogenous Proteins", Elsevier Inc., Cell 172, Dec. 14, 2017, pp. 1692-1706.

Colman, P.M., "Effects of amino acid sequence changes on antibody-antigen interactions", Res. Immunology, Jan. 1994, vol. 145, pp. 33-36.

Cooley et al. Donor selection for natural killer cell receptor genes leads to superior survival after unrelated transplantation for acute myelogenous leukemia. Blood (2010) 116 (14): 2411-2419.

Cooper, et al. T-cell clones can be rendered specific for CD19: toward the selective augmentation of the graft-versus-B-lineage leukemia effect. Blood. Feb. 15, 2003;101(4):1637-44. Epub Oct. 10, 2002.

Coustan-Smith et al., Use of peripheral blood instead of bone marrow to monitor residual disease in children with acute lymphoblastic leukemia, Blood. Oct. 1, 2002;100(7):2399-402. Prepublished online May 31, 2002.

Coustan-Smith et al., Early T-cell precursor leukemia: a subtype of very high-risk acute lymphoblastic leukemia, Lancet Oncol. Feb. 2009 ; 10(2): 147-156.

Davila. Efficacy and toxicity management of 19-28z CAR T cell therapy in B cell acute lymphoblastic leukemia. Sci Transl Med 6(224):224ra25 (2014).

Dotti et al. Design and development of therapies using chimeric antigen receptor-expressing T cells. Immunological Reviews, vol. 257, Issue 1, pp. 107-126 (2014).

EP17874643.4 Extended European Search Report dated Jun. 3, 2020.

Eshhar et al. Specific activation and targeting of cytotoxic lymphocytes through chimeric single chains consisting of antibody-binding domains and the gamma or zeta subunits of the immunoglobulin and T-cell receptors. Proc Natl Acad Sci U S A, vol. 90, pp. 720-724 (Jan. 1993).

Final office action for U.S. Appl. No. 15/821,170, pp. 1-11, filed Sep. 27, 2018.

Frankel et al., Therapy of patients with T-cell lymphomas and leukemias using an anti-CD7 monoclonal antibody-ricin A chain immunotoxin, Leukemia & Lymphoma, vol. 26, pp. 287-298 (1997).

Gao et al. Retention mechanisms for ER and Golgi membrane proteins. Trends in Plant Science, vol. 19, Issue 8, pp. 508-515 (Aug. 2014).

Geiger et al. Integrated src kinase and costimulatory activity enhances signal transduction through single-chain chimeric receptors in T lymphocytes. Blood 98(8):2364-2371 (2001).

Geiger et al. The TCR zeta-chain immunoreceptor tyrosine-based activation motifs are sufficient for the activation and differentiation of primary T lymphocytes. The Journal of Immunology, 1999, 162: 5931-5939.

Giebel et al. Survival advantage with KIR ligand incompatibility in hematopoietic stem cell transplantation from unrelated donors. Blood (2003) 102 (3): 814-819.

Gomes-Silva et al., CD7-edited T cells expressing a CD7-specific CAR for the therapy of T-cell malignancies, Blood. 2017;130(3):285-296. Prepublished online May 24, 2017.

Grimshaw et al. Creating a Null T Cell for Adoptive Immunotherapy. Poster. Mar. 9, 2012. One page.

Grupp et al. Chimeric antigen receptor-modified T cells for acute lymphoid leukemia. NEJM 368:1509-1518 (2013).

Grupp et al. Chimeric Antigen Receptor-Modified T Cells for Acute Lymphoid Leukemia. N Engl J Med 368;16, pp. 1509-1508 (Apr. 18, 2013). With correction published N. Engl J. Med (2016) 374(10) 998.

(56) References Cited

OTHER PUBLICATIONS

Haso et al. Anti-CD22-chimeric antigen receptors targeting B-cell precursor acute lymphoblastic leukemia. Blood. 2013;121(7):1165-1174. Prepublished online Dec. 14, 2012.
Haynes et al., Human lymphocyte antigens: production of a monoclonal antibody that defines functional thymus-derived lymphocyte subsets. Proc Natl Acad Sci USA Nov. 1979; 76(11):5829-5833.
Haynes et al. Single-chain antigen recognition receptors that costimulate potent rejection of established experimental tumors. Blood. Nov. 1, 2002;100(9):3155-63. Published online Jul. 5, 2002.
Hegde, M. et al., "Combinational targeting offsets antigen escape and enhances effector functions of adoptively transferred T cells in glioblastoma", Molecular Therapy, 2013, vol. 21, pp. 2087-2101.
Hegde, M. et al., Supplementary Material for "Combinational targeting offsets antigen escape and enhances effector functions of adoptively transferred T cells in glioblastoma", Molecular Therapy, 2013, vol. 21, pp. 2087-2101. Retrieved Jan. 6, 2022 from URL: https://ars.els-cdn.com/content/image/1-s2.0-S1525001616309315-mmc1.pdf. 9 pages.
Henikoff, et al. Amino acid substitution matrices from protein blocks. Proc Natl Acad Sci U S A. Nov. 15, 1992;89(22):10915-9.
Holliger et al. "Diabodies": small bivalent and bispecific antibody fragments. Proc Natl Acad Sci USA, vol. 90, pp. 6444-6448 (Jul. 1993).
Hombach et al. Tumor-Specific T Cell Activation by Recombinant Immunoreceptors: CD3ζ Signaling and CD28 Costimulation are Simultaneously Required for Efficient IL-2 Secretion and Can be Integrated Into One Combined CD28/CD3ζ Signaling Receptor Molecule. J Immunol 2001; 167:6123-6131.
Ibragimova. Stability of the β-Sheet of the WW Domain: A Molecular Dynamics Simulation Study. Biophysical Journal, vol. 77, pp. 2191-2198 (Oct. 1999).
Imai et al. Chimeric receptors with 4-1BB signaling capacity provoke potent cytotoxicity against acute lymphoblastic leukemia. Leukemia (2004) 18, 676-684.
Imai et al. Genetic modification of primary natural killer cells overcomes inhibitory signals and induces specific killing of leukemic cells. Blood (2005) 106 (1): 376-383.
Imamura. M. et al., "Autonomous growth and increased cytotoxicity of natural killer cells expressing membrane-bound interleukin-15", Blood, 2014, vol. 124, pp. 1081-1088.
Inukai et al., Clinical significance of early T-cell precursor acute lymphoblastic leukaemia: results of the Tokyo Children's Cancer Study Group Study L99-15, British Journal of Haematology, 156, 358-365 (2011). First published online Nov. 30, 2011.
Jabbour et al., New insights into the pathophysiology and therapy of adult acute lymphoblastic leukemia, Cancer 2015;121:2517-28. Published online Apr. 17, 2015.
Jackson et al., Identification of a consensus motif for retention of transmembrane proteins in the endoplasmic reticulum, EMBO J. Oct. 1990; 9(10): 3153-3162.
Jain et al., Early T-cell precursor acute lymphoblastic leukemia/lymphoma (ETP-ALL/LBL) in adolescents and adults: a high-risk subtype, Blood. 2016;127(15):1863-1869. Prepublished online Jan. 18, 2016.
Kalos, et al., "T Cells with Chimeric Antigen Receptors Have Potent Antitumor Effects and Can Establish Memory in Patients with Advanced Leukemia", Science Translation Medicine 3.95 (2011):95ra73-95ra73.
Kamiya, et al., "A novel method to generate T-cell receptor-deficient antigen receptor T cells," Blood Advances, vol. 2, No. 5, Mar. 13, 2018, pp. 517-528.
Kim et al. High cleavage efficiency of a 2A peptide derived from porcine teschovirus-1 in human cell lines, zebrafish and mice. PLoS One 6:e18556 (2011).
Kita et al., Clinical importance of CD7 expression in acute myelocytic leukemia. The Japan Cooperative Group of Leukemia/Lymphoma, Blood, May 1, 1993;81(9):2399-405.
Kloss, C.C. et al., "Combinatorial antigen recognition with balanced signaling promotes selective tumor eradication by engineered T cells", Nature Biotechnology, 2013, vol. 31, pp. 71-75.
Kloss, C.C. et al., Supplementary Text and Figures for "Combinatorial antigen recognition with balanced signaling promotes selective tumor eradication by engineered T cells", Nature Biotechnology, 2013, vol. 31, pp. 71-75. Retrieved Jan. 6, 2021 at URL: https://static-content.springer.com/esm/art%3A10.1038%2Fnbt.2459/MediaObjects/41587_2013_BFnbt2459_MOESM2_ESM.pdf. 5 pages.
Kolb et al. Graft-versus-leukemia effect of donor lymphocyte transfusions in marrow grafted patients. Blood, vol. 86. No. 5 Sep. 1, 1995: pp. 2041-2050.
Kudo et al. T lymphocytes expressing a CD16 signaling receptor exert antibody-dependent cancer cell killing. Cancer Res 74(1):93-103 (2013).
Lanitis et al. Chimeric antigen receptor T Cells with dissociated signaling domains exhibit focused anti-tumor activity with reduced potential for toxicity in vivo. Cancer Immunol Res 1(1):43-53 (2013).
Lee et al., Immunologic Characterization of CD7-Deficient Mice, J Immunol 1998; 160:5749-5756.
Lee et al. T cells expressing CD19 chimeric antigen receptors for acute lymphoblastic leukaemia in children and young adults: A phase 1 dose-escalation trial. The Lancet 385(9967):517-528 (2014).
Leung et al., Detectable minimal residual disease before hematopoietic cell transplantation is prognostic but does not preclude cure for children with very-high-risk leukemia, Blood. 2012;120(2):468-472. Prepublished online Apr. 19, 2012.
Lo, A.S.Y. et al., "Harnessing the tumour-derived cytokine, CSF-1, to co-stimulate Tcell growth and activation", Molecular Immunology, 2008, vol. 45, pp. 1276-1287.
Long et al., 4-1BB costimulation ameliorates T cell exhaustion induced by tonic signaling of chimeric antigen receptors, Nature Medicine, Jun. 2015; 21(6):581-90. Epub May 4, 2015.
Maciocia et al. A simple protein-based method for generation of 'off the shelf' allogeneic chimeric antigen receptor T-cells. Database EMBase [Online] 1-15, Elsevier Science Publishers, Amsterdam, NL (May 1, 2018). Abstract. XP002784541. Database Accession No. EMB-623339718.
Maciocia et al. A simple protein-based method for generation of 'off the shelf' allogeneic chimeric antigen receptor T-cells. Molecular Therapy, vol. 26, No. 5, Supplement 1, pp. 296-297 (May 2018). Cell Press NLD. May 16, 2018 to May 19, 2018 Chicago, IL-297 CONF. ISSN: 1525-0024.
Maetzig et al.: Gammaretroviral vectors: biology, technology and application. Viruses 3(6):677-713 doi:10.3390/v3060677 (2011).
Maher et al. Human T-lymphocyte cytotoxicity and proliferation directed by a single chimeric TCRzeta /CD28 receptor. Nat Biotech 20(1):70-75 (2002).
Mamonkin et al., A T-cell-directed chimeric antigen receptor for the selective treatment of T-cell malignancies, Blood. 2015;126(8):983-992. Prepublished online Jun. 8, 2015.
Manabe et al., Interleukin-4 induces programmed cell death (apoptosis) in cases of high-risk acute lymphoblastic leukemia. Blood. Apr. 1, 1994; 83(7):1731-7.
Marks et al., Management of adults with T-cell lymphoblastic leukemia, Blood. Mar. 2, 2017;129(9):1134-1142, Epub Jan. 23, 2017.
Marschall, Andrea LJ, et al "Specific in vivo knockdown of protein function by intrabodies", Taylor & Francis Group, LLC, Nov./Dec. 2015, vol. 7, Issue 6, pp. 1010-1035.
Maude, et al., Chimeric Antigen Receptor T Cells for Sustained Remissions in Leukemia. N. Engl J. Med (2014) 371(16) 1507-1517. With correction published N. Engl J. Med 374(10):998 (2016).
Mihara et al, Activated T-cell-mediated immunotherapy with a chimeric receptor against CD38 in B-cell non-Hodgkin lymphoma, J Immunother. Sep. 2009; 32(7):737-43.
Miller et al. Successful adoptive transfer and in vivo expansion of human haploidentical NK cells in patients with cancer. Blood 105:3051-3057 (2005).

(56) References Cited

OTHER PUBLICATIONS

Milone et al. Chimeric receptors containing CD137 signal transduction domains mediate enhanced survival of T cells and increased antileukemic efficacy in vivo. Mol. Ther. 17:1453-1464 (2009).
Munro et al., A C-terminal signal prevents secretion of luminal ER proteins, Cell. Mar. 13, 1987;48:899-907. Retrieved Apr. 7, 2022 at URL: https://bio.davidson.edu/molecular/MunPelham/mufixed.html.
Needleman et al. A general method applicable to the search for similarities in the amino acid sequence of two proteins. Journal of molecular biology 48(3):443-453 (1970).
Neumann et al., Clinical and molecular characterization of early T-cell precursor leukemia: a high-risk subgroup in adult T-ALL with a high frequency of FLT3 mutations, Blood Cancer Journal 2, e55, Jan. 27, 2012. 7 pages.
Non final office action for U.S. Appl. No. 15/821,170, pp. 1-10, filed Mar. 27, 2019.
Non final office action for U.S. Appl. No. 15/821,170, pp. 1-12, filed Apr. 5, 2018.
Office Action Summary for Non-final office action of U.S. Appl. No. 15/821,170, filed Apr. 5, 2018.
Pardoll. The blockade of immune checkpoints in cancer immunotherapy. Nat Rev Cancer. 12(4):252-264 (2012).
PCT/SG2016/050063 International Search Report and Written Opinion dated May 9, 2016.
PCT/US2017/063048 International Search Report and Written Opinion dated Mar. 5, 2018.
PCT/US2019/061549 International Search Report and Written Opinion dated Jan. 30, 2020.
Pearson et al. Improved Tools for Biological Sequence Comparison. PNAS USA 85:2444-48 (1988).
Peipp et al. A Recombinant CD7-specific Single-Chain Immunotoxin is a Potent Inducer of Apoptosis in Acute Leukemic T Cells. Cancer Research 62, pp. 2848-2855 (May 15, 2002).
Pluckthun, "Antibodies from *Escherichia coli*," in Handbook of Experimental Pharmacology; The Pharmacology of Monoclonal Antibodies; vol. 113, Chapter 11, pp. 269-315 (1994), Rosenburg and Moore eds., Springer-Verlag, New York.
Png, et al., "Blockade of CD7 expression in T cells for effective chimeric antigen receptor targeting of T-cell malignancies", Blood Advances, vol. 1, No. 25, Nov. 28, 2017, pp. 2348-2360.
Porter et al., Chimeric antigen receptor-modified T cells in chronic lymphoid leukemia. N Engl J Med 365:725-733 (2011). With correction published N. Engl J. Med (2016) 374(10) 998.
Porter et al. Induction of Graft-versus-Host Disease as Immunotherapy for Relapsed Chronic Myeloid Leukemia. N Engl J Med 1994; 330:100-106.
Raetz et al., T-cell acute lymphoblastic leukemia. American Society of Hematology, pp. 580-588 (2016). Retrieved Apr. 14, 2022 at URL: https://www.ncbi.nlm.nih.gov/pmc/articles/PMC6142501/pdf/bloodbook-2016-580.pdf.
Rosenberg et al. Adoptive cell transfer as personalized immunotherapy for human cancer. Science 348(6230):62-68 (2015).
Rossig, C. et al., "Genetic modification of T lymphocytes for adoptive immunotherapy", Molecular Therapy, 2004, vol. 10, pp. 5-18.
Rowley, J. et al., "Expression of IL-15RA or an IL-15/IL-15RA fusion on CD8+ T cells modifies adoptively transferred T-cell function in cis", European Journal of Immunology, 2009, vol. 39, pp. 491-506.
Sanz, L. et al., "Antibodies and gene therapy: teaching old 'magic bullets' new tricks", Trends in Immunology, 2004, vol. 25, pp. 85-91.
Schwartz. T cell anergy. Annu Rev Immunol. 2003;21:305-34. First published online as a Review in Advance on Dec. 5, 2002.
Sharma et al., "Novel cancer immunotherapy agents with survival benefit: recent successes and next steps," Nat Rev Cancer, 11(11):805-812 (2011).
Shimasaki et al. A clinically adaptable method to enhance the cytotoxicity of natural killer cells against B-cell malignancies. Cytotherapy, 2012; 14: 830-840.
Shimasaki et al., Natural killer cell reprogramming with chimeric immune receptors, Methods Mol Biol. 2013;969:203-20.
Slavin et al. Allogeneic cell therapy with donor peripheral blood cells and recombinant human interleukin-2 to treat leukemia relapse after allogeneic bone marrow transplantation. Blood (1996) 87 (6): 2195-2204.
Smith and Waterman, "Comparison of biosequences", Advances in Applied Mathematics, vol. 2, Issue 4, Dec. 1981, pp. 482-489.
Till et al. CD20-specific adoptive immunotherapy for lymphoma using a chimeric antigen receptor with both CD28 and 4-1BB domains: pilot clinical trial results. Blood 119(17):3940-3950 (2012).
Tsai et al., Defining and improving the genome-wide specificities of CRISPR-Cas9 nucleases, Nature Reviews Genetics, vol. 17, pp. 300-312 (May 2016). Published online Apr. 18, 2016.
Turtle et al. CD19 CAR-T cells of defined CD4+:CD8+ composition in adult B cell ALL patients. J Clin Invest 126(6):2123-2138 (2016).
U.S. Appl. No. 15/548,577 Office Action dated Jan. 14, 2019.
U.S. Appl. No. 15/548,577 Office Action dated Sep. 17, 2019.
U.S. Appl. No. 15/821,170 Notice of Allowance dated Sep. 18, 2019.
U.S. Appl. No. 15/821,170 Office Action dated Apr. 5, 2018.
U.S. Appl. No. 15/821,170 Office Action dated Mar. 27, 2019.
U.S. Appl. No. 15/821,170 Office Action dated Sep. 27, 2018.
Vodinelich et al., A monoclonal antibody (WT1) for detecting leukemias of T-cell precursors (T-ALL), Blood, vol. 62, No. 5; pp. 1108-1113 (Nov. 1983).
XP-002784541 "A simple protein-based method for generation of 'off the shelf' allogeneic chimeric antigen receptor T-cells", Journal Conference Abstract, Molecular Therapy, May 1, 2018, vol. 26, No. 5, pp. 296-297.
Yeoh et al., Classification, subtype discovery, and prediction of outcome in pediatric acute lymphoblastic leukemia by gene expression profiling. Cancer Cell, vol. 1, pp. 133-143 (Mar. 2022).
Zang et al. The B7 family and cancer therapy: costimulation and coinhibition. Clin Cancer Res 13(18) pp. 5271-5279 (Sep. 15, 2007).
Zhan et al. Modification of ricin A chain, by addition of endoplasmic reticulum (KDEL) or Golgi (YQRL) retention sequences, enhances its cytotoxicity and translocation. Cancer Immunology, Immunotherapy. vol. 46, pp. 55-60 (1998).
Zhang et al., The genetic basis of early T-cell precursor acute lymphoblastic leukaemia, Nature, vol. 481, pp. 157-163, Jan. 12, 2012.
Zhao et al. Structural Design of Engineered Costimulation Determines Tumor Rejection Kinetics and Persistence of CAR T cells. Cancer Cell 28(4):415-428 (2015).
Zhou, P. et al., "Cells transfected with a non-neutralizing antibody gene are resistant to HIV infection: targeting the endoplasmic reticulum and trans-Golgi network", The Journal of Immunology, 1998, vol. 160, pp. 1489-1496.
U.S. Appl. No. 15/821,153 Score search results SEQ ID Nos. 1 and 2. Searches run on Jan. 21, 2020. Retrieved Nov. 28, 2020.
Almagro and Fransson, Humanization of antibodies, Front. Biosci. vol. 13, pp. 1619-1633, 2008.
Rudikoff, et al. Single amino acid substitution altering antigen-binding specificity. Proc Natl Acad Sci U S A. Mar. 1982;79(6):1979-83.
U.S. Appl. No. 17/862,721 Office Action dated Sep. 7, 2022.
Score Search Results Detail for U.S. Appl. No. 17/862,721 and Search Results 20220829_091720_us-17-862-721-16.rag. Search run on Aug. 29, 2022. retrieved Aug. 30, 2022 14 pages.
Score Search Results Detail for U.S. Appl. No. 17/862,721 and Search Results 20220829_091720_us-17-862-721-16.rai. Search run on Aug. 29, 2022. retrieved Aug. 30, 2022 8 pages.
Score Search Results Detail for U.S. Appl. No. 17/862,721 and Search Results 20220829_091720_us-17-862-721-16.rapm. Search run on Aug. 29, 2022. retrieved Aug. 30, 2022 10 pages.
Score Search Results Detail for U.S. Appl. No. 17/862,721 and Search Results 20220829_091720_us-17-862-721-17.rag. Search run on Aug. 29, 2022. retrieved Aug. 30, 2022 15 pages.
Score Search Results Detail for U.S. Appl. No. 17/862,721 and Search Results 20220829_091720_us-17-862-721-17.rai. Search run on Aug. 29, 2022. retrieved Aug. 31, 2022 8 pages.

(56) References Cited

OTHER PUBLICATIONS

Score Search Results Detail for U.S. Appl. No. 17/862,721 and Search Results 20220829_091720_us-17-862-721-17.rapm. Search run on Aug. 29, 2022. retrieved Aug. 31, 2022 10 pages.
Score Search Results Detail for U.S. Appl. No. 17/862,721 and Search Results 20220829_091720_us-17-862-721-17.rpr. Search run on Aug. 29, 2022. retrieved Aug. 31, 2022 7 pages.
Score Search Results Detail for U.S. Appl. No. 17/862,721 and Search Results 20220829_091720_us-17-862-721-20.rai. Search run on Aug. 29, 2022. retrieved Aug. 31, 2022 9 pages.
Score Search Results Detail for U.S. Appl. No. 17/862,721 and Search Results 20220829_091720_us-17-862-721-20.rapm. Search run on Aug. 29, 2022. retrieved Aug. 31, 2022 11 pages.
Score Search Results Detail for U.S. Appl. No. 17/862,721 and Search Results 20220829_091720_us-17-862-721-20.rpr. Search run on Aug. 29, 2022. retrieved Aug. 31, 2022 7 pages.
Score Search Results Detail for U.S. Appl. No. 17/862,721 and Search Results 20220829_091720_us-17-862-721-21.rag. Search run on Aug. 29, 2022. retrieved Aug. 31, 2022 14 pages.
Score Search Results Detail for U.S. Appl. No. 17/862,721 and Search Results 20220829_091720_us-17-862-721-21.rai. Search run on Aug. 29, 2022. retrieved Aug. 31, 2022 8 pages.
Co-pending U.S. Appl. No. 17/862,721, inventors Campana; Dario et al., filed Jul. 12, 2022.
Co-pending U.S. Appl. No. 17/862,797, inventors Campana; Dario et al., filed Jul. 12, 2022.
U.S. Appl. No. 15/821,153 First Action Interview—Office Action dated Dec. 2, 2020.
U.S. Appl. No. 15/821,153 First Action Interview Pilot Program Pre-Interview Communication dated Aug. 24, 2020.
U.S. Appl. No. 15/821,153 Notice of Allowance dated Jun. 23, 2022.
U.S. Appl. No. 15/821,153 Office Action dated Apr. 19, 2021.
U.S. Appl. No. 15/821,153 Office Action dated Jan. 13, 2022.
Applicant's Remarks for U.S. Appl. No. 15/548,577, pp. 5-14; filed Oct. 22, 2018.
Applicant's Remarks for U.S. Appl. No. 15/548,577, pp. 5-15; filed Mar. 14, 2019.
Arakawa et al. Cloning and Sequencing of the VH and YK Genes of an Anti-CD3 Monoclonal Antibody, and Construction of a Mouse/Human Chimeric Antibody. J Biochem, vol. 120, No. 3, pp. 657-662 (1996).
Certificate of Disclosure by Benjamin D. Grimshaw signed Dec. 15, 2021 for: Grimshaw et al. Creating a Null T Cell for Adoptive Immunotherapy. Poster. Mar. 9, 2012. One page.
Certificate of Disclosure by David Linch signed Dec. 16, 2021 for: Grimshaw et al. Creating a Null T Cell for Adoptive Immunotherapy. Poster. Mar. 9, 2012. One page.
Certificate of Disclosure by Martin Pule signed Dec. 15, 2021 for: Grimshaw et al. Creating a Null T Cell for Adoptive Immunotherapy. Poster. Mar. 9, 2012. One page.
Declaration by Benjamin D. Grimshaw signed Sep. 17, 2022. 2 pages.
EP22180254.9 Extended European Search Report dated Jan. 16, 2023.
Nilsson et al. Retention and retrieval in the endoplasmic reticulum and the Golgi apparatus. Current Opinion in Cell Biology 1994, 6:517-521.
Score Search Results Details for U.S. Appl. No. 15/548,577 and Search Result 20190107_143513_us-15-548-577-37.rag. Search run on Jan. 7, 2019. retrieved Sep. 11, 2019 4 pages.
Score Search Results Details for U.S. Appl. No. 15/548,577 and Search Result 20190107_143514_us-15-548-577-36.rapbm. Search run on Jan. 7, 2019. retrieved Sep. 11, 2019 4 pages.
Score Search Results Details for U.S. Appl. No. 17/865,292 and Search Result 20220830_095127_us-17-865-292-1.rai. Search run on Aug. 30, 2022. retrieved Dec. 6, 2022 8 pages.
Score Search Results Details for U.S. Appl. No. 15/548,577 and Search Result 20190107_143513_us-15-548-577-37.rag. Search run on Jan. 7, 2019. retrieved Jan. 8, 2019 21 pages.
Score Search Results Details for U.S. Appl. No. 15/548,577 and Search Result 20190107_143514_us-15-548-577-36.rapbm. Search run on Jan. 7, 2019. retrieved Jan. 8, 2019 13 pages.
Score Search Results Details for U.S. Appl. No. 15/548,577 and Search Result 20190107_143514_us-15-548-577-37.rai. Search run on Jan. 7, 2019. retrieved Jan. 8, 2019 11 pages.
Score Search Results Details for U.S. Appl. No. 15/548,577 and Search Result 20190107_145543_us-15-548-577-32.rag. Search run on Jan. 7, 2019. retrieved Jan. 8, 2019 23 pages.
Score Search Results Details for U.S. Appl. No. 15/548,577 and Search Result 20190107_145544_us-15-548-577-32.rai. Search run on Jan. 7, 2019. retrieved Jan. 8, 2019 4 pages.
Score Search Results Details for U.S. Appl. No. 15/548,577 and Search Result 20190107_145544_us-15-548-577-32.rapbm. Search run on Jan. 7, 2019. retrieved Jan. 8, 2019 6 pages.
Score Search Results Details for U.S. Appl. No. 15/548,577 and Search Result 20190107_145544_us-15-548-577-33.rai. Search run on Jan. 7, 2019. retrieved Jan. 8, 2019 4 pages.
Score Search Results Details for U.S. Appl. No. 15/548,577 and Search Result 20190107_145544_us-15-548-577-33.rapbm. Search run on Jan. 7, 2019. retrieved Jan. 8, 2019 12 pages.
Score Search Results Details for U.S. Appl. No. 15/821,153 and Search Result 20200121_090346_us-15-821-153-1.rag. Search run on Jan. 21, 2020. retrieved Aug. 18, 2020 23 pages.
Score Search Results Details for U.S. Appl. No. 15/821,153 and Search Result 20200121_090346_us-15-821-153-2.rag. Search run on Jan. 21, 2020. retrieved Aug. 18, 2020 23 pages.
Score Search Results Details for U.S. Appl. No. 15/821,153 and Search Result 20200121_090346_us-15-821-153-2.rup. Search run on Jan. 21, 2020. retrieved Aug. 18, 2020 20 pages.
Score Search Results Details for U.S. Appl. No. 15/821,153 and Search Result 20200121_090347_us-15-821-153-1.rai. Search run on Jan. 21, 2020. retrieved Aug. 18, 2020 13 pages.
Score Search Results Details for U.S. Appl. No. 15/821,153 and Search Result 20200121_090347_us-15-821-153-1.rapbm. Search run on Jan. 21, 2020. retrieved Aug. 18, 2020 12 pages.
Score Search Results Details for U.S. Appl. No. 15/821,153 and Search Result 20200121_090347_us-15-821-153-2.rai. Search run on Jan. 21, 2020. retrieved Aug. 18, 2020 10 pages.
Score Search Results Details for U.S. Appl. No. 17/865,292 and Search Result 20220830_095119_us-17-865-292-23.rng. Search run on Aug. 30, 2022. retrieved Nov. 29, 2022 30 pages.
Score Search Results Details for U.S. Appl. No. 17/865,292 and Search Result 20220830_095119_us-17-865-292-24.rge. Search run on Aug. 30, 2022. retrieved Nov. 29, 2022 38 pages.
Score Search Results Details for U.S. Appl. No. 17/865,292 and Search Result 20220830_095119_us-17-865-292-24.rng. Search run on Aug. 30, 2022. retrieved Nov. 29, 2022 30 pages.
Score Search Results Details for U.S. Appl. No. 17/865,292 and Search Result 20220830_095120_us-17-865-292-23.rni. Search run on Aug. 30, 2022. retrieved Nov. 29, 2022 14 pages.
Score Search Results Details for U.S. Appl. No. 17/865,292 and Search Result 20220830_095120_us-17-865-292-23.rnpbm. Search run on Aug. 30, 2022. retrieved Nov. 29, 2022 15 pages.
Score Search Results Details for U.S. Appl. No. 17/865,292 and Search Result 20220830_095120_us-17-865-292-23.rnpm. Search run on Aug. 30, 2022. retrieved Nov. 29, 2022 14 pages.
Score Search Results Details for U.S. Appl. No. 17/865,292 and Search Result 20220830_095120_us-17-865-292-24.rni. Search run on Aug. 30, 2022. retrieved Nov. 29, 2022 14 pages.
Score Search Results Details for U.S. Appl. No. 17/865,292 and Search Result 20220830_095120_us-17-865-292-24.rnpbm. Search run on Aug. 30, 2022. retrieved Nov. 29, 2022 15 pages.
Score Search Results Details for U.S. Appl. No. 17/865,292 and Search Result 20220830_095120_us-17-865-292-24.rnpm. Search run on Aug. 30, 2022. retrieved Nov. 29, 2022 14 pages.
Score Search Results Details for U.S. Appl. No. 17/865,292 and Search Result 20220830_095126_us-17-865-292-1.rag. Search run on Aug. 30, 2022. retrieved Nov. 29, 2022 4 pages.
Score Search Results Details for U.S. Appl. No. 17/865,292 and Search Result 20220830_095126_us-17-865-292-1.rup. Search run on Aug. 30, 2022. retrieved Nov. 29, 2022 24 pages.

(56) References Cited

OTHER PUBLICATIONS

Score Search Results Details for U.S. Appl. No. 17/865,292 and Search Result 20220830_095126_us-17-865-292-2.rag. Search run on Aug. 30, 2022. retrieved Nov. 29, 2022 15 pages.
Score Search Results Details for U.S. Appl. No. 17/865,292 and Search Result 20220830_095126_us-17-865-292-2.rup. Search run on Aug. 30, 2022. retrieved Nov. 29, 2022 26 pages.
Score Search Results Details for U.S. Appl. No. 17/865,292 and Search Result 20220830_095127_us-17-865-292-1.rapm. Search run on Aug. 30, 2022. retrieved Nov. 29, 2022 10 pages.
Score Search Results Details for U.S. Appl. No. 17/865,292 and Search Result 20220830_095127_us-17-865-292-1.rapn. Search run on Aug. 30, 2022. retrieved Nov. 29, 2022 8 pages.
Score Search Results Details for U.S. Appl. No. 17/865,292 and Search Result 20220830_095127_us-17-865-292-23.rge. Search run on Aug. 30, 2022. retrieved Nov. 29, 2022 38 pages.
Score Search Results Details for U.S. Appl. No. 17/865,292 and Search Result 20220830_095127_us-17-865-292-2.rai. Search run on Aug. 30, 2022. retrieved Nov. 29, 2022 8 pages.
Score Search Results Details for U.S. Appl. No. 17/865,292 and Search Result 20220830_095127_us-17-865-292-2.rapm. Search run on Aug. 30, 2022. retrieved Nov. 29, 2022 10 pages.
Score Search Results Details for U.S. Appl. No. 17/865,292 and Search Result 20220830_095127_us-17-865-292-2.rapn. Search run on Aug. 30, 2022. retrieved Nov. 29, 2022 10 pages.
Score Search Results Details for U.S. Appl. No. 17/865,292 and Search Result 20220830_095127_us-17-865-292-2.rpr. Search run on Aug. 30, 2022. retrieved Nov. 29, 2022 7 pages.
U.S. Appl. No. 17/862,721 Notice of Allowance dated Feb. 15, 2023.
U.S. Appl. No. 17/862,721 Office Action dated Jan. 5, 2023.
Brown et al. Novel Treatments for Chronic Lymphocytic Leukemia and Moving Forward. American Society of Clinical Oncology Educational Book, pp. e317-e325 (2014). Retrieved at URL: https://ascopubs.org/doi/pdfdirect/10.14694/EdBook_AM.2014.34.e317.
Caruana et al. From Monoclonal Antibodies to Chimeric Antigen Receptors for the Treatment of Human Malignancies. Semin Oncol. Oct. 2014 ; 41(5): 661-666.
Certified copy of PCT/US2016/019953 priority document U.S. Appl. No. 62/121,842, Ma, Yupo et al., inventors, filed Feb. 27, 2015.
Co-pending U.S. Appl. No. 18/295,226, inventors Campana; Dario et al., filed Apr. 3, 2023.
Feng et al. Treatment of Aggressive T Cell Lymphoblastic Lymphoma/leukemia Using Anti-CD5 CAR T Cells. Stem Cell Reviews and Reports (2021) 17:652-661. Published online Jan. 6, 2021.
Fujiwara, et al. Adoptive Immunotherapy for Hematological Malignancies Using T Cells Gene-Modified to Express Tumor Antigen-Specific Receptors. Pharmaceuticals (Basel). Dec. 2014; 7(12): 1049-1068.
Glienke et al. Advantages and applications of CAR-expressing natural killer cells. Frontiers in Pharmacology, vol. 6, Article 21 (Feb. 12, 2015). 7 pages.
Guo et al. Efficiency and side effects of anti-CD38 CAR T cells in an adult patient with relapsed B-ALL after failure of bi-specific CD19/CD22 CAR T cell treatment. Cell Mol Immunol 17, 430-432 (2020).
Hishima et al. CD5 Expression in Thymic Carcinoma. American Journal of Pathology, vol. 145, No. 2, pp. 268-275 (Aug. 1994).
Imboden et al. Stimulation of CD5 enhances signal transduction by the T cell antigen receptor. J Clin Invest. 1990. 85:130-134.
Jena et al., Redirecting T-cell specificity by introducing a tumor-specific chimeric antigen receptor. Blood. 116:1035-1044 (2010).
Kapp et al. Chapter 1: Post-Targeting Functions of Signal Peptides. In Protein Transport into the Endoplasmic Reticulum, Zimmerman, ed., 2009, Landes Bioscience. 13 pages. Retrieved at URL: https://www.ncbi.nlm.nih.gov/books/NBK6322/.
Lemaistre et al. Phase I Trial of H65-RTA Immunoconjugate in Patients With Cutaneous T-cell Lymphoma. Blood, vol. 78, No. 5 Sep. 1, 1991: pp. 1173-1182.
Lewis et al. The immunophenotype of pre-TALL/LBL revisited. Experimental and Molecular Pathology 81 (2006) 162-165. Available online Aug. 14, 2006.
Li et al. Flow Cytometry in the Differential Diagnosis of Lymphocyte-Rich Thymoma From Precursor T-Cell Acute Lymphoblastic Leukemia/Lymphoblastic Lymphoma. Am J Clin Pathol 2004;121:268-274.
Litzow et al. How I treat T-cell acute lymphoblastic leukemia in adults. Blood. 2015; 126(7):833-841. Retrieved at URL: https://www.academia.edu/download/47911039/j.yexmp.2006.06.00620160809-3503-eb5sgz.pdf.
Liu et al. [NK cell surface receptors and their research progress—review]. Zhongguo shi yan xue ye xue za zhi. Aug. 2012;20(4):1034-1038. English abstract only. Retrieved at URL: https://pubmed.ncbi.nlm.nih.gov/22931679/. One page.
Morris et al. Antibody-based therapy of leukaemia. Expert Rev Mol Med. Sep. 30, 2009; 11: e29.
Pinz et al. Preclinical targeting of human T cell malignancies using CD4-specific chimeric antigen receptor (CAR)-engineered T cells. Leukemia, accepted article preview (Nov. 3, 2015). Retrieved at URL: https://www.researchgate.net/profile/Alexander-Jares/publication/283493430_Preclinical_targeting_of_human_T_cell_malignancies_using_CD4-specific_chimeric_antigen_receptor_CAR-engineered_T_cells/links/5643662808aef646e6c6a549/Preclinical-targeting-of-human-T-cell-malignancies-using-CD4-specific-chimeric-antigen-receptor-CAR-engineered-T-cells.pdf. 30 pages.
Rabinowich et al. Expression and function of CD7 molecule on human natural killer cells. J Immunol. Jan. 15, 1994;152(2):517-26. Abstract only. Retrieved at URL: https://pubmed.ncbi.nlm.nih.gov/7506726/. One page.
Rabinowich et al. Signaling via CD7 molecules on human NK cells. Induction of tyrosine phosphorylation and beta 1 integrin-mediated adhesion to fibronectin. J Immunol (1994) 153 (8): 3504-3513. Abstract only. Retrieved at URL: https://pubmed.ncbi.nlm.nih.gov/7523496/. One page.
Rezvani et al. The Application of Natural Killer Cell immunotherapy for the Treatment of Cancer. Frontiers in Immunology, vol. 6, Article 578 (Nov. 17, 2015). 13 pages.
Roitt et al. Roitt's Essential Immunology. 12th Edition, Wiley-Blackwell, Chapter 4 (2012).
Sommermeyer, et al., Chimeric antigen receptor-modified T cells derived from defined CD8+ and CD4+ subsets confer superior antitumor reactivity in vivo. Leukemia 30(2):492-500 (2016).
U.S. Appl. No. 17/862,721 Notice of Allowance dated Jun. 9, 2023.
Zhong-Fu et al. Clinical Applications of NK Cells in Tumor Immunotherapy. Chinese Journal of Biochemistry and Molecular Biology 27(12):1088-1093 (Dec. 2011). With English translation.
Johnson et al. Kabat Database and its applications: 30 years after the first variability plot. Nucleic Acids Research, 2000, vol. 28, No. 1, pp. 214-218.
Swindells et al. abYsis: Integrated Antibody Sequence and Structure—Management, Analysis and Prediction. Preprint submitted to Journal of Molecular Biology, Aug. 8, 2016. Retrieved at https://core.ac.uk/download/pdf/79528804.pdf. 2w1 pages.
Curran et al. Enhancing Antitumor Efficacy of Chimeric Antigen Receptor T Cells Through Constitutive CD4OL Expression. Molecular Therapy 23(4):769-778 (Apr. 2015).

\* cited by examiner

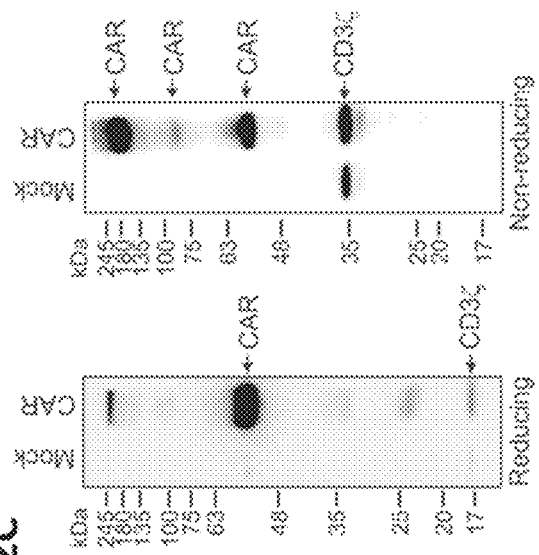
FIG. 2A
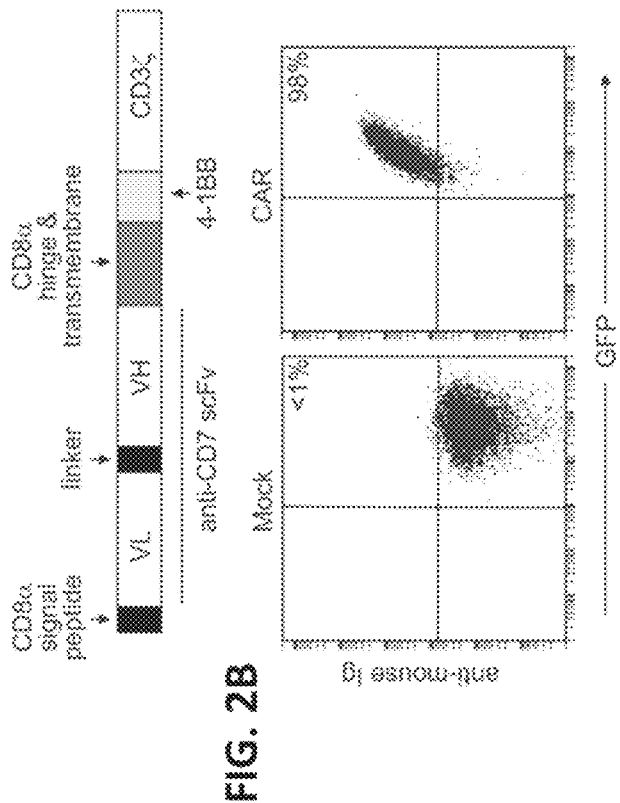
FIG. 2B
FIG. 2C
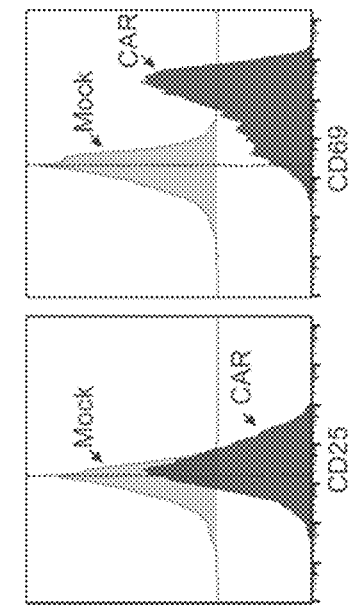
FIG. 2D
FIG. 2E
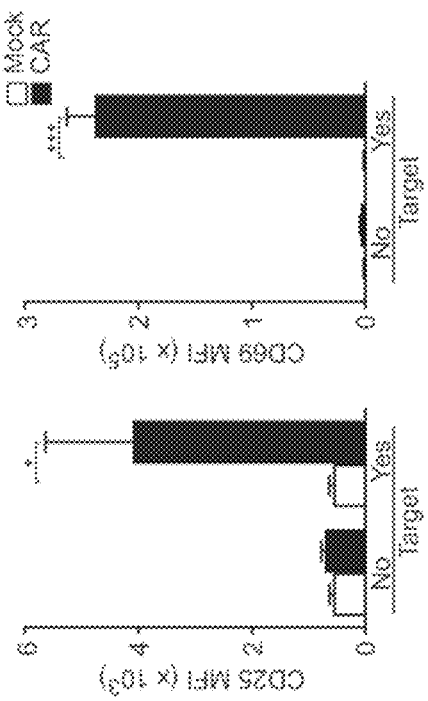

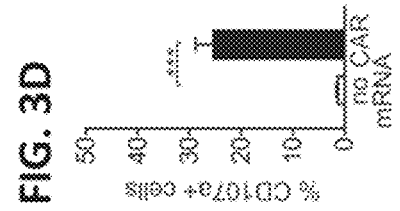
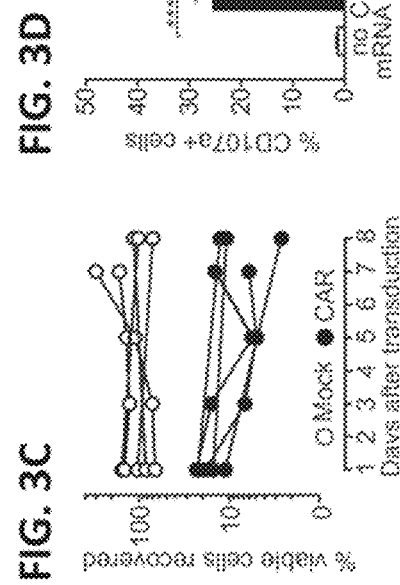
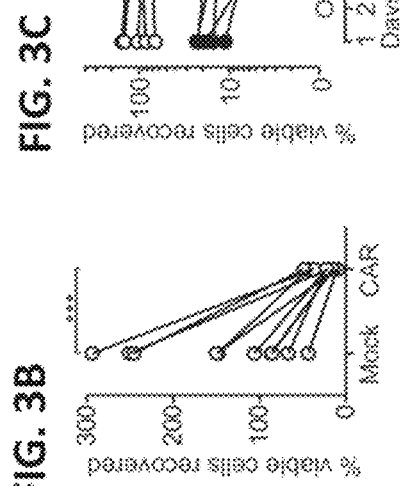
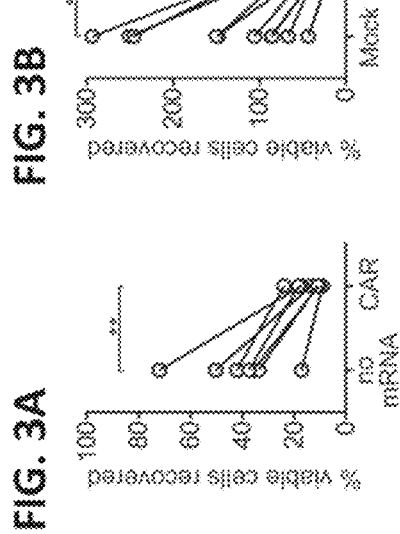

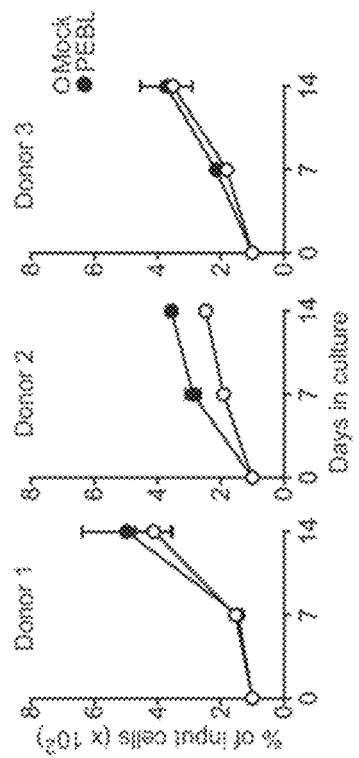
FIG. 4A
FIG. 4B
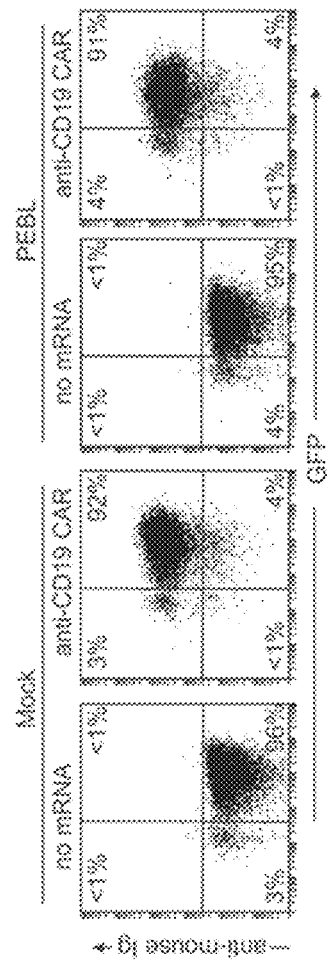
FIG. 4C

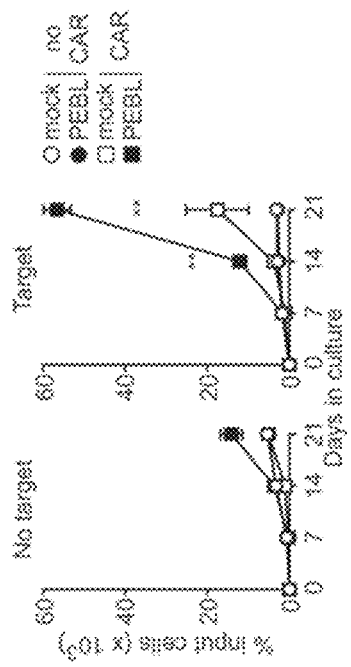
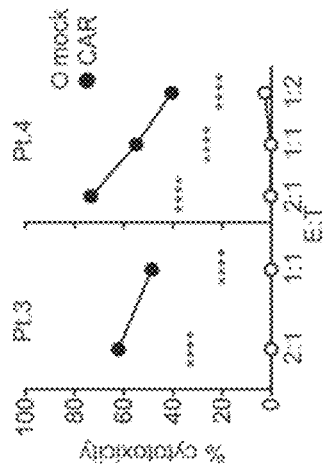
FIG. 5E
FIG. 5F

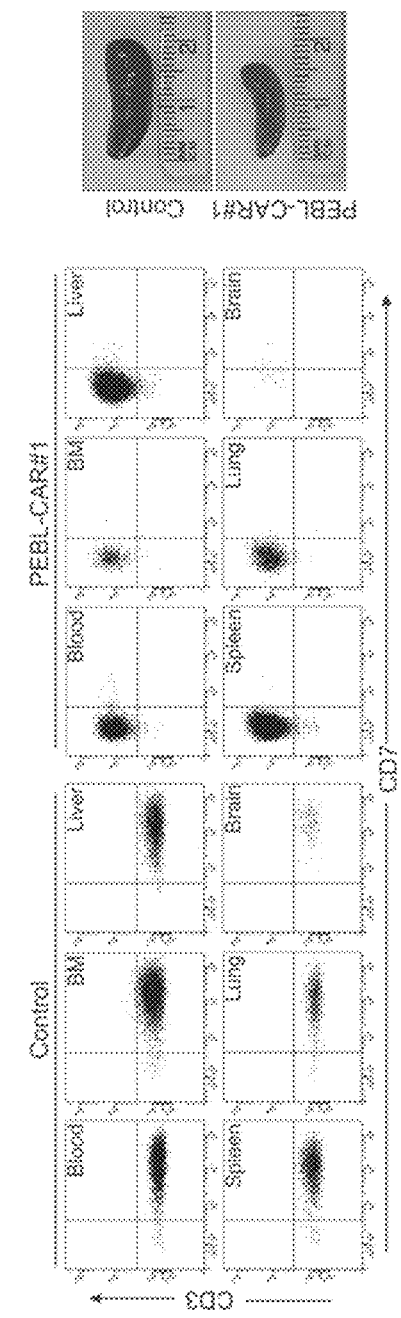

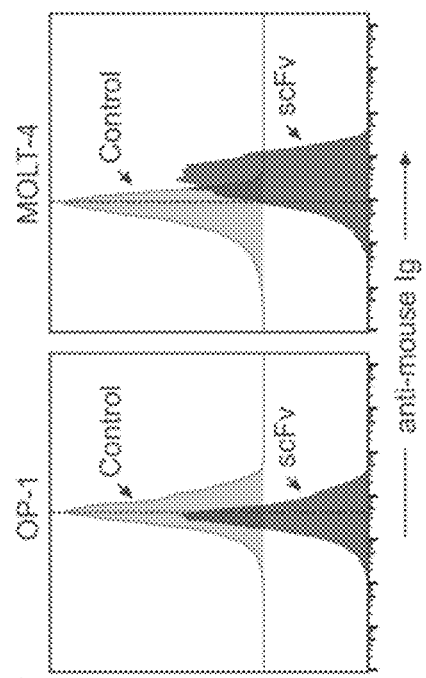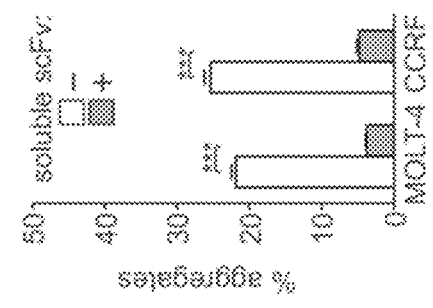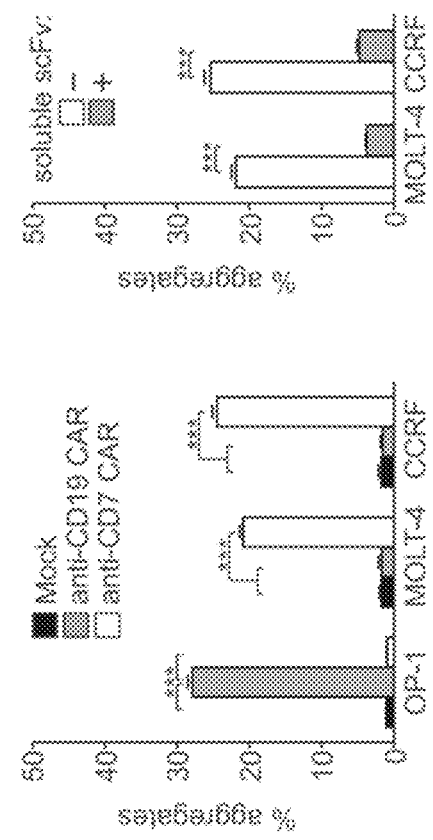
FIG. 8A
FIG. 8B
FIG. 8C

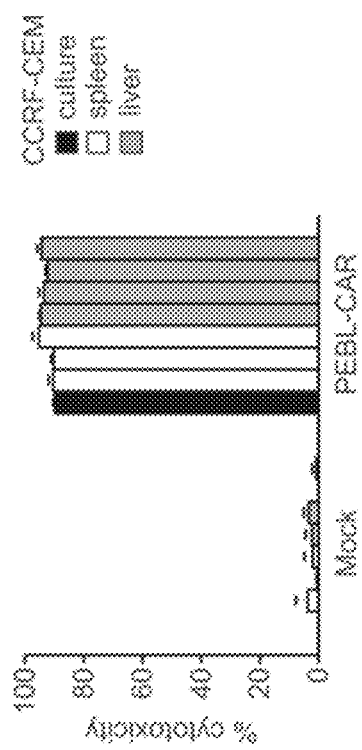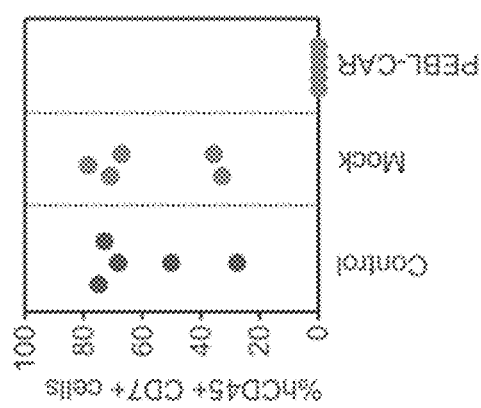
FIG. 15A
FIG. 15B

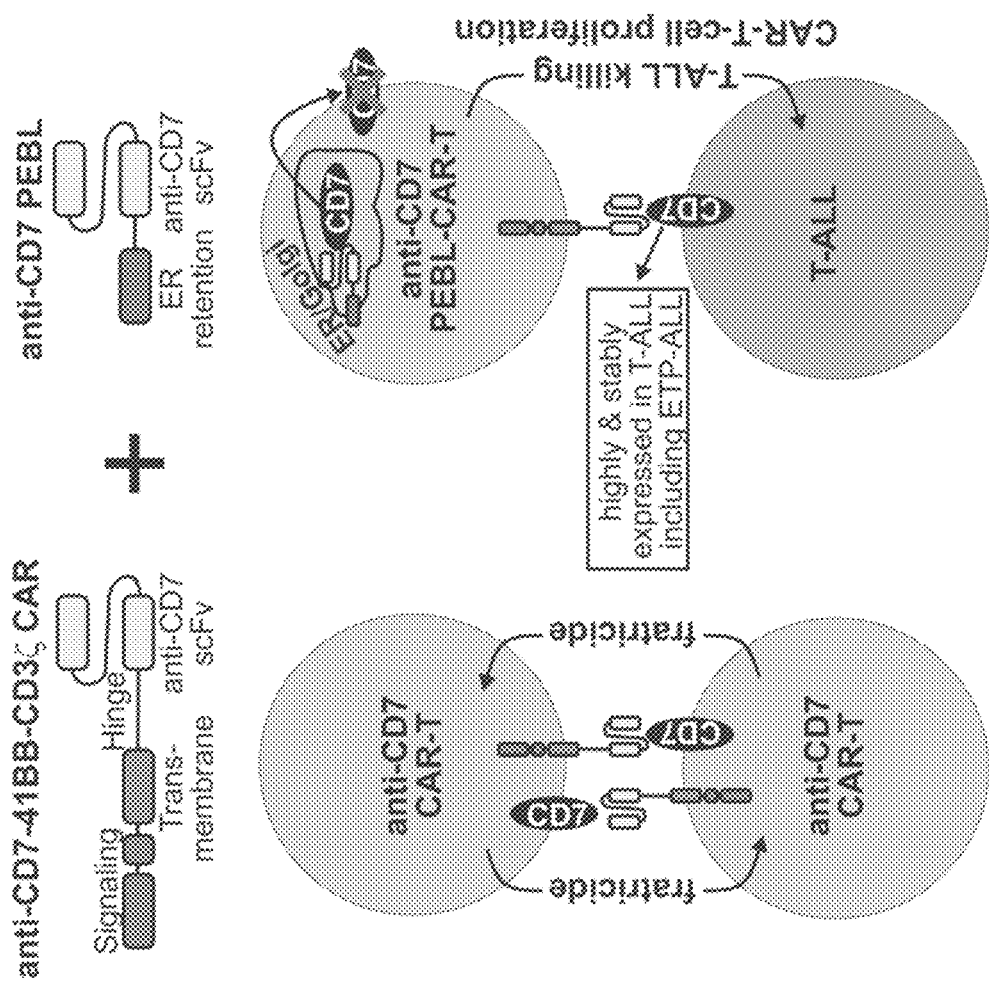

```
SEQUENCE LISTING

Sequence total quantity: 40
SEQ ID NO: 1             moltype = AA  length = 117
FEATURE                  Location/Qualifiers
REGION                   1..117
                         note = VH domain of TH69 antibody (anti-CD7 scFv)
source                   1..117
                         mol_type = protein
                         organism = synthetic construct
SEQUENCE: 1
EVQLVESGGG LVKPGGSLKL SCAASGLTFS SYAMSWVRQT PEKRLEWVAS ISSGGFTYYP   60
DSVKGRFTIS RDNARNILYL QMSSLRSEDT AMYYCARDEV RGYLDVWGAG TTVTVSS    117

SEQ ID NO: 2             moltype = AA  length = 112
FEATURE                  Location/Qualifiers
REGION                   1..112
                         note = VL domain of TH69 antibody (anti-CD7 scFv)
source                   1..112
                         mol_type = protein
                         organism = synthetic construct
SEQUENCE: 2
AAYKDIQMTQ TTSSLSASLG DRVTISCSAS QGISNYLNWY QQKPDGTVKL LIYYTSSLHS   60
GVPSRFSGSG SGTDYSLTIS NLEPEDIATY YCQQYSKLPY TFGGGTKLEI KR         112

SEQ ID NO: 3             moltype = AA  length = 42
FEATURE                  Location/Qualifiers
REGION                   1..42
                         note = intracellular signaling domain of 4-1BB
source                   1..42
                         mol_type = protein
                         organism = synthetic construct
SEQUENCE: 3
KRGRKKLLYI FKQPFMRPVQ TTQEEDGCSC RFPEEEEGGC EL                     42

SEQ ID NO: 4             moltype = AA  length = 112
FEATURE                  Location/Qualifiers
REGION                   1..112
                         note = intracellular signaling domain of CD3zeta
source                   1..112
                         mol_type = protein
                         organism = synthetic construct
```

```
SEQUENCE: 4
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 5              moltype = AA   length = 45
FEATURE                   Location/Qualifiers
REGION                    1..45
                          note = Hinge region of anti-CD7 CAR
source                    1..45
                          mol_type = protein
                          organism = synthetic construct
SEQUENCE: 5
TTTPAPRPPT PAPTIASQPL SLRPEACRPA AGGAVHTRGL DFACD                   45

SEQ ID NO: 6              moltype = AA   length = 24
FEATURE                   Location/Qualifiers
REGION                    1..24
                          note = transmembrane region of anti-CD7 CAR
source                    1..24
                          mol_type = protein
                          organism = synthetic construct
SEQUENCE: 6
IYIWAPLAGT CGVLLLSLVI TLYC                                          24

SEQ ID NO: 7              moltype = AA   length = 21
FEATURE                   Location/Qualifiers
REGION                    1..21
                          note = CD8a signal peptide of anti-CD7 CAR
source                    1..21
                          mol_type = protein
                          organism = synthetic construct
SEQUENCE: 7
MALPVTALLL PLALLLHAAR P                                             21

SEQ ID NO: 8              moltype = AA   length = 14
FEATURE                   Location/Qualifiers
REGION                    1..14
                          note = Localization domain
source                    1..14
                          mol_type = protein
                          organism = synthetic construct
SEQUENCE: 8
EQKLISEEDL KDEL                                                     14

SEQ ID NO: 9              moltype = AA   length = 11
FEATURE                   Location/Qualifiers
REGION                    1..11
                          note = Localizing domain
source                    1..11
                          mol_type = protein
                          organism = synthetic construct
SEQUENCE: 9
GGGGSAEKDE L                                                        11

SEQ ID NO: 10             moltype = AA   length = 68
FEATURE                   Location/Qualifiers
REGION                    1..68
                          note = Localizing domain
source                    1..68
                          mol_type = protein
                          organism = synthetic construct
SEQUENCE: 10
TTTPAPRPPT PAPTIASQPL SLRPEACRPA AGGAVHTRGL DFACDIYIWA PLAGTCGVLL   60
LSLVITLY                                                            68

SEQ ID NO: 11             moltype = AA   length = 15
FEATURE                   Location/Qualifiers
REGION                    1..15
                          note = Localizing domain
source                    1..15
                          mol_type = protein
                          organism = synthetic construct
SEQUENCE: 11
KYKSRRSFID EKKMP                                                    15

SEQ ID NO: 12             moltype = AA   length = 20
FEATURE                   Location/Qualifiers
REGION                    1..20
                          note = Linker
```

```
                         source           1..20
                                          mol_type = protein
                                          organism = synthetic construct
                         SEQUENCE: 12
                         GGGGSGGGGS GGGGSGGGGS                                          20

SEQ ID NO: 13     moltype = AA  length = 83
                         FEATURE           Location/Qualifiers
                         REGION            1..83
                                           note = Localizing domain
                         source            1..83
                                           mol_type = protein
                                           organism = synthetic construct
                         SEQUENCE: 13
                         TTTPAPRPPT PAPTIASQPL SLRPEACRPA AGGAVHTRGL DFACDIYIWA PLAGTCGVLL   60
                         LSLVITLYKY KSRRSFIDEK KMP                                           83

SEQ ID NO: 14     moltype = AA  length = 123
                         FEATURE           Location/Qualifiers
                         REGION            1..123
                                           note = VH domain of 3alf antibody (anti-CD7 scFv)
                         source            1..123
                                           mol_type = protein
                                           organism = synthetic construct
                         SEQUENCE: 14
                         QVQLQESGAE LVKPGASVKL SCKASGYTFT SYWMHWVKQR PGQGLEWIGK INPSNGRTNY   60
                         NEKFKSKATL TVDKSSSTAY MQLSSLTSED SAVYYCARGG VYYDLYYYAL DYWGQGTTVT  120
                         VSS                                                                123

SEQ ID NO: 15     moltype = AA  length = 108
                         FEATURE           Location/Qualifiers
                         REGION            1..108
                                           note = VL domain of 3alf antibody (anti-CD7 scFv)
                         source            1..108
                                           mol_type = protein
                                           organism = synthetic construct
                         SEQUENCE: 15
                         DIELTQSPAT LSVTPGDSVS LSCRASQSIS NNLHWYQQKS HESPRLLIKS ASQSISGIPS   60
                         RFSGSGSGTD FTLSINSVET EDFGMYFCQQ SNSWPYTFGG GTKLEIKR               108

SEQ ID NO: 16     moltype = AA  length = 120
                         FEATURE           Location/Qualifiers
                         REGION            1..120
                                           note = VH domain of T3-3A1 antibody (anti-CD7 scFv)
                         source            1..120
                                           mol_type = protein
                                           organism = synthetic construct
                         SEQUENCE: 16
                         DVQLVESGGG LVQPGGSRKL SCAASGFTFS SFGMHWVRQA PEKGLEWVAY ISSGSSTLHY   60
                         ADTVKGRFTI SRDNPKNTLF LQMTSLRSED TAMYYCARWG NYPHYAMDYW GQGTSVTVSS  120

SEQ ID NO: 17     moltype = AA  length = 111
                         FEATURE           Location/Qualifiers
                         REGION            1..111
                                           note = VL domain of T3-3A1 antibody (anti-CD7 scFv)
                         source            1..111
                                           mol_type = protein
                                           organism = synthetic construct
                         SEQUENCE: 17
                         DIVMTQSPAS LAVSLGQRAT ISCRASKSVS ASGYSYMHWY QQKPGQPPKL LIYLASNLES   60
                         GVPARFSGSG SGTDFTLNIH PVEEEDAVTY YCQHSRELPY TFGGGTKLEI K           111

SEQ ID NO: 18     moltype = AA  length = 4
                         FEATURE           Location/Qualifiers
                         REGION            1..4
                                           note = Localizing sequence
                         source            1..4
                                           mol_type = protein
                                           organism = synthetic construct
                         SEQUENCE: 18
                         KDEL                                                                 4

SEQ ID NO: 19     moltype =     length =
                         SEQUENCE: 19
                         000

SEQ ID NO: 20     moltype =     length =
                         SEQUENCE: 20
                         000
```

```
SEQ ID NO: 21           moltype = AA  length = 4
FEATURE                 Location/Qualifiers
REGION                  1..4
                        note = Localizing sequence
source                  1..4
                        mol_type = protein
                        organism = synthetic construct
SEQUENCE: 21
YQRL                                                                    4

SEQ ID NO: 22           moltype = AA  length = 4
FEATURE                 Location/Qualifiers
REGION                  1..4
                        note = Proteasome localizing sequence
source                  1..4
                        mol_type = protein
                        organism = synthetic construct
SEQUENCE: 22
PEST                                                                    4

SEQ ID NO: 23           moltype = DNA  length = 351
FEATURE                 Location/Qualifiers
misc_feature            1..351
                        note = VH domain of TH69 antibody (anti-CD7 scFv)
source                  1..351
                        mol_type = other DNA
                        organism = synthetic construct
SEQUENCE: 23
gaggtgcagc tggtcgaatc tggaggagga ctggtgaagc caggaggatc tctgaaactg    60
agttgtgccg cttcaggcct gaccttctca agctacgcca tgagctgggt gcgacagaca   120
cctgagaagc ggctgaatg ggtcgctagc atctcctctg gcgggttcac atactatcca   180
gactccgtga aggcagatt tactatctct cgggataacg caagaaatat tctgtacctg   240
cagatgagtt cactgaggag cgaggacacc gcaatgtact attgtgccag ggacgaagtg   300
cgcggctatc tggatgtctg gggagctggc actaccgtca ccgtctccag c           351

SEQ ID NO: 24           moltype = DNA  length = 351
FEATURE                 Location/Qualifiers
misc_feature            1..351
                        note = VL domain of TH69 antibody (anti-CD7 scFv)
source                  1..351
                        mol_type = other DNA
                        organism = synthetic construct
SEQUENCE: 24
gaggtgcagc tggtcgaatc tggaggagga ctggtgaagc caggaggatc tctgaaactg    60
agttgtgccg cttcaggcct gaccttctca agctacgcca tgagctgggt gcgacagaca   120
cctgagaagc ggctgaatg ggtcgctagc atctcctctg gcgggttcac atactatcca   180
gactccgtga aggcagatt tactatctct cgggataacg caagaaatat tctgtacctg   240
cagatgagtt cactgaggag cgaggacacc gcaatgtact attgtgccag ggacgaagtg   300
cgcggctatc tggatgtctg gggagctggc actaccgtca ccgtctccag c           351

SEQ ID NO: 25           moltype = DNA  length = 369
FEATURE                 Location/Qualifiers
misc_feature            1..369
                        note = VH domain of 3alf antibody (anti-CD7 scFv)
source                  1..369
                        mol_type = other DNA
                        organism = synthetic construct
SEQUENCE: 25
caggtccagc tgcaggagtc aggagctgag ctggtgaagc caggggcaag cgtcaaactg    60
tcctgcaagg cctctggata tacattcact agctactgga tgcactgggt gaaacagaga   120
cccgacagg gcctggagtg gatcggaaag attaacccta gcaatggcag gaccaactac   180
aacgaaaagt ttaaatccaa ggcaaccctg acagtggaca gagctcctc tacagcctac   240
atgcagctga gttcactgac ttcagaggat agcgcagtgt actattgcgc cagaggcggg   300
gtctactatg acctgtacta ttacgccctg gattattggg ggcagggaac cacagtgact   360
gtcagctcc                                                           369

SEQ ID NO: 26           moltype = DNA  length = 324
FEATURE                 Location/Qualifiers
misc_feature            1..324
                        note = VL domain of 3alf antibody (anti-CD7 scFv)
source                  1..324
                        mol_type = other DNA
                        organism = synthetic construct
SEQUENCE: 26
gacatcgagc tgacccagag tcctgctaca ctgagcgtga ctccaggcga ttctgtcagt    60
ctgtcatgtc gggcaagcca gtccatctct aacaatctgc actggtacca gcagaaatcc   120
catgaatctc cacgactgct gattaagagt gcctcacaga gcatctccgg cattccctcc   180
cggttctctg gcagtgggtc aggaactgac tttaccctga gtattaactc agtggagaca   240
```

```
gaagatttcg gcatgtattt tgccagcag agcaattcct ggccctacac tttcggaggc    300
gggaccaaac tggagatcaa gcgg                                          324
```

| SEQ ID NO: 27 | moltype = DNA  length = 360 |
|---|---|
| FEATURE | Location/Qualifiers |
| misc_feature | 1..360 |
| | note = VH domain of T3-4A1 antibody (anti-CD7 scFv) |
| source | 1..360 |
| | mol_type = other DNA |
| | organism = synthetic construct |

SEQUENCE: 27
```
gatgtgcagc tggtggagtc tgggggaggc ttagtgcagc ctggagggtc ccggaaactc    60
tcctgtgcag cctctggatt cactttcagt agctttggaa tgcactgggt tcgtcaggct   120
ccagagaagg ggctggagtg ggtcgcatac attagtagta gtggtagtac cctccactat   180
gcagacacag tgaagggccg attcaccatc tccagagaca atcccaagaa caccctgttc   240
ctgcaaatga ccagtctaag gtctgaggac acggccatgt attactgtgc aagatggggt   300
aactaccctc actatgctat ggactactgg ggtcaaggaa cctcagtcac cgtctcctca   360
```

| SEQ ID NO: 28 | moltype = DNA  length = 333 |
|---|---|
| FEATURE | Location/Qualifiers |
| misc_feature | 1..333 |
| | note = VL domain of T3-4A1 antibody (anti-CD7 scFv) |
| source | 1..333 |
| | mol_type = other DNA |
| | organism = synthetic construct |

SEQUENCE: 28
```
gacattgtga tgacccagtc tcctgcttcc ttagctgtat ctctggggca gagggccacc    60
atctcatgca gggccagcaa aagtgtcagt gcatctggct atagttatat gcactggtac   120
caacagaaac caggacagcc acccaaactc ctcatctatc ttgcatccaa cctagaatct   180
ggggtccctg ccaggttcag tggcagtggg tctgggacag acttcaccct caacatccat   240
cctgtggagg aggaggatgc tgtaacctat tactgtcagc acagtaggga gcttccgtac   300
acgttcggag ggggaccaa gctggaaata aaa                                 333
```

| SEQ ID NO: 29 | moltype = AA  length = 5 |
|---|---|
| FEATURE | Location/Qualifiers |
| REGION | 1..5 |
| | note = Polypeptide linker |
| source | 1..5 |
| | mol_type = protein |
| | organism = synthetic construct |

SEQUENCE: 29
```
GGGGS                                                                  5
```

| SEQ ID NO: 30 | moltype = DNA  length = 63 |
|---|---|
| FEATURE | Location/Qualifiers |
| misc_feature | 1..63 |
| | note = CD8alpha signal peptide |
| source | 1..63 |
| | mol_type = other DNA |
| | organism = synthetic construct |

SEQUENCE: 30
```
atggctctgc ctgtgaccgc actgctgctg ccctggctc tgctgctgca cgccgcaaga    60
cct                                                                  63
```

| SEQ ID NO: 31 | moltype = DNA  length = 60 |
|---|---|
| FEATURE | Location/Qualifiers |
| misc_feature | 1..60 |
| | note = VH-VL Linker |
| source | 1..60 |
| | mol_type = other DNA |
| | organism = synthetic construct |

SEQUENCE: 31
```
ggaggaggag gaagcggagg aggaggatcc ggaggcgggg gatctggagg aggaggaagt    60
```

| SEQ ID NO: 32 | moltype = DNA  length = 42 |
|---|---|
| FEATURE | Location/Qualifiers |
| misc_feature | 1..42 |
| | note = ER localization domain, KDEL tethered to scFv with myc ("mycKDEL") |
| source | 1..42 |
| | mol_type = other DNA |
| | organism = synthetic construct |

SEQUENCE: 32
```
gagcagaaac tgattagcga agaggacctg aaagatgaac tg                       42
```

| SEQ ID NO: 33 | moltype = DNA  length = 78 |
|---|---|
| FEATURE | Location/Qualifiers |
| misc_feature | 1..78 |
| | note = localization domain, "link.(20)AEKDEL" |

```
source                  1..78
                        mol_type = other DNA
                        organism = synthetic construct
SEQUENCE: 33
ggtggtggcg gcagtggtgg cggtggctca ggcggtggtg gctccggtgg cggtggctct    60
gcagaaaaag atgagttg                                                  78

SEQ ID NO: 34           moltype = DNA  length = 249
FEATURE                 Location/Qualifiers
misc_feature            1..249
                        note = localization domain, "mb DEKKMP"
source                  1..249
                        mol_type = other DNA
                        organism = synthetic construct
SEQUENCE: 34
accactacac ctgcaccaag gcctcccaca cccgctccca ctatcgcttc ccagccactg    60
tccctgaggc ccgaggcctg caggccagca gctggcggag ccgtgcatac tagggggctg   120
gacttcgctt gcgacatcta catctgggcc ccactggcag gacatgcgg agtcctgctg    180
ctgtccctgg tcatcacact ttacaaatac aaaagcagac gcagttttat tgatgaaaag   240
aaaatgcct                                                           249

SEQ ID NO: 35           moltype = DNA  length = 126
FEATURE                 Location/Qualifiers
misc_feature            1..126
                        note = Nucleic acid sequence of intracellular signaling
                         domain of 4-1BB
source                  1..126
                        mol_type = other DNA
                        organism = synthetic construct
SEQUENCE: 35
aagcggggc gcaaaaaact gctgtatatc tttaagcagc cttttcatgag accagtgcag     60
acaacccagg aggaagatgg gtgctcatgc cggtttcccg aggaggagga aggcggctgc   120
gagctg                                                              126

SEQ ID NO: 36           moltype = DNA  length = 336
FEATURE                 Location/Qualifiers
misc_feature            1..336
                        note = intracellular signaling domain of CD3zeta
source                  1..336
                        mol_type = other DNA
                        organism = synthetic construct
SEQUENCE: 36
agggtgaagt tttcccgctc agcagatgct cctgcctacc agcagggcca gaaccagctg    60
tataatgagc tgaacctggg cagacgcgaa gagtatgatg tgctggacaa aaggcgggga   120
agagaccccg aaatgggagg gaagccaagg cggaaaaacc cccaggaggg cctgtacaat   180
gagctgcaga aggacaaaat ggcagaggct tacagtgaga ttgggatgaa gggagagaga   240
cggagggaa aagggcacga tggcctgtac caggggctga gcacagcaac caagatact    300
tatgacgcac tgcacatgca ggcactgcca cccaga                             336

SEQ ID NO: 37           moltype = DNA  length = 204
FEATURE                 Location/Qualifiers
misc_feature            1..204
                        note = Hinge and transmembrane domain of CD8alpha
source                  1..204
                        mol_type = other DNA
                        organism = synthetic construct
SEQUENCE: 37
accactacac ctgcaccaag gcctcccaca cccgctccca ctatcgcttc ccagccactg    60
tccctgaggc ccgaggcctg caggccagca gctggcggag ccgtgcatac tagggggctg   120
gacttcgctt gcgacatcta catctgggcc ccactggcag gacatgcgg agtcctgctg    180
ctgtccctgg tcatcacact gtac                                          204

SEQ ID NO: 38           moltype = DNA  length = 15
FEATURE                 Location/Qualifiers
misc_feature            1..15
                        note = synthetic oligonucleotide primer
source                  1..15
                        mol_type = other DNA
                        organism = synthetic construct
SEQUENCE: 38
atggccgggc ctccg                                                    15

SEQ ID NO: 39           moltype = DNA  length = 18
FEATURE                 Location/Qualifiers
misc_feature            1..18
                        note = synthetic oligonucleotide primer
source                  1..18
                        mol_type = other DNA
                        organism = synthetic construct
```

```
SEQUENCE: 39
tcactggtac tggttggg                                                    18

SEQ ID NO: 40           moltype = AA  length = 10
FEATURE                 Location/Qualifiers
REGION                  1..10
                        note = Localizing domain
source                  1..10
                        mol_type = protein
                        organism = synthetic construct
SEQUENCE: 40
EQKLISEEDL                                                             10
```

BLOCKADE OF CD7 EXPRESSION AND CHIMERIC ANTIGEN RECEPTORS FOR IMMUNOTHERAPY OF T-CELL MALIGNANCIES

CROSS-REFERENCE TO RELATED APPLICATIONS

The present application is a continuation of U.S. application Ser. No. 15/821,153, filed Nov. 22, 2017, now U.S. Pat. No. 11,440,958, which claims the benefit of U.S. Provisional Application No. 62/425,398, filed on Nov. 22, 2016, and U.S. Provisional Application No. 62/543,696, filed Aug. 10, 2017, which are expressly incorporated by reference in their entirety for all purposes.

SEQUENCE LISTING

The instant application contains a Sequence Listing which has been submitted electronically in XML format and is hereby incorporated by reference in its entirety. Said XML copy, created on Jul. 14, 2022, is named 62190_702_301_SL.xml and is 53,390 bytes in size.

BACKGROUND OF THE INVENTION

Chimeric antigen receptors (CARs) can redirect immune cells to specifically recognize and kill tumor cells. CARs are artificial multi-molecular proteins constituted by a single-chain variable region (scFv) of an antibody linked to a signaling molecule via a transmembrane domain. When the scFv ligates its cognate antigen, signal transduction is triggered, resulting in tumor cell killing by CAR-expressing cytotoxic T lymphocytes (Eshhar Z, Waks T, et al. PNAS USA. 90(2):720-724, 1993; Geiger T L, et al. J Immunol. 162(10):5931-5939, 1999; Brentjens R J, et al. Nat Med. 9(3):279-286, 2003; Cooper L J, et al. Blood 101(4):1637-1644, 2003; Imai C, et al. Leukemia. 18:676-684, 2004). Clinical trials with CAR-expressing autologous T lymphocytes have shown positive responses in patients with B-cell refractory leukemia and lymphoma (see, e.g., Till B G, et al. Blood 119(17):3940-3950, 2012; Maude S L, et al. N Engl J Med. 371(16):1507-1517, 2014).

The development of CAR technology to target T cell malignancies has lagged far behind the progress made for their B-cell counterparts. Novel therapies for T-cell malignancies are needed but progress to date has been slow. In particular, effective immunotherapeutic options are lacking and treatment of T-cell acute lymphocytic leukemia (T-ALL) relies on intensive chemotherapy and hematopoietic stem cell transplant. Despite the morbidity and mortality of these approaches, results are far from satisfactory.

In sum, there is a significant unmet need for new therapeutic options for patients with T-cell malignancies.

SUMMARY OF THE INVENTION

In one aspect, the present invention provides an engineered immune cell comprising: (i) a nucleic acid comprising a nucleotide sequence encoding a target-binding molecule linked to a localizing domain, wherein said target-binding molecule is a first antibody that specifically binds to CD7; and (ii) a nucleic acid comprising a nucleotide sequence encoding a chimeric antigen receptor (CAR), wherein said CAR comprises a 4-1BB intracellular signaling domain, a CD3ζ intracellular signaling domain, and a second antibody that specifically binds to CD7.

In some embodiments, the first antibody that specifically binds to CD7 is a first single chain variable fragment (scFv). In certain embodiments, the second antibody that specifically binds to CD7 is a second single chain variable fragment (scFv).

In some embodiments, the first single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the first single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In certain embodiments, the first single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the localizing domain comprising an amino acid sequence selected from the group consisting of an endoplasmic reticulum (ER) retention sequence, a Golgi retention sequence, a proteasome localizing sequence, and a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the localizing domain comprises an endoplasmic reticulum (ER) retention sequence comprising an amino acid sequence of SEQ ID NO:8 or SEQ ID NO:9. In other embodiments, the localizing domain comprises transmembrane domain sequence derived from CD8a hinge and transmembrane domain sequence comprising an amino acid sequence of SEQ ID NO:13. In some embodiments, proteasome localization of the target-binding molecule (e.g., scFv) is achieved by linking the scFv sequence to a tripartite motif containing 21 (TRIM21) targeting domain sequence and coexpressing a nucleic acid sequence encoding the human TRIM21 E3 ubiquitin ligase protein.

In some embodiments, the 4-1BB intracellular signaling domain comprises an amino acid sequence of SEQ ID NO:3 and wherein the CD3ζ intracellular signaling domain comprises an amino acid sequence of SEQ ID NO:4.

In some embodiments, the hinge and transmembrane domain comprises an amino acid sequence of SEQ ID NO:10.

In some embodiments, the second single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the second single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In yet other embodiments, the second single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the engineered cell is an engineered T cell, an engineered natural killer (NK) cell, an engineered NK/T cell, an engineered monocyte, an engineered macrophage, or an engineered dendritic cell.

In another aspect, the present invention provides an engineered immune cell comprising: (i) a target-binding molecule linked to a localizing domain, wherein said target-binding molecule is a first antibody that specifically binds to CD7; and (ii) a chimeric antigen receptor (CAR), wherein said CAR comprises a 4-1BB intracellular signaling domain, a CD3ζ intracellular signaling domain, and a second antibody that specifically binds to CD7.

In some embodiments, the first antibody that specifically binds to CD7 is a first single chain variable fragment (scFv). In certain embodiments, the second antibody that specifically binds to CD7 is a second single chain variable fragment (scFv).

In some embodiments, the first single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the first single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In certain embodiments, the first single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the localizing domain comprising an amino acid sequence selected from the group consisting of an endoplasmic reticulum (ER) retention sequence, a Golgi retention sequence, a proteasome localizing sequence, and a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the localizing domain comprises an endoplasmic reticulum (ER) retention sequence comprising an amino acid sequence of SEQ ID NO:8 or SEQ ID NO:9. In other embodiments, the localizing domain comprises transmembrane domain sequence derived from CD8a hinge and transmembrane domain sequence comprising an amino acid sequence of SEQ ID NO:13.

In some embodiments, the 4-1BB intracellular signaling domain comprises an amino acid sequence of SEQ ID NO:3 and wherein the CD3ζ intracellular signaling domain comprises an amino acid sequence of SEQ ID NO:4.

In some embodiments, the hinge and transmembrane domain comprises an amino acid sequence of SEQ ID NO:10.

In some embodiments, the second single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the second single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In yet other embodiments, the second single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the engineered cell is an engineered T cell, an engineered natural killer (NK) cell, an engineered NK/T cell, an engineered monocyte, an engineered macrophage, or an engineered dendritic cell.

In some embodiments, provided herein is a pharmaceutical composition comprising the engineered immune cell described herein and a pharmaceutically acceptable carrier.

In another aspect, the present invention provides methods of producing the engineered immune cell described herein. The method can comprise: (i) introducing into an immune cell (a) a first nucleic acid comprising a nucleotide sequence encoding a target-binding molecule linked to a localizing domain, wherein said target-binding molecule is a first antibody that specifically binds to CD7; and (b) a second nucleic acid comprises a nucleotide sequence encoding a CAR, wherein said CAR comprises a 4-1BB intracellular signaling domain, a CD3ζ intracellular signaling domain, and a second antibody that specifically binds to CD7; and (ii) isolating the engineered immune cell comprising said target-binding molecule linked to said localizing domain and said CAR, thereby producing said engineered immune cell.

In yet another aspect, the present invention provides methods of treating cancer in a subject (e.g., patient) in need thereof, comprising administering a therapeutic amount of an engineered immune cell to said patient, thereby treating cancer in the subject in need thereof. In some embodiments, engineered immune cell comprises: (i) a nucleic acid comprising a nucleotide sequence encoding a target-binding molecule linked to a localizing domain, wherein said target-binding molecule is a first antibody that specifically binds to CD7; and (ii) a nucleic acid comprising a nucleotide sequence encoding a chimeric antigen receptor (CAR), wherein said CAR comprises a 4-1BB intracellular signaling domain, a CD3ζ intracellular signaling domain, and a second antibody that specifically binds to CD7.

In some embodiments, the first antibody that specifically binds to CD7 is a first single chain variable fragment (scFv). In certain embodiments, the second antibody that specifically binds to CD7 is a second single chain variable fragment (scFv).

In some embodiments, the first single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the first single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In certain embodiments, the first single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the localizing domain comprising an amino acid sequence selected from the group consisting of an endoplasmic reticulum (ER) retention sequence, a Golgi retention sequence, a proteasome localizing sequence, and a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In some embodiments, the localizing domain comprises an endoplasmic reticulum (ER) retention sequence comprising an amino acid sequence of SEQ ID NO:8 or SEQ ID NO:9. In other embodiments, the localizing domain comprises transmembrane domain sequence derived from CD8a hinge and transmembrane domain sequence comprising an amino acid sequence of SEQ ID NO:13.

In some embodiments, the 4-1BB intracellular signaling domain comprises an amino acid sequence of SEQ ID NO:3 and wherein the CD3ζ intracellular signaling domain comprises an amino acid sequence of SEQ ID NO:4.

In some embodiments, the hinge and transmembrane domain comprises an amino acid sequence of SEQ ID NO:10.

In some embodiments, the second single chain variable fragment (scFv) comprises a heavy chain variable domain having at least 90% sequence identity to the amino acid sequence of SEQ ID NO:1 and a light chain variable domain having at least 90% sequence identity to the amino acid sequence of SEQ ID NO:2. In other embodiments, the second single chain variable fragment (scFv) comprises a heavy chain variable domain having at least 90% sequence identity to the amino acid sequence of SEQ ID NO:14 and a light chain variable domain having at least 90% sequence identity to the amino acid sequence of SEQ ID NO:15. In yet other embodiments, the second single chain variable fragment (scFv) comprises a heavy chain variable domain having at least 90% sequence identity to the amino acid sequence of SEQ ID NO:16 and a light chain variable domain having at least 90% sequence identity to the amino acid sequence of SEQ ID NO:17.

In some embodiments, the engineered cell is an engineered T cell, an engineered natural killer (NK) cell, an engineered NK/T cell, an engineered monocyte, an engineered macrophage, or an engineered dendritic cell.

In some embodiments, the engineered immune cell is administered into said subject (e.g., patient) by intravenous infusion, intra-arterial infusion, intraperitoneal infusion, direct injection into tumor and/or perfusion of tumor bed after surgery, implantation at a tumor site in an artificial scaffold, or intrathecal administration.

In some embodiments, the cancer is a T cell malignancy. In one embodiment, the T cell malignancy is early T cell progenitor acute lymphoblastic leukemia (ETP-ALL).

The present disclosure provides engineered immune cells and methods of use thereof for treating T cell hematologic malignancies. One skilled in the art recognizes that self-killing or fratricide of CAR T-cells and killing of normal T cells can arise when CAR-T effector cells are used to treat T cell leukemias. As such, there is a need for engineered immune cells and therapeutic methods that minimize or eliminate T cell fratricide.

The engineered immune cells and treatment methods described herein utilize novel fratricide-resistant CAR-T cells, such as engineered anti-CD7 PEBL and anti-CD7 CAR-T cells. The engineered immune cells can elicit potent and durable therapeutic effects in patients with T-cell malignancies including relapsed T-cell malignancies. Such cells can result in efficient targeting and killing of malignant T cells without significant effector T cell fratricide.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A-FIG. 2E show the design, expression and signaling of the anti-CD7 CAR. Schema of the anti-CD7-41BB-CD3ζ construct (FIG. 2A). Flow cytometric analysis of Jurkat cells transduced with either GFP alone ("Mock") or GFP plus anti-CD7 CAR. Dot plots illustrate GFP fluorescence, and CAR expression after staining with biotin-conjugated goat anti-mouse F(ab')2 antibody and streptavidin-APC (Jackson ImmunoResearch) (FIG. 2B). Western blot analysis of CAR expression in Jurkat cells (FIG. 2C). Cell lysates of mck- and CAR-transduced Jurkat cells were separated on a 10% polyacrylamide gel under reducing or non-reducing conditions. The blotted membrane was probed with mouse anti-human CD3ζ antibody (8D3; BD Biosciences) and goat anti-mouse IgG conjugated to horseradish peroxidase (R&D Systems). Antibody binding was revealed with Clarity Western ECL Substrate (Bio-Rad). Anti-CD7 CAR induces expression of activation markers upon ligation. Bars show mean (±SD) of CD25 and CD69 MFI in CAR- and mock-transduced Jurkat cells after 24 hours with or without CD7+ MOLT-4 cells. P values by t test are shown for significant differences (*=0.016; ***<0.001) (FIG. 2D). FIG. 2E provides representative flow cytometric histograms of the experiments shown in FIG. 2D.

FIG. 3A-FIG. 3I illustrate expression of anti-CD7 CAR in human peripheral blood T-cells results in fratricide which is prevented by CD7 downregulation. Percentage of viable T cells recovered 24 hours after electroporation with or without anti-CD7 CAR mRNA (n=7) (FIG. 3A). Viable cells were counted by flow cytometry. Percentage of viable T cells recovered 24 hours after CAR transduction with a retroviral vector as compared to cells from the same donors transduced with GFP alone ("Mock") (n=10) (FIG. 3B). Percent of viable CAR- or mock-transduced T cells recovered during the week following transduction (FIG. 3C). Shown are follow-up results for 5 of the 10 experiments shown in FIG. 3B. Percentage of CD107a in T cells after electroporation with or without anti-CD7 CAR mRNA (FIG. 3D). Mean (±SD) of triplicate measurements are shown. Schematic representation of anti-CD7 Protein Expression Blocker (PEBL) constructs (FIG. 3E). Representative flow cytometric histograms illustrate CD7 expression in T-lymphocytes after retroviral transduction of 3 anti-CD7 PEBLs, or mock-transduced GFP alone ("Mock") (FIG. 3F). T-cells were stained with anti-CD7-PE (M-T701; BD Biosciences). Percentage of CD7 expression in T cells retrovirally transduced with the anti-CD7 PEBL-1, or mock-transduced (n=5) (FIG. 3G). Flow cytometric dot plots illustrate downregulation of CD7 expression in T cells by PEBL transduction, together with expression of anti-CD7-41BB-CD3ζ CAR 12 hours after electroporation with or without CAR mRNA (FIG. 3H). Cells were stained with biotin-conjugated goat anti-mouse F(ab')2 antibody and streptavidin-APC (Jackson ImmunoResearch). Percentage of viable T cells transduced with anti-CD7 PEBL recovered 24 hours after electroporation of anti-CD7 CAR mRNA as compared to cells electroporated with the anti-CD7 CAR mRNA but transduced with a vector without anti-CD7 PEBL (n=6) (FIG. 3I). Number of viable cells was measured by flow cytometry. , P<0.01; *, P<0.001.

FIG. 4A-FIG. 4F show that CD7 downregulation by PEBL did not alter T-cell phenotype, proliferation and functionality. Percentage of CD4 and CD8 cells 7-14 days after retroviral transduction with either anti-CD7 PEBL or GFP alone ("Mock") (FIG. 4A). Each symbol corresponds to a different T cell donor. Growth rate of PEBL- and mock-transduced T cells (from 3 donors) maintained with 200 IU/mL IL-2 for 14 days (FIG. 4B). Symbols represent mean (±SD) of triplicate measurements. PEBL- and mock-transduced T cells were electroporated with either anti-CD19-41BB-CD3ζ CAR mRNA or no mRNA (FIG. 4C). Flow cytometric dot plots illustrate GFP and CAR expression 12 hours after electroporation. CAR was detected with biotin-conjugated goat anti-mouse F(ab')2 antibody and streptavidin-APC (Jackson ImmunoResearch). Cytotoxicity of PEBL- or mock-transduced T cells, electroporated with or without anti-CD19 CAR mRNA, against CD19+ ALL cells (OP-1) (FIG. 4D). Bars show mean (±SD) of 4-hour cytotoxicity at a 1:1 E:T. FIG. 4E shows CD107a expression in T cells from experiments identical to those described in FIG. 4D. FIG. 4F shows IFNγ production in PEBL- or mock-transduced T cells, electroporated with or without anti-CD19 CAR mRNA, and co-cultured with OP-1 for 6 hours at E:T 1:1. Bars represent mean (±SD) of triplicate experiments. *, P<0.001; **, P<0.0001.

FIG. 5A-FIG. 5F show T cells with downregulated CD7 by PEBL acquire powerful cytotoxicity against CD7+ leukemic cells after expression of anti-CD7 CAR. Cytotoxicity of anti-CD7 PEBL-transduced T-cells electroporated with or without anti-CD7 CAR mRNA against CD7+ cell lines (FIG. 5A). Shown are data for 4-hour assays at 1:1 E:T. Symbols indicate the mean of 3 measurements each with T cells from 4 donors for MOLT-4, CCRF-CEM and Jurkat, and 5 donors for Loucy and KG1a (P<0.001 for each comparison). Cytotoxicity of anti-CD7 PEBL-transduced T-cells electroporated with or without anti-CD7 CAR mRNA against primary leukemic cells from patients with T-ALL (FIG. 5B). Shown are data for 4-hour assays at the indicated E:T. Symbols refer to mean (±SD) of 3 measurements. FIG. 5C shows overall specific cytotoxicity of T-cells transduced with either anti-CD7 PEBL or GFP alone ("Mock"), after electroporation with anti-CD7 CAR mRNA against the 5 CD7+ cell lines. T cells from 3 donors were tested, at 1:1 E:T, in 4-hour assays. Each symbol represents specific percent cytotoxicity against CD7+ cell line, after subtraction of the percent cytotoxicity obtained with the same T cells electroporated without mRNA. Horizontal bars indicate the median for each group. Anti-CD7 PEBL- or mock-transduced T-cells from 3 donors were electroporated with or without anti-CD7 CAR mRNA (FIG. 5D). Cytotoxicity against MOLT-4 was tested at 1:1 E:T in 4-hour assays. Shown is the mean fluorescence intensity (MFI) of anti-CD107a-PE (H4A3; BD Biosciences). Bars represent mean (±SD) of triplicate experiments. Anti-CD7 PEBL-transduced T-cells were retrovirally transduced with either anti-CD7 CAR or mock-transduced, and tested against primary leukemic cells from patients with T-ALL (FIG. 5E). Each symbol represent mean (±SD) of triplicate experiments. Mock- or PEBL-transduced T-cells, sequentially transduced with or without anti-CD7 CAR, were cultured alone or in presence of Streck-treated MOLT-4 cells, added weekly and 120 IU/mL IL-2 (FIG. 5F). Symbols indicate mean (±SD) percentage of cell recovery relative to number of input cells in triplicate cultures. , P<0.01; *, P<0.001; ****, P<0.0001.

FIG. 6C shows leukemia cell growth in mice shown in FIG. 6A and FIG. 6B expressed as photons per second. Each symbol corresponds to bioluminescence measurements in each mouse, normalised to the average of ventral plus dorsal signals in all mice before CAR-T cell infusion. Kaplan-Meier curves show overall survival of mice in the different groups (8 in each group) (FIG. 6D). Mice were euthanized when the total bioluminescence signal reached $1\times10^{10}$ photons per second. P values calculated by log-rank test.

FIG. 7A-FIG. 7E show PEBL-CAR-T cell activity against ETP-ALL in a patient-derived xenograft (PDX) model. Primary ETP-ALL cells, previously propagated in NOD-SCID-IL2RGnull mice, were infused intravenously (i.v.) in 10 NOD-SCID-IL2RGnull mice at $2\times10^6$ cells per mouse (FIG. 7A). Five mice ("Controls") were left untreated. The remaining 5 mice received a single i.v. infusion of PEBL-CAR T cells ($2\times10^7$ in PEBL-CAR #1, $2\times10^6$ in the remaining 4 mice) at the indicated time point (grey arrow), as well as 20,000 IU IL-2 i.p. every two days; IL-2 was also administered to 2 of the 5 control mice. Black symbols (left y axes) indicate the number of ETP-ALL cells/mL counted in peripheral blood. Grey symbols (right y axes) show numbers of PEBL-CAR T cells. Mice were euthanized when the percentage of ETP-ALL cells among blood mononucleated cells reached ≥80%. Percentage of ETP-ALL (denominator, total human plus mouse CD45+ cells) in various organs of the 5 untreated mice (FIG. 7B). Blood smears of treated (PEBL-CAR #1) and untreated ETP-ALL 7 days after infusion of T cells; smudge cells were prominent in blood after PEBL-CAR T cells (FIG. 7C). Flow cytometric dot plots show the presence of CD7+ CD3− ETP-ALL cells in the tissues of an untreated control mouse with ETP-ALL and of CD7− CD3+ PEBL-CAR T cells in the PEBL-CAR #1 mouse treated with PEBL-CAR-T cells (FIG. 7D). No ETP-ALL (<0.01%) was detected in the treated mouse. Events shown were normalized to the events acquired for the corresponding plots shown in the control mouse. Spleen of treated (PEBL-CAR #1) and untreated mice (FIG. 7E).

FIG. 8A-FIG. 8C show specificity and function of the anti-CD7-41BB-CD3ζCAR. OP-1 (CD7−) and MOLT-4 (CD7+) were incubated with supernatant collected from Jurkat cells transduced with anti-CD7 scFv, or transduced with a vector containing GFP only ("Control") (FIG. 8A). After washing, cells were incubated with biotin-conjugated goat anti-mouse F(ab')2 antibody followed by streptavidin-APC (Jackson ImmunoResearch). Flow cytometric histograms illustrate binding of the anti-CD7 scFv to MOLT-4 but not OP-1. Jurkat cells were transduced with anti-CD7-41BB-CD3ζCAR, anti-CD19-41BB-CD3ζCAR, or a vector containing GFP alone (FIG. 8B). These cells were co-cultured at 1:1 E:T with the CD7+ MOLT-4 or CCRF-CEM cells, or with the CD7− cells OP-1. Target cells were labelled with calcein red-orange AM (Invitrogen). After 30 minutes incubation, the percentage of cell doublets was measured by flow cytometry. Bars illustrate mean (±SD) of triplicate measurements. FIG. 8C shows that CAR-mediated cell aggregation is inhibited by pre-incubating target cells with a soluble form of the anti-CD7 scFv. ***P<0.001.

FIG. 9A provides representative flow cytometric dot plots of T lymphocytes activated for 7 days with Dynabeads Human T-Activator CD3/CD28 (ThermoFisher Scientific) and IL-2, and transduced with the anti-CD7 CAR. Flow cytometric dot plots illustrate GFP fluorescence and CAR expression, the latter revealed by staining with biotin-conjugated goat anti-mouse F(ab')2 antibody followed by streptavidin-APC (Jackson ImmunoResearch). FIG. 9B shows Western blot analysis of CAR expression. Cell lysates of mock- and CAR-transduced T cells were separated on a 10% polyacrylamide gel under reducing or non-reducing conditions. The blotted membrane was probed with a mouse anti-human CD3ζ antibody (8D3; BD Biosciences) followed by goat anti-mouse IgG conjugated to horseradish peroxidase (R&D Systems). Antibody binding was revealed with Clarity Western ECL Substrate (Bio-Rad).

FIG. 10B shows RT-PCR analysis of CD7 mRNA expression. cDNA derived from total mRNA extracted from Jurkat cells transduced with PEBL1-3, GFP alone ("mock"), or untransduced ("WT") was used as template. CD7 cDNA (723 bp) was amplified with the following primers: Forward, ATGGCCGGGCCTCCG (SEQ ID NO:38), Reverse, TCACTGGTACTGGTTGGG (SEQ ID NO:39). Electrophoresis was performed on a 1% agarose gel with SYBR Safe Gel Stain (ThermoFisher). No template control is also shown. A 87 bp (676-762th nucleotide) region of glyceraldehyde 3-phosphate dehydrogenase (GAPDH) was amplified in parallel as a control.

FIG. 13A shows expression of anti-CD19 and anti-CD7 CARs (in an mCherry-containing vector) in peripheral blood T cells previously transduced with anti-CD7 PEBL. Flow cytometry dot plots illustrate mCherry expression and staining of T cells with biotin-conjugated goat anti-mouse F(ab')2 antibody followed by streptavidin conjugated to allophycocyanin (Jackson ImmunoResearch). Results with T cell transduced with a vector containing mCherry alone ("Mock") are also shown. Expression of CD19 in CCRF-CEM and Jurkat cells transduced with a vector containing CD19 and GFP (FIG. 13B). CD19 was detected with anti-CD19 APC (Miltenyi Biotech). Four-hour cytotoxicity assays targeting CD19+ CCRF-CEM or CD19+ Jurkat cells with anti-CD19 or anti-CD7 PEBL-CAR-T cells at different E:T ratios (FIG. 13C). Symbols indicate mean (±SD) of triplicate measurements. P<0.001 for data with either CAR versus mock-transduced T cells at all E:T ratios. Long-term cytotoxicity of anti-CD19 or anti-CD7 PEBL-CAR-T cells at different E:T ratios as measured by live cell image analysis with IncuCyte Zoom System (Essen BioScience) (FIG. 13D). Symbols indicate mean (±SD) of 3 measurements of CD19+ CCRF-CEM (top) or CD19+ Jurkat cells (bottom) in wells containing CAR-T cells, mock-transduced T cells, or no T cells. Measurements were performed at 4-hour intervals. Proliferative capacity of anti-CD19 and anti-CD7 PEBL-CAR-T cells with and without co-culture with CD19+ Jurkat cells (FIG. 13E). Anti-CD7 PEBL-transduced T-cells, sequentially transduced with anti-CD19 or anti-CD7 CARs or mCherry alone, were cultured alone or in presence of irradiated CD19+ Jurkat cells, added weekly and 120 IU/mL IL-2. Symbols indicate mean (±SD) percentage of cell recovery relative to number of input cells in triplicate cultures.

FIG. 15A and FIG. 15B illustrate PEBL-transduced T cells expressing anti-CD7-41BB-CD3ζ CAR exerted antitumor activity in mouse models and remained active against cells collected at relapse. FIG. 15A shows percentage of CCRF-CEM cells among white blood cells in blood from NOD-SCID-IL2RGnull mice infused i.v. with CCRF-CEM cells labelled with luciferase and then treated intravenously with either PEBL-CAR-transduced T-cells, mock-transduced T-cells, or RPMI-1640 instead of cells ("Control"), as described for FIG. 6C. For "Control" and "Mock", blood was obtained from euthanized mice that had reached bioluminescence threshold of $10^{10}$ photons/second 17-23 days after leukemia cells infusion. For PEBL-CAR mice, blood was obtained via cheek prick on day 24 after CCRF-CEM infusion. CCRF-CEM cells collected at relapse from the spleen and liver of mice treated with PEBL-CAR were cultured for 2 days (FIG. 15B). They were then used as targets in 4-hour cytotoxicity assay at E:T 1:1 using PEBL-CAR- or mock-transduced T-cells originally used for infusion. Comparison was also made with the same batch of CCRF-CEM-expressing luciferase cells used to generate the xenograft. Percentage cytotoxicity was determined from plate measurements of bioluminescence signal after addition of BrightGlo luciferase assay system (Promega). Bars show mean (±SD) of triplicate measurements; each white and grey bar corresponds to cells from one mouse.

FIG. 17 provides a scheme of an exemplary embodiment of the present invention.

DETAILED DESCRIPTION OF THE INVENTION

Figure 1A:
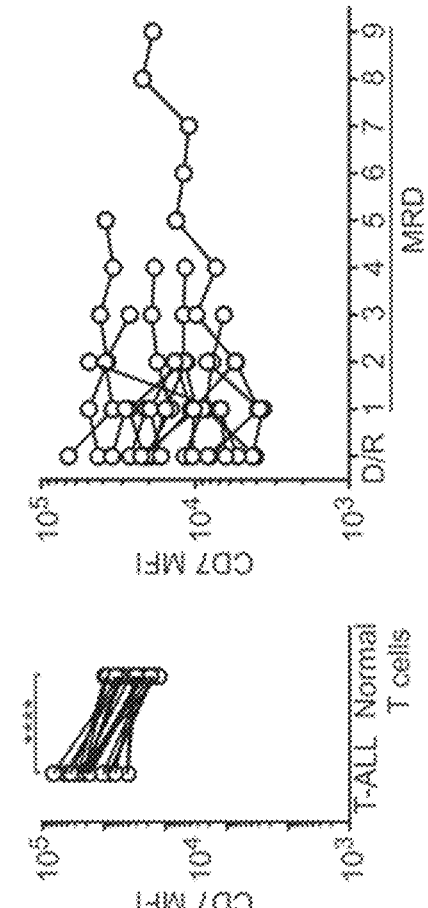
FIG. 1A-FIG. 1D illustrate CD7 expression in T-ALL. Percentage of ALL cells expressing CD7 at diagnosis, relapse and during chemotherapy (MRD); the number of bone marrow samples studied at each stage is shown (FIG. 1A). CD7 mean fluorescence intensity (MFI) in T-ALL cells and residual normal T-cells from the same samples (n=19; P<0.0001 by paired t test) (FIG. 1B). CD7 MFI in T-ALL cells at diagnosis or relapse ("D/R") and in follow-up bone marrow samples with MRD (n=18) (FIG. 1C). Flow cytometric contour plots illustrate CD7 expression in T-ALL cells (CD3-negative) and normal T cells (CD3-positive) at diagnosis, MRD, and relapse in one representative patient (FIG. 1D).

A description of example embodiments of the invention follows.

The present invention is based, in part, on the design of a chimeric antigen receptor (CAR) that is directed against CD7, a 40 kDa type I transmembrane glycoprotein which is the primary marker for T cell malignancies, and which is highly expressed in all cases of T cell ALL, including early T-cell progenitor acute lymphoblastic leukemia (ETP-ALL). As described herein, the anti-CD7 CAR induces T cells to exert specific cytotoxicity against T cell malignancies. Further, T cell cytotoxicity was shown to be markedly increased when anti-CD7 CAR was used in combination with down-regulation of CD7 expression on the effector T cells. As demonstrated herein, downregulation (e.g., elimination, reduction, and/or relocalization) of CD7 prevented the fratricidal effect exerted by the corresponding anti-CD7 CAR, allowing greater T cell recovery after CAR expression as compared to cells that retained the target antigen (e.g., CD7), and a more effective cytotoxicity against T leukemia/lymphoma cells.

Accordingly, in one aspect, the present invention relates to an engineered immune cell comprising a nucleic acid that comprises a nucleotide sequence encoding a chimeric antigen receptor (CAR), wherein the CAR comprises intracellular signaling domains of 4-1BB and CD3ζ, and an antibody that specifically binds Cluster of Differentiation 7 (CD7). The CAR of the present invention is sometimes referred to herein as "anti-CD7-41BB-CD3ζ". An exemplary embodiment is depicted in FIG. 17.

As used herein, an "engineered" immune cell includes an immune cell that has been genetically modified as compared to a naturally-occurring immune cell. For example, an engineered T cell produced according to the present methods carries a nucleic acid comprising a nucleotide sequence that does not naturally occur in a T cell from which it was derived.

In certain embodiments, the engineered immune cell is an engineered T cell, an engineered natural killer (NK) cell, an engineered NK/T cell, an engineered monocyte, an engineered macrophage, or an engineered dendritic cell. In certain embodiments, the engineered immune cell is an engineered T cell. As used herein, the term "nucleic acid" refers to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In certain embodiments, nucleic acid molecules can be modified. In the case of a double-stranded polymer, "nucleic acid" can refer to either or both strands of the molecule.

The term "nucleotide sequence," in reference to a nucleic acid, refers to a contiguous series of nucleotides that are joined by covalent linkages, such as phosphorus linkages (e.g., phosphodiester, alkyl and aryl-phosphonate, phosphorothioate, phosphotriester bonds), and/or non-phosphorus linkages (e.g., peptide and/or sulfamate bonds). In certain embodiments, the nucleotide sequence encoding, e.g., a target-binding molecule linked to a localizing domain is a heterologous sequence (e.g., a gene that is of a different species or cell type origin).

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As will be appreciated by those of skill in the art, in some aspects, the nucleic acid further comprises a plasmid sequence. The plasmid sequence can include, for example, one or more sequences of a promoter sequence, a selection marker sequence, or a locus-targeting sequence.

As used herein, "antibody" means an intact antibody or antigen-binding fragment of an antibody, including an intact antibody or antigen-binding fragment that has been modified or engineered, or that is a human antibody. Examples of antibodies that have been modified or engineered are chimeric antibodies, humanized antibodies, multiparatopic antibodies (e.g., biparatopic antibodies), and multispecific antibodies (e.g., bispecific antibodies). Examples of antigen-binding fragments include Fab, Fab', F(ab')$_2$, Fv, single chain antibodies (e.g., scFv), minibodies and diabodies.

The term "specifically (or selectively) binds" or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

In certain embodiments, the antibody that binds CD7 is a single-chain variable fragment antibody ("scFv antibody"). scFv refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun (1994) *The Pharmacology Of Monoclonal Antibodies*, vol. 113, Rosenburg and Moore eds. Springer-Verlag, New York, pp. 269-315. See also, PCT Publication No. WO 88/01649 and U.S. Pat. Nos. 4,946,778 and 5,260,203. As would be appreciated by those of skill in the art, various suitable linkers can be designed and tested for optimal function, as provided in the art, and as disclosed herein.

In certain embodiments, the anti-CD7 scFv comprises a variable heavy chain (heavy chain variable region or VH) and a variable light chain (light chain variable region or VL) having an amino acid sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 1 and 2, respectively. The heavy chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH sequence of SEQ ID NO:1. The light chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VL sequence of SEQ ID NO:2. In some instances, the heavy chain variable region comprise at least one (e.g., 1, 2, 3, 4, 5, 6, 7, 8, 9, 10, or more) amino acid substitution in the sequence set forth in SEQ ID NO:1. In certain instances, the heavy chain variable region comprise 10 or fewer amino acid (e.g., 0, 1, 2, 3, 4, 5, 6, 7, 8, 9, or 10) substitutions in the sequence set forth in SEQ ID NO:1. In some instances, the light chain variable region comprise at least one (e.g., 1, 2, 3, 4, 5, 6, 7, 8, 9, 10, or more) amino acid substitution in the sequence set forth in SEQ ID NO:2. In certain instances, the light chain variable region comprise 10 or fewer amino acid (e.g., 0, 1, 2, 3, 4, 5, 6, 7, 8, 9, or 10) substitutions in the sequence set forth in SEQ ID NO:2. In some embodiments, a nucleic acid sequence encoding a VH comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:23. In other embodiments, a nucleic acid sequence encoding a VL comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:24.

In certain embodiments, the anti-CD7 scFv comprises a variable heavy chain (heavy chain variable region or VH) and a variable light chain (light chain variable region or VL) having a sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 14 and 15, respectively. The heavy chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH sequence of SEQ ID NO:14. The light chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VL sequence of SEQ ID NO:15.

In some instances, the heavy chain variable region comprise at least one (e.g., 1, 2, 3, 4, 5, 6, 7, 8, 9, 10, or more) amino acid substitution in the sequence set forth in SEQ ID NO:14. In certain instances, the heavy chain variable region comprise 10 or fewer amino acid (e.g., 0, 1, 2, 3, 4, 5, 6, 7, 8, 9, 10) substitutions in the sequence set forth in SEQ ID NO:14. In some cases, the light chain variable region comprise at least one (e.g., 1, 2, 3, 4, 5, 6, 7, 8, 9, or more) amino acid substitution in the sequence set forth in SEQ ID NO:15. In certain cases, the heavy chain variable region comprise 10 or fewer amino acid (e.g., 0, 1, 2, 3, 4, 5, 6, 7, 8, 9, 10) substitutions in the sequence set forth in SEQ ID NO:15.

In some embodiments, a nucleic acid sequence encoding a VH comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:25. In other embodiments, a nucleic acid sequence encoding a VL comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:26.

In certain embodiments, the anti-CD7 scFv comprises a variable heavy chain (heavy chain variable region or VH) and a variable light chain (light chain variable region or VL) having a sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 16 and 17, respectively. The heavy chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH sequence of SEQ ID NO:16. The light chain variable region can comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VL sequence of SEQ ID NO:17.

In some instances, the heavy chain variable region comprise at least one (e.g., 1, 2, 3, 4, 5, 6, 7, 8, 9, 10, or more) amino acid substitution in the sequence set forth in SEQ ID NO:16. In certain instances, the heavy chain variable region comprise 13 or fewer amino acid (e.g., 0, 1, 2, 3, 4, 5, 6, 7, 8, 9, 10, 11, 12, or 13) substitutions in the sequence set forth in SEQ ID NO:16. In some cases, the light chain variable region comprise at least one (e.g., 1, 2, 3, 4, 5, 6, 7, 8, 9, 10, or more) amino acid substitution in the sequence set forth in SEQ ID NO:17. In certain cases, the heavy chain variable region comprise 5 or fewer amino acid (e.g., 0, 1, 2, 3, 4, 5, 6, 7, 8, 9, 10, or 11) substitutions in the sequence set forth in SEQ ID NO:17. In some embodiments, a nucleic acid sequence encoding a VH comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:27. In other embodiments, a nucleic acid sequence encoding a VL comprises at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to the nucleic acid sequence set forth in SEQ ID NO:28.

In some embodiments, the scFv of the present invention comprises a variable heavy chain sequence having at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to a variable heavy chain sequence of an anti-CD7 antibody. In some embodiments, the scFv of the present invention comprises a variable light chain sequence having at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to a variable light chain sequence of an anti-CD7 antibody. For instance, the anti-CD7 antibody can be any such recognized by one skilled in the art.

TABLE 1

Amino acid sequences of VH regions and VL regions of anti-CD7 scFvs

| | Component | Amino Acid Sequence |
|---|---|---|
| TH69 | VH | EVQLVESGGGLVKPGGSLKLSCAASGLTFSS YAMSWVRQTPEKRLEWVASISSGGFTYYPDS VKGRFTISRDNARNILYLQMSSLRSEDTAMY YCARDEVRGYLDVWGAGTTVTVSS (SEQ ID NO: 1) |
| | VL | AAYKDIQMTQTTSSLSASLGDRVTISCSASQ GISNYLNWYQQKPDGTVKLLIYYTSSLHSGV PSRFSGSGSGTDYSLTISNLEPEDIATYYCQ QYSKLPYTFGGGTKLEIKR (SEQ ID NO: 2) |
| 3a1f | VH | QVQLQESGAELVKPGASVKLSCKASGYTFTS YWMHWVKQRPGQGLEWIGKINPSNGRTNYNE KFKSKATLTVDKSSSTAYMQLSSLTSEDSAV YYCARGGVYYDLYYYALDYWGQGTTVTVSS (SEQ ID NO: 14) |
| | VL | DIELTQSPATLSVTPGDSVSLSCRASQSISN NLHWYQQKSHESPRLLIKSASQSISGIPSRF SGSGSGTDFTLSINSVETEDFGMYFCQQSNS WPYTFGGGTKLEIKR (SEQ ID NO: 15) |
| T3-3A1 | VH | DVQLVESGGGLVQPGGSRKLSCAASGFTFSS FGMHWVRQAPEKGLEWVAYISSGSSTLHYAD TVKGRFTISRDNPKNTLFLQMTSLRSEDTAM YYCARWGNYPHYAMDYWGQGTSVTVSS (SEQ ID NO: 16) |
| | VL | DIVMTQSPASLAVSLGQRATISCRASKSVSA SGYSYMHWYQQKPGQPPKLLIYLASNLESGV PARFSGSGSGTDFTLNIHPVEEEDAVTYYCQ HSRELPYTFGGGTKLEIK (SEQ ID NO: 17) |

TABLE 2

Nucleic acid sequences of VH regions and VL regions of anti-CD7 scFvs

| | Component | Nucleic Acid Sequence |
|---|---|---|
| TH69 | VH | GAGGTGCAGCTGGTCGAATCTGGAGGAGG ACTGGTGAAGCCAGGAGGATCTCTGAAAC TGAGTTGTGCCGCTTCAGGCCTGACCTTC TCAAGCTACGCCATGAGCTGGGTGCGACA GACACCTGAGAAGCGGCTGGAATGGGTCG CTAGCATCTCCTCTGGCGGGTTCACATAC |

TABLE 2-continued

Nucleic acid sequences of VH regions
and VL regions of anti-CD7 scFvs

| | Component | Nucleic Acid Sequence |
|---|---|---|
| | | TATCCAGACTCCGTGAAAGGCAGATTTAC<br>TATCTCTCGGGATAACGCAAGAAATATTC<br>TGTACCTGCAGATGAGTTCACTGAGGAGC<br>GAGGACACCGCAATGTACTATTGTGCCAG<br>GGACGAAGTGCGCGGCTATCTGGATGTCT<br>GGGGAGCTGGCACTACCGTCACCGTCTCC<br>AGC (SEQ ID NO: 23) |
| | VL | GCCGCATACAAGGATATTCAGATGACTCA<br>GACCACAAGCTCCCTGAGCGCCTCCCTGG<br>GAGACCGAGTGACAATCTCTTGCAGTGCA<br>TCACAGGGAATTAGCAACTACCTGAATTG<br>GTATCAGCAGAAGCCAGATGGCACTGTGA<br>AACTGCTGATCTACTATACCTCTAGTCTG<br>CACAGTGGGGTCCCCTCACGATTCAGCGG<br>ATCCGGCTCTGGGACAGACTACAGCCTGA<br>CTATCTCCAACCTGGAGCCCGAAGATATT<br>GCCACCTACTATTGCCAGCAGTACTCCAA<br>GCTGCCTTATACCTTTGGCGGGGAACAA<br>AGCTGGAGATTAAAAGG<br>(SEQ ID NO: 24) |
| 3a1f | VH | CAGGTCCAGCTGCAGGAGTCAGGAGCTGA<br>GCTGGTGAAGCCAGGGGCAAGCGTCAAAC<br>TGTCCTGCAAGGCCTCTGGATATACATTC<br>ACTAGCTACTGGATGCACTGGGTGAAACA<br>GAGACCCGGACAGGGCCTGGAGTGGATCG<br>GAAAGATTAACCCTAGCAATGGCAGGACC<br>AACTACAACGAAAAGTTTAAATCCAAGGC<br>AACCCTGACAGTGGACAAGAGCTCCTCTA<br>CAGCCTACATGCAGCTGAGTTCACTGACT<br>TCAGAGGATAGCGCAGTGTACTATTGCGC<br>CAGAGGCGGGGTCTACTATGACCTGTACT<br>ATTACGCCCTGGATTATTGGGGGCAGGGA<br>ACCACAGTGACTGTCAGCTCC<br>(SEQ ID NO: 25) |
| | VL | GACATCGAGCTGACCCAGAGTCCTGCTAC<br>ACTGAGCGTGACTCCAGGCGATTCTGTCA<br>GTCTGTCATGTCGGGCAAGCCAGTCCATC<br>TCTAACAATCTGCACTGGTACCAGCAGAA<br>ATCCCATGAATCTCCACGACTGCTGATTA<br>AGAGTGCCTCACAGAGCATCTCCGGCATT<br>CCCTCCCGGTTCTCTGGCAGTGGGTCAGG<br>AACTGACTTTACCCTGAGTATTAACTCAG<br>TGGAGACAGAAGATTTCGGCATGTATTTT<br>TGCCAGCAGAGCAATTCCTGGCCCTACAC<br>TTTCGGAGGCGGGACCAAACTGGAGATCA<br>AGCGG (SEQ ID NO: 26) |
| T3-<br>3A1 | VH | GATGTGCAGCTGGTGGAGTCTGGGGGAGG<br>CTTAGTGCAGCCTGGAGGGTCCCGGAAAC<br>TCTCCTGTGCAGCCTCTGGATTCACTTTC<br>AGTAGCTTTGGAATGCACTGGGTTCGTCA<br>GGCTCCAGAGAAGGGGCTGGAGTGGGTCG<br>CATACATTAGTAGTGGCAGTAGTACCCTC<br>CACTATGCAGACACAGTGAAGGGCCGATT<br>CACCATCTCCAGAGACAATCCCAAGAACA<br>CCCTGTTCCTGCAAATGACCAGTCTAAGG<br>TCTGAGGACACGGCCATGTATTACTGTGC<br>AAGATGGGGTAACTACCCTCACTATGCTA<br>TGGACTACTGGGGTCAAGGAACCTCAGTC<br>ACCGTCTCCTCA (SEQ ID NO: 27) |
| | VL | GACATTGTGATGACCCAGTCTCCTGCTTC<br>CTTAGCTGTATCTCTGGGGCAGAGGGCCA<br>CCATCTCATGCAGGGCCAGCAAAAGTGTC<br>AGTGCATCTGGCTATAGTTATATGCACTG<br>GTACCAACAGAAACCAGGACAGCCACCCA<br>AACTCCTCATCTATCTTGCATCCAACCTA<br>GAATCTGGGTCCCTGCCAGGTTCAGTGG<br>CAGTGGGTCTGGGACAGACTTCACCCTCA<br>ACATCCATCCTGTGGAGGAGGAGGATGCT<br>GTAACCTATTACTGTCAGCACAGTAGGGA<br>GCTTCCGTACACGTTCGGAGGGGGGACCA<br>AGCTGGAAATAAAA<br>(SEQ ID NO: 28) |

The term "sequence identity" means that two nucleotide sequences or two amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

As those skilled in the art would appreciate, in certain embodiments, any of the sequences of the various components disclosed herein (e.g., scFv, intracellular signaling domain, hinge, linker, localizing sequences, and combinations thereof) can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the specific corresponding sequences disclosed herein. For example, in certain embodiments, the intracellular signaling domain 4-1BB can have at least 90% sequence identity, at least 91% sequence identity, at least 92% sequence identity, at least 93% sequence identity, at least 94% sequence identity, at least 95% sequence identity, at least 95% sequence identity, at least 96% sequence identity, at least 97% sequence identity, at least 98% sequence identity, at least 99% sequence identity, or 100% sequence identity to SEQ ID NO:3, as long as it possesses the desired function. In certain embodiments, the intracellular signaling domain of 4-1BB comprises the sequence set forth in SEQ ID NO:3 (KRGRKKLLY-IFKQPFMRPVQTTQEEDGCSCRFPEEEEGGCEL).

As another example, in certain embodiments, the intracellular signaling domain 4-1BB can be replaced by another intracellular signaling domain from a co-stimulatory molecule such as CD28, OX40, ICOS, CD27, GITR, HVEM, TIM1, LFA1, or CD2. In some embodiments, the intracellular signaling domain of the CAR can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the intracellular signaling domain of CD28, OX40, ICOS, CD27, GITR, HVEM, TIM1, LFA1, or CD2.

As another example, in certain instances, the intracellular signaling domain of 4-1BB can also include another intracellular signaling domain (or a portion thereof) from a co-stimulatory molecule such as CD28, OX40, ICOS, CD27, GITR, HVEM, TIM1, LFA1, or CD2. In some embodiments, the additional intracellular signaling domain can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the intracellular signaling domain of CD28, OX40, ICOS, CD27, GITR, HVEM, TIM1, LFA1, or CD2. In other embodiments, the additional intracellular signaling domain comprises at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to one or more intracellular signaling domain fragment(s) of CD28, OX40, ICOS, CD27, GITR, HVEM, TIM1, LFA1, or CD2.

As another example, in certain embodiments, the intracellular signaling domain CD3 can have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to SEQ ID NO:4, as long as it possesses the desired function. In certain embodiments, the intracellular signaling domain of CD3ζ comprises the sequence set forth in SEQ ID NO:4 (RVKFSRSADAPAYQQGQNQLYNELNLGRREEY-DVLDKRRGRDPEMGGKPRRKNPQE GLYNELQKDK-MAEAYSEIGMKGERRRGKGHDGLYQGLSTATKDTY-DALHMQALPPR).

In some instances, the intracellular signaling domain comprises an immunoreceptor tyrosine-based activation motif (ITAM) or a portion thereof, as long as it possess the desired function. The intracellular signaling domain of the CAR can include a sequence having at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to an ITAM. In certain embodiments, the intracellular signaling domain can have at least 95% sequence identity, at least 96% sequence identity, at least 97% sequence identity, at least 98% sequence identity, at least 99% sequence identity, or 100% sequence identity to FcεRIγ, CD4, CD7, CD8, CD28, OX40 or H2-Kb, as long as it possesses the desired function.

In certain embodiments, the anti-CD7 CAR further comprises a hinge and transmembrane sequence. Hinge and transmembrane sequences suitable for use in the present invention are known in the art, and provided in, e.g., publication WO2016/126213, incorporated by reference in its entirety. In certain embodiments, the hinge sequence comprises the sequence set forth in SEQ ID NO:5 (TTTPA-PRPPTPAPTIASQPLSLRPEACRPAAGGAVHTRGLD-FACD). In certain embodiments, the transmembrane sequence comprises the sequence set forth in SEQ ID NO:6 (IYIWAPLAGTCGVLLLSLVITLYC). In some embodiments, the hinge and transmembrane domain of the anti-CD7 CAR can be include a signaling domain (e.g., transmembrane domain) from CD8β, 4-1BB, CD28, CD34, CD4, FcεRIγ, CD16, OX40, CD3ζ, CD3ε, CD3γ, CD3δ, TCRα, CD32, CD64, VEGFR2, FAS, FGFR2B, or another transmembrane protein.

In certain embodiments, the anti-CD7 CAR further comprises a CD8a signal peptide (MALPVTALLLPLALLL-HAARP; SEQ ID NO:7). A schematic of the anti-CD7 CAR comprising the embodiments described herein is shown in FIG. 17.

In certain aspects of the present invention, the chimeric antigen receptor (CAR) can bind to a molecule that is expressed on the surface of a cell including, but not limited to members of the CD1 family of glycoproteins, CD2, CD3ζ, CD4, CD5, CD7, CD8, CD25, CD28, CD30, CD38, CD45, CD45RA, CD45RO, CD52, CD56, CD57, CD99, CD127, and CD137.

As described herein, T cell cytotoxicity was shown to be markedly increased when anti-CD7 CAR was used in combination with downregulation of CD7 expression on the effector T cells. As demonstrated herein, downregulation (e.g., elimination, reduction, and/or relocalization) of CD7 prevented the fratricidal effect exerted by the corresponding anti-CD7 CAR, allowing greater T cell recovery after CAR expression as compared to cells that retained the target antigen (e.g., CD7), and a more effective cytotoxicity against T leukemia/lymphoma cells. As those of skill in the art would appreciate, downregulation of CD7 expression on the effector T cells can be achieved according to a variety of known methods including, for example, "intrabodies" against CD7 (as described in WO2016/126213), RNAi against CD7, or gene editing methods such as, e.g., meganucleases, TALEN, CRISPR/Cas9, and zinc finger nucleases.

In certain embodiments, the engineered immune cell further comprises a nucleic acid that comprises a nucleotide sequence encoding a target-binding molecule linked to a localizing domain. The "target-binding molecule linked to a localizing domain" is sometimes referred to herein as a protein expression blocker (PEBL) or in some cases, an "intrabody", as described in WO2016/126213, the teachings of which are incorporated by reference in their entirety. Exemplary embodiments of a PEBL are shown in FIG. 3E and FIG. 17.

As used herein, "linked" in the context of the protein expression blocker refers to a gene encoding a target-binding molecule directly in frame (e.g., without a linker) adjacent to one or more genes encoding one or more localizing domains. Alternatively, the gene encoding a target-binding molecule may be connected to one or more gene encoding one or more localizing domains through a linker sequence, e.g., as described in WO2016/126213. As would be appreciated by those of skill in the art, such linker sequences as well as variants of such linker sequences are known in the art. Methods of designing constructs that incorporate linker sequences as well as methods of assessing functionality are readily available to those of skill in the art.

In certain embodiments, the target-binding molecule is an antibody that binds CD7. In certain embodiments, the antibody is a scFv. In certain embodiments, the scFv comprises a VH sequence set forth in SEQ ID NO:1 and a VL sequence set forth in SEQ ID NO:2. In certain embodiments, the scFv comprises a VH sequence set forth in SEQ ID NO:14 and a VL sequence set forth in SEQ ID NO:15. In certain embodiments, the scFv comprises a VH sequence set forth in SEQ ID NO:16 and a VL sequence set forth in SEQ ID NO:17. As described herein, in certain embodiments, the scFv comprises a VH and a VL having sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 1 and 2, respectively; SEQ ID NO:14 and SEQ ID NO:15, respectively; or SEQ ID NO:16 and SEQ ID NO:17, respectively.

In some embodiments, the nucleic acid sequence of SEQ ID NO:23 encoding an immunoglobulin heavy chain variable region of an anti-CD7 scFv and the nucleic acid sequence of SEQ ID NO:24 encoding an immunoglobulin light chain variable region of an anti-CD7 scFv is used to produce an anti-CD7 protein expression blocker. In other embodiments, the nucleic acid sequence of SEQ ID NO:25 encoding an immunoglobulin heavy chain variable region of an anti-CD7 scFv and the nucleic acid sequence of SEQ ID NO:26 encoding an immunoglobulin light chain variable region of an anti-CD7 scFv is used to produce an anti-CD7 protein expression blocker. In certain embodiments, the nucleic acid sequence of SEQ ID NO:27 encoding an immunoglobulin heavy chain variable region of an anti-CD7 scFv and the nucleic acid sequence of SEQ ID NO:28 encoding an immunoglobulin light chain variable region of an anti-CD7 scFv is used to produce an anti-CD7 protein expression blocker.

In certain embodiments, the antibody that binds CD7 in the context of the CAR, as described herein, can be different from the antibody that binds CD7 in the context of the target-binding molecule (the PEBL). Merely to illustrate, the antibody that binds CD7 in the context of the CAR can comprise a VH sequence set forth in SEQ ID NO:1 and a VL sequence set forth in SEQ ID NO:2, whereas the antibody that binds CD7 in the context of the PEBL can comprise a VH sequence set forth in SEQ ID NO:14 and a VL sequence set forth in SEQ ID NO:15. In certain embodiments, the antibody that binds CD7 in the context of the CAR, as described herein, can be the same as the antibody that binds CD7 in the context of the target-binding molecule (the PEBL).

In certain embodiments, the localizing domain of the PEBL comprises an endoplasmic reticulum (ER) or Golgi retention sequence; a proteosome localizing sequence; a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B. In certain embodiments, the localizing domain comprises endoplasmic reticulum (ER) retention peptides EQKLISEEDLKDEL (SEQ ID NO:8), (GGGGS)$_4$AEKDEL (SEQ ID NO:9), or CD8α hinge and transmembrane domain (TTTPAPRPPTPAPTIASQPLSLRPEACRPAAGGAVHTRGLDFACDIYIWAPLAGTCGVLL LSLVITLY) (SEQ ID NO:10) followed by KYKSRRSFIDEKKMP (SEQ ID NO:11), as described herein. The localizing domain can direct the PEBL to a specific cellular compartment, such as the Golgi or endoplasmic reticulum, the proteasome, or the cell membrane, depending on the application. The ER or Golgi retention sequence comprises the amino acid sequence KDEL (SEQ ID NO:18); KKXX where X is any amino acid; KXD/E (such as KXD or KXE) where X is any amino acid; or YQRL (SEQ ID NO:21). The proteasome localizing sequence can comprise a PEST (SEQ ID NO:22) motif.

In some embodiments, proteasome localization is achieved by linking the scFv sequence to a tripartite motif containing 21 (TRIM21) targeting domain sequence and coexpressing the sequence encoding the human TRIM21 E3 ubiquitin ligase protein. TRIM21 binds with high affinity to the Fc domains of antibodies and can recruit the ubiquitin-proteosome complex to degrade molecules (e.g., proteins and peptides) bound to the antibodies. The TRIM21 targeting domain sequence encodes amino acid sequences selected from the group of human immunoglobulin G (IgG) constant regions (Fc) genes such as IgG1, IgG2, or IgG4 and is used to form a fusion protein comprising scFv and Fc domains. In this embodiment, the exogenously expressed TRIM21 protein binds the scFv-Fc fusion protein bound to the target protein (e.g., CD7) and directs the complex to the proteasome for degradation.

Details of the amino acid sequence of the human TRIM21 E3 ligase protein can be found, for example, in NCBI Protein database under NCBI Ref. Seq. No. NP_003132.2. Details of the nucleib acid sequence encoding the human TRIM21 E3 ligase protein can be found, for example, in NCBI Protein database under NCBI Ref. Seq. No. NM_003141.3.

In certain embodiments, the protein expression blocker is any one or more of the anti-CD7 PEBL as disclosed in WO2016/126213, the disclosure is herein incorporated by reference in its entirety for all purposes. Accordingly, the engineered immune cells described herein can comprise an PEBL (a target-binding molecule linked to a localizing domain) that binds to CD7, as described in WO2016/126213. The sequences of the components of anti-CD7 intrabodies as described in FIG. 2, and Tables 1 and 2 of WO2016/126213. Exemplary embodiments of an anti-CD7 PEBL are depicted in FIG. 3E and FIG. 17.

TABLE 3

Amino acid sequence information for select components of anti-CD7 PEBLs

| Component | Sequence |
|---|---|
| CD8α signal peptide | MALPVTALLLPLALLLHAARP (SEQ ID NO: 7) |
| VH-VL linker | GGGGSGGGGSGGGGSGGGGS (SEQ ID NO: 12) |
| CD8α hinge and transmembrane domain | TTTPAPRPPTPAPTIASQPLS LRPEACRPAAGGAVHTRGLDF ACDIYIWAPLAGTCGVLLLSL VITLY (SEQ ID NO: 10) |

TABLE 3-continued

Amino acid sequence information for
select components of anti-CD7 PEBLs

| Component | Sequence |
|---|---|
| Localization domain KDEL tethered to scFv with myc ("myc KDEL") | EQKLISEEDLKDEL (SEQ ID NO: 8) |
| Localization domain "link.(20)AEKDEL" | (GGGGS)$_4$AEKDEL (SEQ ID NO: 9) |
| Localization domain "mb DEKKMP" | TTTPAPRPPTPAPTIASQPLS LRPEACRPAAGGAVHTRGLDF ACDIYIWAPLAGTCGVLLLSL VITLYKYKSRRSFIDEKKMP (SEQ ID NO: 13) |
| Anti-CD7 scFv VH domain (TH69) | EVQLVESGGGLVKPGGSLKLS CAASGLTFSSYAMSWVRQTPE KRLEWVASISSGGFTYYPDSV KGRFTISRDNARNILYLQMSS LRSEDTAMYYCARDEVRGYLD VWGAGTTVTVSS (SEQ ID NO: 1) |
| Anti-CD7 scFv VL domain (TH69) | AAYKDIQMTQTTSSLSASLGD RVTISCSASQGISNYLNWYQQ KPDGTVKLLIYYTSSLHSGVP SRFSGSGSGTDYSLTISNLEP EDIATYYCQQYSKLPYTFGGG TKLEIKR (SEQ ID NO: 2) |

In some embodiments, the anti-CD7 protein expression blocker comprises an amino acid sequence of SEQ ID NO:1, an amino acid sequence of SEQ ID NO:2, and a VH-VL linker. The VH-VL linker can be a (GGGGS)$_n$ linker where n can range from 1 to 6, e.g., 1, 2, 3, 4, 5, or 6. In one embodiment, the anti-CD7 protein expression blocker comprises an amino acid sequence of SEQ ID NO:1, an amino acid sequence of SEQ ID NO:2, and an amino acid sequence of SEQ ID NO:12. In some embodiments, the anti-CD7 protein expression blocker comprises an amino acid sequence having at least 90% sequence identity or at least 95% sequence identity to SEQ ID NO:1, the amino acid sequence of SEQ ID NO:2, and the amino acid sequence of SEQ ID NO:12. In certain embodiments, the anti-CD7 protein expression blocker comprises an amino acid sequence of SEQ ID NO:1, an amino acid sequence having at least 90% sequence identity or at least 95% sequence identity to SEQ ID NO: 2, and an amino acid sequence of SEQ ID NO:12. In other embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, and an amino acid sequence of SEQ ID NO:12. In some instance, the anti-CD7 protein expression blocker also comprises a localization domain selected from any one sequence set forth in SEQ ID NO:8, SEQ ID NO:9, or SEQ ID NO:13. In some cases, the anti-CD7 protein expression blocker also comprises a CD8α signal peptide such as but not limited to the CD8α signal peptide set forth in SEQ ID NO:7. In other cases, the anti-CD7 protein expression blocker also comprises a CD8α hinge and transmembrane domain such as but not limited to the CD8α hinge and transmembrane domain set forth in SEQ ID NO:10.

In some embodiments, the anti-CD7 protein expression blocker comprises an amino acid sequence of SEQ ID NO:14, an amino acid sequence of SEQ ID NO:15, and a VH-VL linker. The VH-VL linker can be a (GGGGS)$_n$ linker where n can range from 1 to 6, e.g., 1, 2, 3, 4, 5, or 6. In one embodiment, the anti-CD7 protein expression blocker comprises an amino acid sequence of SEQ ID NO:14, an amino acid sequence of SEQ ID NO:15, and an amino acid sequence of SEQ ID NO:12. In some embodiments, the anti-CD7 protein expression blocker comprises an amino acid sequence having at least 95% sequence identity to SEQ ID NO:14, the amino acid sequence of SEQ ID NO:15, and the amino acid sequence of SEQ ID NO:12. In certain embodiments, the anti-CD7 protein expression blocker comprises an amino acid sequence of SEQ ID NO:14, an amino acid sequence having at least 95% sequence identity to SEQ ID NO:15, and an amino acid sequence of SEQ ID NO:12. In other embodiments, the anti-CD7 protein expression blocker comprises an amino acid sequence having at least 90% sequence identity or at least 95% sequence identity to SEQ ID NO:14, an amino acid sequence having at least 90% sequence identity or at least 95% sequence identity to SEQ ID NO:5, and an amino acid sequence of SEQ ID NO:12. In some instance, the anti-CD7 protein expression blocker also comprises a localization domain selected from any one sequence set forth in SEQ ID NO:8, SEQ ID NO:9, or SEQ ID NO:13. In some cases, the anti-CD7 protein expression blocker also comprises a CD8α signal peptide such as but not limited to the CD8α signal peptide set forth in SEQ ID NO:7. In other cases, the anti-CD7 protein expression blocker also comprises a CD8α hinge and transmembrane domain such as but not limited to the CD8α hinge and transmembrane domain set forth in SEQ ID NO:10.

In some embodiments, the anti-CD7 protein expression blocker comprises an amino acid sequence of SEQ ID NO:16, an amino acid sequence of SEQ ID NO:17, and a VH-VL linker. The VH-VL linker can be a (GGGGS)$_n$ linker where n can range from 1 to 5, e.g., 1, 2, 3, 4, 5, or 6 (SEQ ID NO:29). In one embodiment, the anti-CD7 protein expression blocker comprises an amino acid sequence of SEQ ID NO:16, an amino acid sequence of SEQ ID NO:17, and an amino acid sequence of SEQ ID NO:12. In some embodiments, the anti-CD7 protein expression blocker comprises an amino acid sequence having at least 90% sequence identity or at least 95% sequence identity to SEQ ID NO:16, the amino acid sequence of SEQ ID NO:17, and the amino acid sequence of SEQ ID NO:12. In certain embodiments, the anti-CD7 protein expression blocker comprises an amino acid sequence of SEQ ID NO:16, an amino acid sequence having at least 90% sequence identity or at least 95% sequence identity to SEQ ID NO:17, and an amino acid sequence of SEQ ID NO:12. In other embodiments, the anti-CD7 protein expression blocker comprises an amino acid sequence having at least 90% sequence identity or at least 95% sequence identity to SEQ ID NO:16, an amino acid sequence having at least 90% sequence identity or at least 95% sequence identity to SEQ ID NO:17, and an amino acid sequence of SEQ ID NO:12. In some instance, the anti-CD7 protein expression blocker also comprises a localization domain selected from any one sequence set forth in SEQ ID NO:8, SEQ ID NO:9, or SEQ ID NO:13. In some cases, the anti-CD7 protein expression blocker also comprises a CD8α signal peptide such as but not limited to the CD8α signal peptide set forth in SEQ ID NO:7. In other cases, the anti-CD7 protein expression blocker also comprises a CD8α hinge and transmembrane domain such as but not limited to the CD8α hinge and transmembrane domain set forth in SEQ ID NO:10.

In some embodiments, the nucleic acid sequence encoding an anti-CD7 PEBL comprises one or more nucleic acid sequences set forth in Table 4. In some embodiments, the VH domain of the anti-CD7 scFv of the PEBL comprises the nucleotide sequence of SEQ ID NO:23 and the VL domain of the anti-CD7 scFv of the PEBL comprises the nucleotide sequence of SEQ ID NO:24. In certain embodiments, the VH domain of the anti-CD7 scFv of the PEBL comprises the nucleotide sequence having at least 90% sequence identity (e.g., 90%, 91%, 92%, 93%, 94%, 95%, 96%, 97%, 98%, 99%, or more sequence identity) to SEQ ID NO:23 and the VL domain of the anti-CD7 scFv of the PEBL comprises the nucleotide sequence having at least 90% sequence identity (e.g., 90%, 91%, 92%, 93%, 94%, 95%, 96%, 97%, 98%, 99%, or more sequence identity) to SEQ ID NO:24.

TABLE 4

Nucleic acid sequence information for select components of an anti-CD7 PEBL based on TH69

| Component | Sequence |
| --- | --- |
| CD8α signal peptide | ATGGCTCTGCCTGTGACCGCAC TGCTGCTGCCCCTGGCTCTGCT GCTGCACGCCGCCAAGACCT (SEQ ID NO: 30) |
| Anti-CD7 scFv VL (TH69) | GCCGCATACAAGGATATTCAGA TGACTCAGACCACAAGCTCCCT GAGCGCCTCCCTGGGAGACCGA GTGACAATCTCTTGCAGTGCAT CACAGGGAATTAGCAACTACCT GAATTGGTATCAGCAGAAGCCA GATGGCACTGTGAAACTGCTGA TCTACTATACCTCTAGTCTGCA CAGTGGGGTCCCCTCACGATTC AGCGGATCCGGCTCTGGGACAG ACTACAGCCTGACTATCTCCAA CCTGGAGCCCGAAGATATTGCC ACCTACTATTGCCAGCAGTACT CCAAGCTGCCTTATACCTTTGG CGGGGGAACAAAGCTGGAGATT AAAAGG (SEQ ID NO: 24) |
| Anti-CD7 scFv VH (TH69) | GAGGTGCAGCTGGTCGAATCTG GAGGAGGACTGGTGAAGCCAGG AGGATCTCTGAAACTGAGTTGT GCCGCTTCAGGCCTGACCTTCT CAAGCTACGCCATGAGCTGGGT GCGACAGACACCTGAGAAGCGG CTGGAATGGGTCGCTAGCATCT CCTCTGGCGGGTTCACATACTA TCCAGACTCCGTGAAAGGCAGA TTTACTATCTCTCGGGATAACG CAAGAAATATTCTGTACCTGCA GATGAGTTCACTGAGGAGCGAG GACACCGCAATGTACTATTGTG CCAGGGACGAAGTGCGCGGCTA TCTGGATGTCTGGGGAGCTGGC ACTACCGTCACCGTCTCCAGC (SEQ ID NO: 25) |
| VH-VL Linker | GGAGGAGGAGGAAGCGGAGGAG GAGGATCCGGAGGCGGGGGATC TGGAGGAGGAGGAAGT (SEQ ID NO: 31) |
| ER localization domain KDEL tethered to scFv with myc ("myc KDEL") | GAGCAGAAACTGATTAGCGAAG AGGACCTGAAAGATGAACTG (SEQ ID NO: 32) |

In some embodiments, the nucleic acid sequence encoding the localization domain of the anti-CD7 protein expression blocker comprises a sequence selected from SEQ ID NO:32, SEQ ID NO:33, or SEQ ID NO:34, or a codon optimized variant thereof.

In certain aspects of the present invention, the protein expression blocker can bind to a molecule that is expressed on the surface of a cell including, but not limited to members of the CD1 family of glycoproteins, CD2, CD3ζ, CD4, CD5, CD7, CD8, CD25, CD28, CD30, CD38, CD45, CD45RA, CD45RO, CD52, CD56, CD57, CD99, CD127, and CD137.

In some aspects of the present invention, expression of a member of the CD1 family of glycoproteins, CD2, CD3ζ, CD4, CD5, CD7, CD8, CD25, CD28, CD30, CD38, CD45, CD45RA, CD45RO, CD52, CD56, CD57, CD99, CD127, or CD137 can be downregulated using a gene editing method, such as, but not limited to, a gene editing technology that employs meganucleases, TALEN, CRISPR/Cas9, or zinc finger nucleases. For example, in some embodiments, CD7 expression is knocked out using genome editing by Cas9/CRISPR. In other embodiments, CDS expression is knocked out using genome editing by Cas9/CRISPR.

As noted above, downregulation of CD7 expression on the effector T cells can be achieved according to a variety of other known methods including, for example, gene editing methods with meganucleases, TALEN, CRISPR/Cas9, and zinc finger nucleases. Thus, in certain embodiments, the engineered immune cell further comprises a modified CD7 gene, which modification renders the CD7 gene or protein non-functional. By way of example, the engineered immune cell of the present invention further comprises a modified (e.g., non-functional) CD7 gene (modified using, e.g., meganucleases, TALEN, CRISPR/Cas9, or zinc finger nucleases) that prevents or reduces expression of CD7, and/or otherwise impairs (e.g., structurally) the CD7 protein from being recognized by an anti-CD7 CAR. Methods of modifying gene expression using such methods are readily available and well-known in the art.

Methods of inactivating a target gene in an immune cell using CRISPR/Cas6 technology are described, for example, in US Patent Publication Nos. 2016/0272999, 2017/0204372, and 2017/0119820.

The CRISPR/Cas system is a system for inducing targeted genetic alterations (genome modifications). Target recognition by the Cas9 protein requires a "seed" sequence within the guide RNA (gRNA) and a conserved multinucleotide containing protospacer adjacent motif (PAM) sequence upstream of the gRNA-binding region. The CRISPR/Cas system can thereby be engineered to cleave substantially any DNA sequence by redesigning the gRNA in cell lines, primary cells, and engineered cells. The CRISPR/Cas system can simultaneously target multiple genomic loci by co-expressing a single Cas9 protein with two or more gRNAs, making this system uniquely suited for multiple gene editing or synergistic activation of target genes. Examples of a CRISPR/Cas system used to inhibit gene expression are described in U.S. Publication No. 2014/0068797 and U.S. Pat. Nos. 8,697,359 and 8,771,945. The system induces permanent gene disruption that utilizes the RNA-guided Cas9 endonuclease to introduce DNA double stranded breaks which trigger error-prone repair pathways to result in frame shift mutations. In some cases, other endonucleases may also be used, including but not limited to, Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, T7, Fok1, other nucleases known in the art, homologs thereof, or modified versions thereof.

CRISPR/Cas gene disruption occurs when a gRNA sequence specific for a target gene and a Cas endonuclease are introduced into a cell and form a complex that enables the Cas endonuclease to introduce a double strand break at the target gene. In some instances, the CRISPR system comprises one or more expression vectors comprising a nucleic acid sequence encoding the Cas endonuclease and a guide nucleic acid sequence specific for the target gene. The guide nucleic acid sequence is specific for a gene and targets that gene for Cas endonuclease-induced double strand breaks. The sequence of the guide nucleic acid sequence may be within a loci of the gene. In some embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40, 45, 50, or more nucleotides in length. The guide nucleic acid sequence includes a RNA sequence, a DNA sequence, a combination thereof (a RNA-DNA combination sequence), or a sequence with synthetic nucleotides, such as a peptide nucleic acid (PNA) or Locked Nucleic Acid (LNA). The guide nucleic acid sequence can be a single molecule or a double molecule. In one embodiment, the guide nucleic acid sequence comprises a single guide RNA.

In some embodiments, the engineered immune cell of the present invention can be modified via the CRISPR/Cas system to inactivate the human CD7 gene. Details of the genomic structure and sequence of the human CD7 gene can be found, for example, in NCBI Gene database under GeneID No. 924.

Commercially available kits, gRNA vectors and donor vectors, for knockout of specific target genes are available, for example, from Origene (Rockville, Md.), GenScript (Atlanta, Ga.), Applied Biological Materials (ABM; Richmond, British Colombia), BioCat (Heidelberg, Germany) or others. For example, commercially available kits or kit components for knockout of CD7 via CRISPR include, for example, those available as catalog numbers KN201231, KN201231G1, KN201231G2, and KN201231D, each available from OriGene, and those available as catalog numbers sc-4072847, sc-4072847-KO-2, sc-4072847-HDR-2, sc-4072847-NIC, sc-4072847HDR-2, and sc-4072847-NIC-2, each available from Santa Cruz Biotechnology.

In some embodiments, the chimeric antigen receptor described herein can be introduced into the human CD7 gene locus using the CRISPR/Cas system.

In certain embodiments, provided is an engineered immune cell comprising: i) a nucleic acid that comprises a nucleotide sequence encoding a chimeric antigen receptor (CAR), wherein the CAR comprises intracellular signaling domains of 4-1BB and CD3ζ, and an antibody that specifically binds Cluster of Differentiation 7 (CD7); and ii) a nucleic acid that comprises a nucleotide sequence encoding a target-binding molecule linked to a localizing domain, wherein the target-binding molecule is an antibody that binds CD7, and the localizing domain comprises an endoplasmic reticulum retention sequence. In certain embodiments, the antibody that binds CD7 in the context of the CAR, as well as in the context of the target-binding molecule comprises: a VH sequence set forth in SEQ ID NO: 1 and a VL sequence set forth in SEQ ID NO: 2; a VH sequence set forth in SEQ ID NO: 14 and a VL sequence set forth in SEQ ID NO: 15; or a VH sequence set forth in SEQ ID NO: 16 and a VL sequence set forth in SEQ ID NO: 17. As described herein, in certain embodiments, the antibody comprises a VH and a VL having sequence that each comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 1 and 2, respectively; SEQ ID NO: 14 and SEQ ID NO: 15, respectively; or SEQ ID NO: 16 and SEQ ID NO: 17, respectively. In certain embodiments, the antibody that binds CD7 in the context of the CAR can be different from the antibody that binds CD7 in the context of the target-binding molecule (the protein expression blocker or PEBL), as described herein. In certain embodiments, the intracellular signaling domain of 4-1BB comprises the sequence set forth in SEQ ID NO: 3. In certain embodiments, the intracellular signaling domain of CD3ζ comprises the sequence set forth in SEQ ID NO: 4.

In another aspect, also provided is a nucleic acid comprising a nucleotide sequence encoding a CAR, wherein the CAR comprises intracellular signaling domains of 4-1BB and CD3ζ, and an antibody that binds CD7, as described herein.

In certain embodiments, the antibody is a scFv. In certain embodiments, the scFv comprises a VH sequence set forth in SEQ ID NO: 1 and a variable light chain VL sequence set forth in SEQ ID NO: 2. In certain embodiments, the scFv comprises a VH sequence set forth in SEQ ID NO: 14 and a variable light chain VL sequence set forth in SEQ ID NO: 15. In certain embodiments, the scFv comprises a VH sequence set forth in SEQ ID NO: 16 and a variable light chain VL sequence set forth in SEQ ID NO: 17. As described herein, in certain embodiments, the scFv comprises a VH and a VL having sequence that each comprise at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 1 and 2, respectively; SEQ ID NO: 14 and SEQ ID NO: 15, respectively; or SEQ ID NO: 16 and SEQ ID NO: 17, respectively. In certain embodiments, the CAR further comprises a hinge and transmembrane sequence.

In certain embodiments, an isolated nucleic acid of the present invention comprises a nucleotide sequence that encodes a CAR according to Table 5. In some embodiments, the nucleic acid comprises a nucleotide sequence that encodes a component of the CAR according to Table 5.

TABLE 5

| Amino acid sequence information for select components of an anti-CD7 CAR | |
|---|---|
| Component | Amino Acid Sequence |
| Anti-CD7 VH (TH69) | EVQLVESGGGLVKPGGSLKLSCAASG LTFSSYAMSWVRQTPEKRLEWVASIS SGGFTYYPDSVKGRFTISRDNARNIL YLQMSSLRSEDTAMYYCARDEVRGYL DVWGAGTTVTVSS (SEQ ID NO: 1) |
| Anti-CD7 VL (TH69) | AAYKDIQMTQTTSSLSASLGDRVTIS CSASQGISNYLNWYQQKPDGTVKLLI YYTSSLHSGVPSRFSGSGSGTDYSLT ISNLEPEDIATYYCQQYSKLPYTFGG GTKLEIKR (SEQ ID NO: 2) |

TABLE 5-continued

Amino acid sequence information for select components of an anti-CD7 CAR

| Component | Amino Acid Sequence |
|---|---|
| Intracellular signaling domain of 4-1BB | KRGRKKLLYIFKQPFMRPVQTTQEED GCSCRFPEEEEGGCEL (SEQ ID NO: 3) |
| Intracellular signaling domain CD3ζ | RVKFSRSADAPAYQQGQNQLYNELNL GRREEYDVLDKRRGRDPEMGGKPRRK NPQEGLYNELQKDKMAEAYSEIGMKG ERRRGKGHDGLYQGLSTATKDTYDAL HMQALPPR (SEQ ID NO: 4) |
| Hinge and transmembrane domain of CD8α | TTTPAPRPPTPAPTIASQPLSLRPEA CRPAAGGAVHTRGLDFACDIYIWAPL AGTCGVLLLSLVITLY (SEQ ID NO: 10) |

In some embodiments, the anti-CD7 CAR comprises an amino acid sequence of SEQ ID NO:1, an amino acid sequence of SEQ ID NO:2, a 4-1BB intracellular signaling domain, a CD3ζ intracellular signaling domain, and a CD8 hinge and transmembrane domain. In some embodiments, the anti-CD7 CAR also includes a VH-VL linker such as but not limited to a (GGGGS)$_n$ linker where n can range from 1 to 6, e.g., 1, 2, 3, 4, 5, or 6.

In one embodiment, the anti-CD7 protein expression blocker comprises an amino acid sequence of SEQ ID NO:1, an amino acid sequence of SEQ ID NO:2, an amino acid sequence of SEQ ID NO:3, an amino acid sequence of SEQ ID NO:4, and an amino acid sequence of SEQ ID NO:10. In some embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, an amino acid sequence of SEQ ID NO:3, an amino acid sequence of SEQ ID NO:4, and an amino acid sequence of SEQ ID NO:10. In some embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, an amino acid sequence having at least 90% sequence identity or at least 95% sequence identity to SEQ ID NO:3, an amino acid sequence of SEQ ID NO:4, and an amino acid sequence of SEQ ID NO:10. In some embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, an amino acid sequence of SEQ ID NO:3, an amino acid sequence having at least 90% sequence identity or at least 95% sequence identity to SEQ ID NO:4, and an amino acid sequence having at least 90% sequence identity or at least 95% sequence identity to SEQ ID NO:10. In some embodiments, the anti-CD7 protein expression blocker comprises an amino acid sequence having at least 90% sequence identity or at least 95% sequence identity to SEQ ID NO:1, an amino acid sequence having at least 90% sequence identity or at least 95% sequence identity to SEQ ID NO:2, an amino acid sequence having at least 90% sequence identity or at least 95% sequence identity to SEQ ID NO:3, an amino acid sequence having at least 90% sequence identity or at least 95% sequence identity to SEQ ID NO:4, and an amino acid sequence having at least 90% sequence identity or at least 95% sequence identity to SEQ ID NO:10.

In certain embodiments, an isolated nucleic acid of the present invention comprises one or more nucleotide sequences of Table 6. In some embodiments, the nucleic acid comprises a nucleotide sequence of a component of the CAR as set forth in Table 6.

TABLE 6

Amino acid sequence information for select components of an anti-CD7 CAR

| Component | Nucleic Acid Sequence |
|---|---|
| Anti-CD7 VH (TH69) | GAGGTGCAGCTGGTCGAATCTGGAGG AGGACTGGTGAAGCCAGGAGGATCTC TGAAACTGAGTTGTGCCGCTTCAGGC CTGACCTTCTCAAGCTACGCCATGAG CTGGGTGCGACAGACACCTGAGAAGC GGCTGGAATGGGTCGCTAGCATCTCC TCTGGCGGGTTCACATACTATCCAGA CTCCGTGAAAGGCAGATTTACTATCT CTCGGGATAACGCAAGAAATATTCTG TACCTGCAGATGAGTTCACTGAGGAG CGAGGACACCGCAATGTACTATTGTG CCAGGGACGAAGTGCGCGGCTATCTG GATGTCTGGGGAGCTGGCACTACCGT CACCGTCTCCAGC (SEQ ID NO: 23) |
| Anti-CD7 VL (TH69) | GCCGCATACAAGGATATTCAGATGAC TCAGACCACAAGCTCCCTGAGCGCCT CCCTGGGAGACCGAGTGACAATCTCT TGCAGTGCATCACAGGGAATTAGCAA CTACCTGAATTGGTATCAGCAGAAGC CAGATGGCACTGTGAAACTGCTGATC TACTATACCTCTAGTCTGCACAGTGG GGTCCCCTCACGATTCAGCGGATCCG GCTCTGGGACAGACTACAGCCTGACT ATCTCCAACCTGGAGCCCGAAGATAT TGCCACCTACTATTGCCAGCAGTACT CCAAGCTGCCTTATACCTTTGGCGGG GGAACAAAGCTGGAGATTAAAAGG (SEQ ID NO: 24) |
| Intracellular signaling domain of 4-1BB | AAGCGGGGCGCAAAAAACTGCTGTA TATCTTTAAGCAGCCTTTCATGAGAC CAGTGCAGACAACCCAGGAGGAAGAT GGGTGCTCATGCCGGTTTCCCGAGGA GGAGGAAGGCGGCTGCGAGCTG (SEQ ID NO: 35) |
| Intracellular signaling domain of CD3ζ | AGGGTGAAGTTTTCCCGCTCAGCAGA TGCTCCTGCCTACCAGCAGGGCCAGA ACCAGCTGTATAATGAGCTGAACCTG GGCAGACGCGAAGAGTATGATGTGCT GGACAAAAGGCGGGGAAGAGACCCCG AAATGGGAGGGAAGCCAAGGCGGAAA AACCCCCAGGAGGGCCTGTACAATGA GCTGCAGAAGGACAAAATGGCAGAGG CTTACAGTGAGATTGGGATGAAGGGA GAGAGACGGAGGGGAAAAGGGCACGA TGGCCTGTACCAGGGGCTGAGCACAG CAACCAAAGATACTTATGACGCACTG CACATGCAGGCACTGCCACCCAGA (SEQ ID NO: 36) |

TABLE 6-continued

Amino acid sequence information for select components of an anti-CD7 CAR

| Component | Nucleic Acid Sequence |
| --- | --- |
| Hinge and transmembrane domain of CD8α | ACCACTACACCTGCACCAAGGCCTCC CACACCCGCTCCCACTATCGCTTCCC AGCCACTGTCCCTGAGGCCCGAGGCC TGCAGGCCAGCAGCTGGCGGAGCCGT GCATACTAGGGGGCTGGACTTCGCTT GCGACATCTACATCTGGGCCCCACTG GCAGGGACATGCGGAGTCCTGCTGCT GTCCCTGGTCATCACACTGTAC (SEQ ID NO: 37) |

In certain embodiments, a nucleic acid further comprises a nucleotide sequence that encodes a target-binding molecule linked to a localizing domain, as described herein. In certain embodiments, the target-binding molecule is an antibody that binds CD7. In certain embodiments, the antibody is a scFv. In some embodiments, the scFv comprises a VH sequence having at least 90% sequence identity (e.g., 90%, 91%, 92%, 93%, 94%, 95%, 96%, 97%, 98%, 99%, or more sequence identity) to the sequence of SEQ ID NO: 1 and a VL sequence having at least 90% sequence identity (e.g., 90%, 91%, 92%, 93%, 94%, 95%, 96%, 97%, 98%, 99%, or more sequence identity) to the sequence of SEQ ID NO: 2. In certain embodiments, the scFv comprises a VH sequence set forth in SEQ ID NO: 1 and a VL sequence set forth in SEQ ID NO: 2. In some embodiments, the VH domain of the anti-CD7 scFv comprises the nucleotide sequence of SEQ ID NO:23 and the VL domain of the anti-CD7 scFv comprises the nucleotide sequence of SEQ ID NO:24.

In other aspects, also provided is a method of treating cancer in a subject in need thereof, comprising administering a therapeutic amount of an engineered immune cell having any of the embodiments described herein to the subject, thereby treating cancer in a subject in need thereof.

In certain embodiments, the method comprises administering a therapeutic amount of an engineered immune cell comprising a nucleic acid that comprises a nucleotide sequence encoding a CAR, wherein the CAR comprises intracellular signaling domains of 4-1BB and CD3ζ, and an antibody that binds CD7, as described herein.

In certain embodiments, the method comprises administering a therapeutic amount of an engineered immune cell that further comprises a nucleic acid having a nucleotide sequence encoding a target-binding molecule linked to a localizing domain, as described herein (e.g., an anti-CD7 protein expression blocker).

In certain embodiments, the cancer is a T cell malignancy, e.g., T cell leukemia or T cell lymphoma, such a T-cell acute lymphoblastic leukemia, T-cell prolymphocytic leukemia, T-cell large granular lymphocytic leukemia, enteropathy-associated T-cell lymphoma, hepatosplenic T-cell lymphoma, subcutaneous panniculitis-like T-cell lymphoma, mycosis fungoides, Sézary syndrome, primary cutaneous gamma-delta T-cell lymphoma, peripheral T-cell lymphoma not otherwise specified, angioimmunoblastic T-cell lymphoma, anaplastic large cell lymphoma. In certain embodiments, the T cell malignancy is early T-cell progenitor acute lymphoblastic leukemia (ETP-ALL).

As used herein, the terms "treat," "treating," or "treatment," refer to counteracting a medical condition (e.g., a condition related to a T cell malignancy) to the extent that the medical condition is improved according to a clinically-acceptable standard.

As used herein, "subject" refers to a mammal (e.g., human, non-human primate, cow, sheep, goat, horse, dog, cat, rabbit, guinea pig, rat, mouse). In certain embodiments, the subject is a human. A "subject in need thereof" refers to a subject (e.g., patient) who has, or is at risk for developing, a disease or condition that can be treated (e.g., improved, ameliorated, prevented) by inducing T cells to exert specific cytotoxicity against malignant T cells.

As defined herein, a "therapeutic amount" refers to an amount that, when administered to a subject, is sufficient to achieve a desired therapeutic effect (treats a condition related to a T cell malignancy) in the subject under the conditions of administration. An effective amount of the agent to be administered can be determined by a clinician of ordinary skill using the guidance provided herein and other methods known in the art, and is dependent on several factors including, for example, the particular agent chosen, the subject's age, sensitivity, tolerance to drugs and overall well-being.

In some embodiments, the engineered immune cell is autologous to the subject in need of treatment, e.g., cancer treatment. In other embodiments, the engineered immune cell is allogenic to the subject in need of treatment.

In certain embodiments, the engineered immune cell is administered into the subject by intravenous infusion, intra-arterial infusion, direct injection into tumor and/or perfusion of tumor bed after surgery, implantation at a tumor site in an artificial scaffold, intrathecal administration, and intraocular administration.

In certain embodiments, the engineered immune cell is administered by infusion into the subject. Methods of infusing immune cells (e.g., allogeneic or autologous immune cells) are known in the art. A sufficient number of cells are administered to the recipient in order to ameliorate the symptoms of the disease. Typically, dosages of $10^7$ to $10^{10}$ cells are infused in a single setting, e.g., dosages of $10^9$ cells. Infusions are administered either as a single $10^9$ cell dose or divided into several $10^9$ cell dosages. The frequency of infusions can be daily, every 2 to 30 days or even longer intervals if desired or indicated. The quantity of infusions is generally at least 1 infusion per subject and preferably at least 3 infusions, as tolerated, or until the disease symptoms have been ameliorated. The cells can be infused intravenously at a rate of 50-250 ml/hr. Other suitable modes of administration include intra-arterial infusion, intraperitoneal infusion, direct injection into tumor and/or perfusion of tumor bed after surgery, implantation at the tumor site in an artificial scaffold, intrathecal administration. Methods of adapting the present invention to such modes of delivery are readily available to one skilled in the art.

In certain embodiments, the method of treating cancer according to the present invention is combined with at least one other known cancer therapy, e.g., radiotherapy, chemotherapy, or other immunotherapy.

In other aspects, also provided is use of an engineered immune cell having any of the embodiments described herein for treating cancer, comprising administering a therapeutic amount of the engineered immune cell to a subject in need thereof. In certain embodiments, the cancer is a T cell malignancy. In certain embodiments, the T cell malignancy is early T-cell progenitor acute lymphoblastic leukemia (ETP-ALL).

In certain embodiments, the engineered immune cell is administered into the subject by intravenous infusion, intra-arterial infusion, intraperitoneal infusion, direct injection into tumor and/or perfusion of tumor bed after surgery, implantation at a tumor site in an artificial scaffold, and intrathecal administration.

In another aspect, also provided is a method for producing the engineered immune cell having any of the embodiments described herein, the method comprising introducing into an immune cell a nucleic acid that comprises a nucleotide sequence encoding a CAR, wherein the CAR comprises intracellular signaling domains of 4-1BB and CD3ζ, and an antibody that binds CD7.

In certain embodiments, the method further comprises introducing into the immune cell a nucleic acid that comprises a nucleotide sequence encoding a target-binding molecule linked to a localizing domain (e.g., anti-CD7 protein expression blocker or anti-CD7 PEBL). In certain embodiments, the nucleotide sequence encoding CAR and the nucleotide sequence encoding the anti-CD7 PEBL are introduced on a single plasmid.

In various aspects, also provided is a kit for producing an engineered immune cell described herein. The present kit can be used to produce, e.g., allogeneic or autologous T cells having anti-CD7 CAR-mediated cytotoxic activity. In some embodiments, the kit is useful for producing allogeneic effector T cells having anti-CD7 CAR-mediated cytotoxic activity. In certain embodiments, the kit is useful for producing autologous effector T cells having anti-CD7 CAR-mediated cytotoxic activity.

Accordingly, provided herein is a kit comprising a nucleic acid comprising a nucleotide sequence encoding a CAR, wherein the CAR comprises intracellular signaling domains of 4-1BB and CD3ζ, and an antibody that binds CD7. The nucleotide sequence encoding the anti-CD7 CAR can be designed according to any of the embodiments described herein. In certain embodiments, the nucleotide sequence encodes the anti-CD7 CAR according to the schematic in FIG. 1A ("anti-CD7-41BB-CD3ζ construct").

In certain embodiments, the kit further comprises a nucleic acid having a nucleotide sequence that encodes a target-binding molecule linked to a localizing domain, as described herein (e.g., anti-CD7 PEBL molecules described herein). The nucleotide sequence encoding the target-binding molecule linked to a localizing domain can be designed according to any of the embodiments described herein.

In certain embodiments, the nucleotide sequence encoding the anti-CD7 CAR and/or the nucleotide sequence encoding the anti-CD7 PEBL further comprise sequences (e.g., plasmid or vector sequences) that allow, e.g., cloning and/or expression. For example, the nucleotide sequence can be provided as part of a plasmid for ease of cloning into other plasmids and/or vectors (expression vectors or viral expression vectors) for, e.g., transfection, transduction, or electroporation into a cell (e.g., an immune cell). In certain embodiments, the nucleotide sequence encoding the anti-CD7 CAR and the nucleotide sequence encoding the anti-CD7 PEBL are provided on a single plasmid or vector (e.g., a single construct comprising an anti-CD7 CAR and an anti-CD7 PEBL). In certain embodiments, the nucleotide sequences are provided on separate plasmids or vectors (expression vectors or viral expression vectors).

Typically, the kits are compartmentalized for ease of use and can include one or more containers with reagents. In certain embodiments, all of the kit components are packaged together. Alternatively, one or more individual components of the kit can be provided in a separate package from the other kits components. The kits can also include instructions for using the kit components.

In some embodiments, provided herein is an engineered immune cell comprising a nucleic acid that comprises a nucleotide sequence encoding a chimeric antigen receptor (CAR), wherein the CAR comprises intracellular signaling domains of 4-1BB and CD3ζ, and an antibody that binds Cluster of Differentiation 7 (CD7). In certain embodiments, the antibody is a single chain variable fragment (scFv). In some instances, the scFv comprises a heavy chain variable domain (VH) sequence set forth in SEQ ID NO: 1 and a light chain variable domain (VL) sequence set forth in SEQ ID NO: 2.

In some embodiments, the CAR further comprises a hinge and transmembrane sequence, such as but not limited to a hinge and transmembrane domain comprising the amino acid sequence of SEQ ID NO:10.

In some embodiments, the engineered immune cell is an engineered T cell, an engineered natural killer (NK) cell, an engineered NK/T cell, an engineered monocyte, an engineered macrophage, or an engineered dendritic cell.

In some embodiments, the engineered immune cell further comprising a nucleic acid that comprises a nucleotide sequence encoding a target-binding molecule linked to a localizing domain. In certain embodiments, the target-binding molecule is an antibody that binds CD7. In certain embodiments, the antibody is an scFv. In some embodiments, the scFv comprises a VH sequence set forth in SEQ ID NO: 1 and a VL sequence set forth in SEQ ID NO: 2. In some embodiments, the localizing domain comprises an endoplasmic reticulum (ER) or Golgi retention sequence; a proteosome localizing sequence; a transmembrane domain sequence derived from CD8α, CD8β, 4-1BB, CD28, CD34, CD4, FcεRIγ, CD16, OX40, CD3ζ, CD3ε, CD3γ, CD3δ, TCRα, CD32, CD64, VEGFR2, FAS, or FGFR2B.

In some embodiments, provided herein is an engineered immune cell comprising: (i) a nucleic acid that comprises a nucleotide sequence encoding a chimeric antigen receptor (CAR), wherein the CAR comprises intracellular signaling domains of 4-1BB and CD3ζ, and an antibody that binds Cluster of Differentiation 7 (CD7); and (ii) a nucleic acid that comprises a nucleotide sequence encoding a target-binding molecule linked to a localizing domain, wherein the target-binding molecule is an antibody that binds CD7, and the localizing domain comprises an endoplasmic reticulum retention sequence, and wherein the antibody that binds CD7 comprises a variable heavy chain (VH) sequence set forth in SEQ ID NO: 1 and a variable light chain (VL) sequence set forth in SEQ ID NO: 2. In some embodiments, the intracellular signaling domain of 4-1BB comprises the sequence set forth in SEQ ID NO: 3 and the intracellular signaling domain of CD3ζ comprises the sequence set forth in SEQ ID NO: 4.

In some embodiments, provided herein is an method of treating cancer in a subject in need thereof, comprising administering a therapeutic amount of the engineered immune cell described herein to the subject, thereby treating cancer in a subject in need thereof. In some embodiments, the cancer is a T cell malignancy. In certain embodiments, the T cell malignancy is early T-cell progenitor acute lymphoblastic leukemia (ETP-ALL). In certain embodiments, the engineered immune cell is administered into the subject by intravenous infusion, intra-arterial infusion, intraperitoneal infusion, direct injection into tumor and/or perfusion of tumor bed after surgery, implantation at a tumor site in an artificial scaffold, intrathecal administration.

In some embodiments, provided herein is a nucleic acid comprising a nucleotide sequence encoding a chimeric antigen receptor (CAR), wherein the CAR comprises intracellular signaling domains of 4-1BB and CD3ζ, and an antibody that binds Cluster of Differentiation 7 (CD7).

In other embodiments, provided herein is the of the engineered immune cell described herein for treating cancer comprising administering a therapeutic amount of the engineered immune cell to a subject in need thereof. In some embodiments, the cancer is a T cell malignancy. In certain embodiments, the T cell malignancy is early T-cell progenitor acute lymphoblastic leukemia (ETP-ALL). In certain embodiments, the engineered immune cell is administered into the subject by intravenous infusion, intra-arterial infusion, intraperitoneal infusion, direct injection into tumor and/or perfusion of tumor bed after surgery, implantation at a tumor site in an artificial scaffold, intrathecal administration.

In some embodiments, provided herein is a method for producing the engineered immune cell described herein. The method can include: introducing into an immune cell a nucleic acid that comprises a nucleotide sequence encoding a CAR, wherein the CAR comprises intracellular signaling domains of 4-1BB and CD3ζ, and an antibody that binds CD7, thereby producing an engineered immune cell. The method can further comprise introducing into the immune cell a nucleic acid that comprises a nucleotide sequence encoding a target-binding molecule linked to a localizing domain.

The present invention provides a chimeric antigen receptor (CAR) directed against CD7. As demonstrated herein, the expression of the anti-CD7 CAR in immune cells such as effector T cells, induces the T cell to exert specific cytotoxicity against T cell malignancies. This cytotoxic effect was shown to be enhanced when expression of CD7 on the effector T cells was downregulated using an antibody-based molecule (a protein expression blocker or PEBL) that targeted the CD7 for downregulation. Thus, the present invention provides an immunotherapeutic method for treating cancers, e.g., T-cell malignancies.

In some aspects, the present invention provides an engineered immune cell comprising a nucleic acid that comprises a nucleotide sequence encoding a chimeric antigen receptor (CAR), wherein the CAR comprises intracellular signaling domains of 4-1BB and CD3ζ, and an antibody that binds Cluster of Differentiation 7 (CD7). In some embodiments, the engineered immune cell outlined herein also includes a nucleic acid that comprises a nucleotide sequence encoding a target-binding molecule linked to a localizing domain (e.g., a protein expression blocker or PEBL). Outlined herein is also a method and kit for producing such an engineered immune cell.

In some aspects, the present invention provides an engineered immune cell (e.g., T cell, natural killer (NK) cell, NK/T cell, monocyte, macrophage, or dendritic cell) comprising (i) a nucleic acid that comprises a nucleotide sequence encoding a chimeric antigen receptor (CAR), wherein the CAR comprises intracellular signaling domains of 4-1BB and CD3ζ, and an antibody that specifically binds CD7; and (ii) a nucleic acid that comprises a nucleotide sequence encoding a target-binding molecule linked to a localizing domain, wherein the target-binding molecule is an antibody that binds CD7, and the localizing domain comprises an endoplasmic reticulum retention sequence, and wherein the antibody that binds CD7 comprises a variable heavy chain (VH) sequence set forth in SEQ ID NO: 1 and a variable light chain (VL) sequence set forth in SEQ ID NO: 2.

In other aspects, the present invention provides a method of treating cancer (e.g., a T cell malignancy) in a subject in need thereof. The method includes administering a therapeutic amount of any of the engineered immune cells described herein to the subject, thereby treating cancer in a subject in need thereof. The disclosure also sets forth the use of any of the engineered immune cells outlined herein for treating cancer.

In other aspects, the present invention provides a nucleic acid comprising a nucleotide sequence encoding a chimeric antigen receptor (CAR), wherein the CAR comprises intracellular signaling domains of 4-1BB and CD3ζ, and an antibody that specifically binds CD7.

EXAMPLES

Example 1: Blockade of Cd7 Expression in T Cells for Effective Chimeric Antigen-Receptor Targeting of T-Cell Malignancies This example illustrates blockade of CD7 expression with a novel method, combined with a second-generation CAR, resulted in highly potent anti-CD7 CAR-T cells. This practical strategy provides a new treatment option for patients with high-risk T-cell malignancies, including ETP-ALL.

Abstract

Effective immunotherapies for T-cell malignancies are lacking. A novel approach based on chimeric antigen receptor (CAR)-redirected T lymphocytes was devised. CD7 was selected as a target because of its consistent expression in T-cell acute lymphoblastic leukemia (T-ALL), including the most aggressive subtype, early T-cell precursor (ETP)-ALL. In 49 diagnostic T-ALL samples (including 14 ETP-ALL), median CD7 expression was >99%; CD7 expression remained high at relapse (n=14), and during chemotherapy (n=54). CD7 was targeted with a second-generation CAR (anti-CD7-41BB-CD3ζ) but CAR expression in T lymphocytes caused fratricide, owing to CD7 present in the T cells themselves. To downregulate CD7 and control fratricide, a new method (Protein Expression Blocker, PEBL), based on an anti-CD7 single chain variable fragment coupled with an intracellular retention domain was applied. Transduction of anti-CD7 PEBL resulted in virtually instantaneous abrogation of surface CD7 expression in all transduced T cells; 2.0%±1.7% were CD7+ versus 98.1%±1.5% of mock-transduced T cells (n=5; P<0.0001). PEBL expression did not impair T-cell proliferation, IFNγ and TNFα secretion, or cytotoxicity, and eliminated CAR-mediated fratricide. PEBL-CAR-T cells were highly cytotoxic against CD7+ leukemic cells in vitro, and were consistently more potent than CD7+ T cells spared by fratricide. They also showed strong anti-leukemic activity in cell line- and patient-derived T-ALL xenografts. The strategy described here fits well with existing clinical-grade cell manufacturing processes, and can be rapidly implemented for the treatment of patients with high-risk T-cell malignancies.

INTRODUCTION

T lymphocytes can be induced to specifically recognize and kill tumor cells through the expression of chimeric antigen receptors (CARs).[1-5] Central to the effective application of this technology is the identification of a suitable target for the CAR. This must be highly expressed by tumor cells and should be absent in normal cells, or be expressed only by normal cells whose temporary absence is clinically manageable.[6] Thus, leukemias and lymphomas of B-cell origin can be targeted with CARs directed against CD19,[5,7] or CD22,[8] which are normally expressed only by B lymphoid cells.[9,10] Infusion of autologous T cells expressing anti-CD19 CARs in patients with B-cell refractory leukemia and lymphoma resulted in major clinical responses.[11-18] These exciting results have provided indisputable evidence of the power of this technology, and suggest the possibility of wider applications in oncology.

The development of CAR-T cell therapies for T-cell malignancies has lagged far behind that of their B-cell counterparts. The need for effective therapies in this area is particularly urgent because of the poor prognosis associated with some T-cell leukemia and lymphoma subtypes. For example, children and adolescents with early T-cell progenitor acute lymphoblastic leukemia (ETP-ALL) have the poorest response to initial therapy among all patients with ALL.[19-21] Intensive chemotherapy and/or allogeneic hematopoietic stem cell transplant often do not prevent treatment-refractory relapse; for these patients, and those with other high-risk features, such as adult age, there is a dearth of treatment options.[19,22-25]

A major obstacle to the development of effective CAR-T cells for T-cell malignancies is that the surface marker profile of malignant T cells (which generally lack CD19 or CD22 expression) largely overlaps that of activated T lymphocytes.[19,26] CAR directed against such targets are likely to lead to the self-elimination of the CAR-T cells.[27,28] Described herein is the development and application of a practical technology for CAR-T cell therapy of ETP-ALL and other T-ALL cell subtypes. First, a CAR directed against CD7 was made. As one recognizes, CD7 is a 40 kDa type I transmembrane glycoprotein that is a primary marker for T-cell malignancies,[29-32] and is highly expressed in all cases of T-cell ALL, including ETP-ALL.[19] Second, a method to rapidly and effectively downregulate CD7 expression in T cells was developed. The method was selected as it averts the fratricide effect of CAR-T cell therapy, does not involve gene editing, and can be immediately translated into clinical applications.

Materials and Methods

Cells and Culture Conditions

The leukemia cell lines Jurkat, CCRF-CEM, Loucy, MOLT4 and KG1a were from the American Type Culture Collection (ATCC; Rockville, Md.). The B-lineage ALL cell line OP-1 was developed in our laboratory.[33] The CCRF-CEM cells were transduced with a murine stem cell virus (MSCV)—internal ribosome entry site (IRES)—green fluorescent protein (GFP) retroviral vector (from the Vector Development and Production Shared Resource of St. Jude Children's Research Hospital, Memphis, Tenn.) containing the firefly luciferase gene. The same vector was used to transduce CCRF-CEM and Jurkat cells with the CD19 gene, which was cloned from the cDNA of the RS4; 11 B-cell line (ATCC). Cell lines were maintained in RPMI-1640 (ThermoFisher Scientific, Waltham, Mass.) supplemented with 10% fetal bovine serum (FBS) and 1% penicillin-streptomycin.

Peripheral blood samples were obtained from discarded anonymized by-products of platelet donations from healthy adult donors at the National University Hospital Blood Bank, Singapore. Bone marrow aspirates from patients with ALL were obtained for diagnostic immunophenotyping, and monitoring of treatment response,[19,26] banked surplus material was used in some experiments, with approval from the Institutional Review Board, National University of Singapore. Mononucleated cells were separated by centrifugation on a Lymphoprep density step (Axis-Shield, Oslo, Norway) and washed twice in RPMI-1640. T cells were enriched with Dynabeads Human T-Activator CD3/CD28 (ThermoFisher) and cultured in RPMI-1640, 10% FBS, 1% penicillin-streptomycin, and interleukin-2 (IL-2; 120 IU/mL; Proleukin, Novartis, Basel, Switzerland).

Gene Cloning and Retroviral Transduction

The single chain variable fragment (scFv) of the anti-CD7 monoclonal antibody TH69[34] was joined to the CD8α signal peptide, CD8α hinge and transmembrane domain, and the intracellular domains of 4-1BB and CD3ζ of an anti-CD19-41BB-CD3ζ CAR previously developed in our laboratory.[5] The same scFv was also joined to the CD8α signal peptide and sequences encoding endoplasmic reticulum (ER)/Golgi retention peptides EQKLISEEDLKDEL (SEQ ID NO:8), (GGGGS)$_4$AEKDEL (SEQ ID NO:9), or CD8α hinge and transmembrane domain followed by localizing sequence (SEQ ID NO:13). These were subcloned into the MSCV vector, with or without GFP or mCherry.

Preparation of retroviral supernatant and transduction were performed as previously described.[5,35] Briefly, pMSCV retroviral vector-conditioned medium was added to RetroNectin (Takara, Otsu, Japan)-coated polypropylene tubes; after centrifugation and removal of the supernatant, T cells were added to the tubes and left at 37° C. for 12 hours; fresh viral supernatant was added on two other successive days. T lymphocytes were maintained in RPMI-1640 with FBS, antibiotics and 200 IU/mL IL-2.

For transient CAR expression, anti-CD7 and anti-CD19 CAR constructs were subcloned into EcoRI and XhoI sites of the pVAXI vector (ThermoFisher Scientific), and transcribed into mRNA using T7 mScript (CellScript, Madison, Wis.).[36] For mRNA electroporation, cells were suspended in electroporation buffer (Amaxa Cell Line Nucleofector Kit V; Lonza, Basel, Switzerland) containing 200 µg of CAR mRNA, and electroporated with an Amaxa Nucleofector 2b (Lonza) using program X-001.[36,37] Cells electroporated without mRNA were used as control.

Detection of CAR, PEBL and Surface Markers

CARs were detected with a biotin-conjugated goat anti-mouse F(ab')$_2$ antibody (Jackson ImmunoResearch, West Grove, Pa.) followed by allophycocyanin (APC)-conjugated streptavidin (Jackson ImmunoResearch). Phycoerythrin (PE)- or APC-conjugated anti-CD7 (M-T701), CD4 (RPA-T4), CD8 (RPA-T8), CD3ζ (SK7), and non-reactive isotype-matched antibodies were from BD Biosciences (San Jose, Calif.); CD19 (LT19) was from Miltenyi Biotech. Cell staining was analyzed using Accuri C6, Fortessa or LSRII flow cytometers (BD Biosciences), with Diva (BD Biosciences) or FlowJo software (FlowJo, Ashland, Oreg.).

Western blotting was performed as previously described.[35] Briefly, cell lysates were extracted using CelLytic M cell lysis reagent (Sigma-Aldrich, Saint Louis, Mo.) prior to protein quantification with Pierce BCA protein assay kit (ThermoFisher). Cell lysates were diluted with 4× Laemmli sample buffer (Bio-rad, Hercules, Calif.) and separated on 10% polyacrylamide gel by electrophoresis under reducing or non-reducing conditions. Blotted membranes were probed with mouse anti-human CD3ζ antibody (8D3; BD Biosciences), goat anti-mouse IgG horseradish peroxidase-conjugated (R&D Systems, Minneapolis, Minn.), and Clarity Western ECL substrate (Bio-Rad). Staining was visualised using ChemiDoc Touch Imager (Bio-Rad).

Cell Aggregation Assay, Cytotoxicity Assays and Cytokine Production

To measure cell-cell aggregation, Jurkat cells were co-cultured with the CD7+ or CD7− cells labeled with calcein red-orange AM (ThermoFisher) for 30 minutes; cell doublets were counted by flow cytometry. In some experiments, target cells were pre-incubated for 10 minutes before co-culture with a soluble anti-CD7 scFv, obtained from the supernatant of Jurkat or 293T cells transduced with a construct consisting of the scFv without transmembrane or signaling sequences.

To test cytotoxicity, target cells were labeled with calcein red-orange AM and placed into a 96-well round bottom plate (Corning Costar, Corning, N.Y.). T cells were added at different effector: target (E:T) ratios with target cells and cultured for 4 hours at 37° C. and 5% CO2. Viable target cells were counted by flow cytometry.38 To measure exocytosis of lytic granules, anti-human CD107a-PE (H4A3; BD Biosciences) was added to the co-cultures. After 1 hour, monensin (BD GolgiStop) was added, and the cultures were continued for another 3 hours before flow cytometric analysis.

To assess cell proliferation, T-cells were cultured alone or in presence of MOLT-4 cells at 1:1 E:T in RPMI-1640 with FBS and 120 IU/mL IL-2 at 37° C. and 5% $CO_2$. Target cells, irradiated or treated with Streck cell preservative (Streck Laboratories, Omaha, Nebr.) to inhibit proliferation, were added to the cultures every 7 days. Viable GFP+ or mCherry+ T-cells were enumerated by flow cytometry. For IFNγ and TNFα production, target and effector cells at 1:1 E:T were plated as above. After 1 hour, brefeldin A (BD GolgiPlug) was added to the cultures, which continued for another 5 hours. Subsequently, intracellular staining with anti-IFNγ-PE (clone 25723.11; BD Biosciences) or anti-TNFα-PE (6401.1111; BD Biosciences) was done prior to flow cytometric analysis.

Xenograft Models

CCRF-CEM cells transduced with luciferase were injected intravenously (i.v.) in NOD.Cg-Prkdc$^{scid}$ IL2rg$^{tm1wjl}$/SzJ (NOD/scid IL2RGnull) mice (Jackson Laboratory, Bar Harbor, Me.) at $1 \times 10^6$ cells per mouse. Three and/or seven days later, mice received T cells with downregulated CD7 and anti-CD7 CAR expression at $2 \times 10^7$ T cells per mouse. Other mice received T cells transduced with GFP alone, or RPMI-1640 with 10% FBS instead of T cells. All mice received 20,000 IU of IL-2 intraperitoneally (i.p.) every 2 days. Tumor load was determined using the Xenogen IVIS-200 System (Caliper Life Sciences, Waltham, Mass.) after injecting aqueous D-luciferin potassium salt (Perkin Elmer, Waltham, Mass.) i.p. (2 mg per mouse). Luminescence was analyzed with the Living Image 3.0 software. Mice were euthanized when luminescence reached $1 \times 10^{10}$ photons per second, or earlier if physical signs warranting euthanasia appeared.

For the patient-derived xenograft (PDX) model, primary ETP-ALL cells were injected i.v. in NOD/scid IL2RGnull and propagated for 7-8 subsequent generations. ETP-ALL cells were then re-injected in NOD/scid IL2RGnull which were either treated with PEBL-CAR-T cells or left untreated. Peripheral blood and tissues were monitored for the presence of ALL cells by flow cytometry.[19,26] After red blood cells lysis with a lysing buffer (Sigma-Aldrich), cells were stained with anti-mouse CD45-PE-Cyanine 7 (30-F11, Biolegend), as well as anti-human CD45-APC-H7 (2D1), CD7-PE (M-T701), CD3 APC (SK7), CD34-peridinin chlorophyll protein (8G12) (all from BD Biosciences), and CD33-Brilliant Violet 421 (WM53, Biolegend). Cells were analyzed with a Fortessa flow cytometer, using Diva and FlowJo software.

Results

Validation of CD7 as a Target for CAR-T Cell Therapy in Leukemia

Figure 1B:
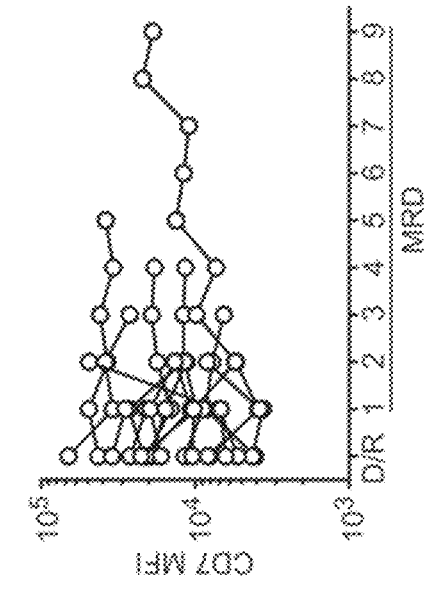

In leukemic cells from diagnostic bone marrow samples obtained from 49 patients with T-ALL (including 14 with ETP-ALL), median percent CD7 expression was >99% (range, 79%-→99%). In only 3 cases (6.1%), CD7 was lower than 99%: 98% in two, and 79% in one (FIG. 1A). High CD7 expression was also observed in samples collected from 14 patients with relapse T-ALL (FIG. 1A). Mean fluorescence intensity (MFI) of CD7 in leukemic cells at diagnosis or relapse consistently exceeded that measured in residual normal T cells in the same samples. Median (range) MFI was 20,617 (4,105-66,674) in T-ALL cells versus 3,032 (1,301-9,582) in the normal T cells (n=19; P<0.0001) (FIG. 1B).

Figure 1C:
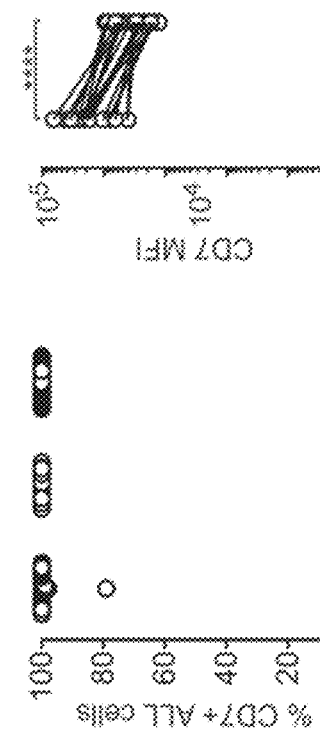
Figure 1D:
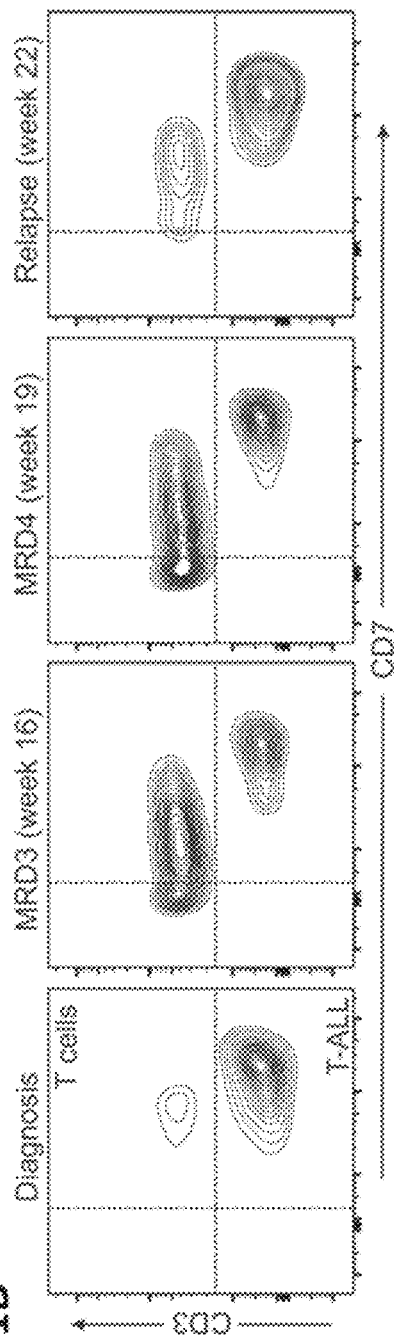

To determine whether chemotherapy affected CD7 expression, bone marrow samples collected during therapy that contained minimal residual disease (MRD) were examined. In all 54 samples (from 21 patients), >99% of residual leukemic cells were CD7+ (FIG. 1A). In 18 patients, CD7 levels were monitored during the course of the disease. As shown in FIG. 1C and FIG. 1D, CD7 remained high during therapy. These results validate CD7 as a target for CAR-T cell therapy in T-ALL.

Design and Expression of an Anti-CD7 CAR

To target CD7, an anti-CD7 CAR composed of the scFv of the anti-CD7 antibody TH69 joined to the signaling domains of 4-1BB (CD137) and CD3ζ via the hinge and transmembrane domain of CD8α (FIG. 2A) was designed. Retroviral transduction of this construct in Jurkat cells resulted in high expression of anti-CD7 CAR (FIG. 2B), which appeared as monomer, dimer and oligomer by western blotting (FIG. 2C).

To confirm that the TH69 scFv could bind CD7, it was produced in soluble form and was tested on CD7+ MOLT-4 and CD7− OP-1 cells; MOLT-4 cells were labelled while OP-1 were not (FIG. 8A). Further, staining with an anti-CD7 monoclonal antibody was significantly reduced when MOLT-4 cells were pre-incubated with the anti-CD7 scFv supernatant; CD7 MFI (±SD) went from 31,730±1,144 to 5,987±241 (n=3). Jurkat cells expressing anti-CD7 CAR formed aggregates with CD7+ MOLT-4 cells, whereas those transduced with GFP only, or with an anti-CD19 CAR, did not; conversely, the anti-CD19 CAR induced cell aggregation with CD19+ OP-1 cells while the anti-CD7 CAR did not (FIG. 8B). Pre-incubation of MOLT-4 or CCRF-CEM with the soluble anti-CD7 scFv prevented the formation of aggregates (FIG. 8C).

To determine whether the anti-CD7 CAR was functional, levels of the activation markers CD25 and CD69 were measured in Jurkat cells after 24-hour co-culture with MOLT4. There was a clear upregulation of both activation markers in cells expressing the anti-CD7 CAR (FIGS. 2D and 2E). In sum, the anti-CD7-41BB-CD3ζ CAR can bind to its cognate antigen, and transduces activation signals upon ligation.

Expression of Anti-CD7 CAR in T Cells Causes Fratricide

Figure 9B:
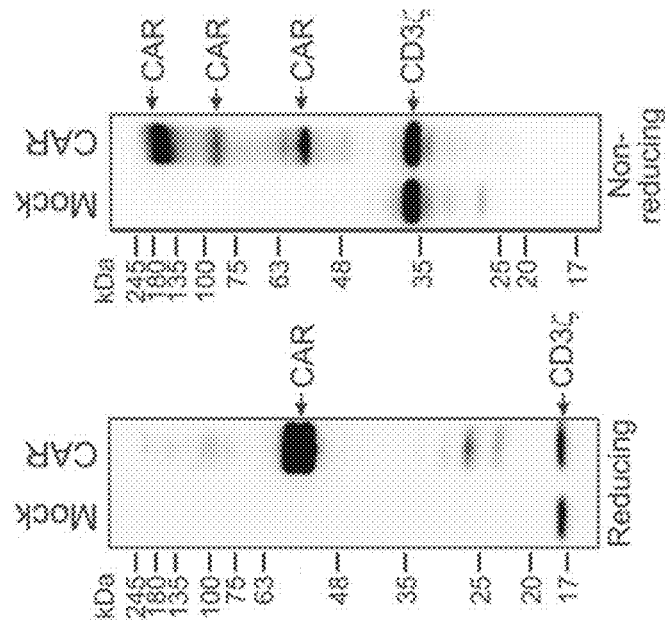
FIG. 9A and FIG. 9B show expression of anti-CD7-41BB-CD3ζCAR in human peripheral blood T lymphocytes.
Figure 9A:
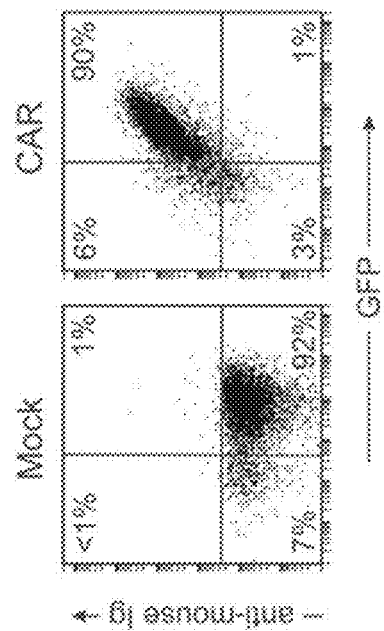

To determine the effects of anti-CD7-41BB-CD3ζ CAR in peripheral blood T lymphocytes, two different methods were used to express it: retroviral transduction (FIG. 9A) and mRNA electroporation. However, it markedly reduced T-cell viability. Mean (±SD) T-cell recovery 24 hours after mRNA electroporation was 39.8%±13.0 (n=7) of the recovery after electroporation without mRNA (FIG. 3A); if the CAR was introduced by viral transduction, cell recovery was 25.1%±16.2% (n=10) of that of mock-transduced T cells (FIG. 3B); overall, CAR expression reduced cell recovery to 31.1%±16.3% (n=17) after 24 hours. Prolonging cell culture further increased the difference in numbers between CAR- and mock-transduced cells overall (FIG. 3C). CAR expression, in the absence of target cells, induced exocytosis of lytic granules revealed by CD107a expression (FIG. 3D), suggesting that impaired cell recovery was caused by fratricide.

Figure 3G:
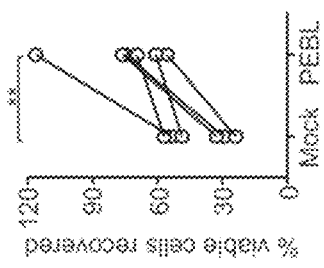
Figure 3H:
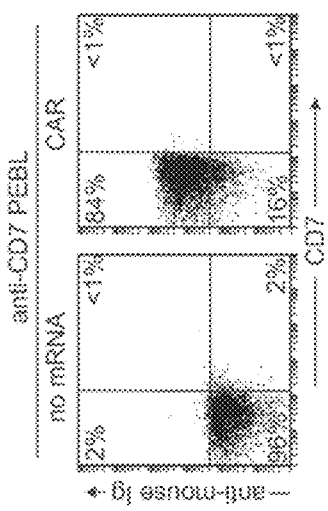
Figure 3I:
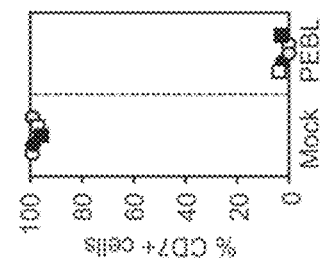
Figures 10A, 10B:
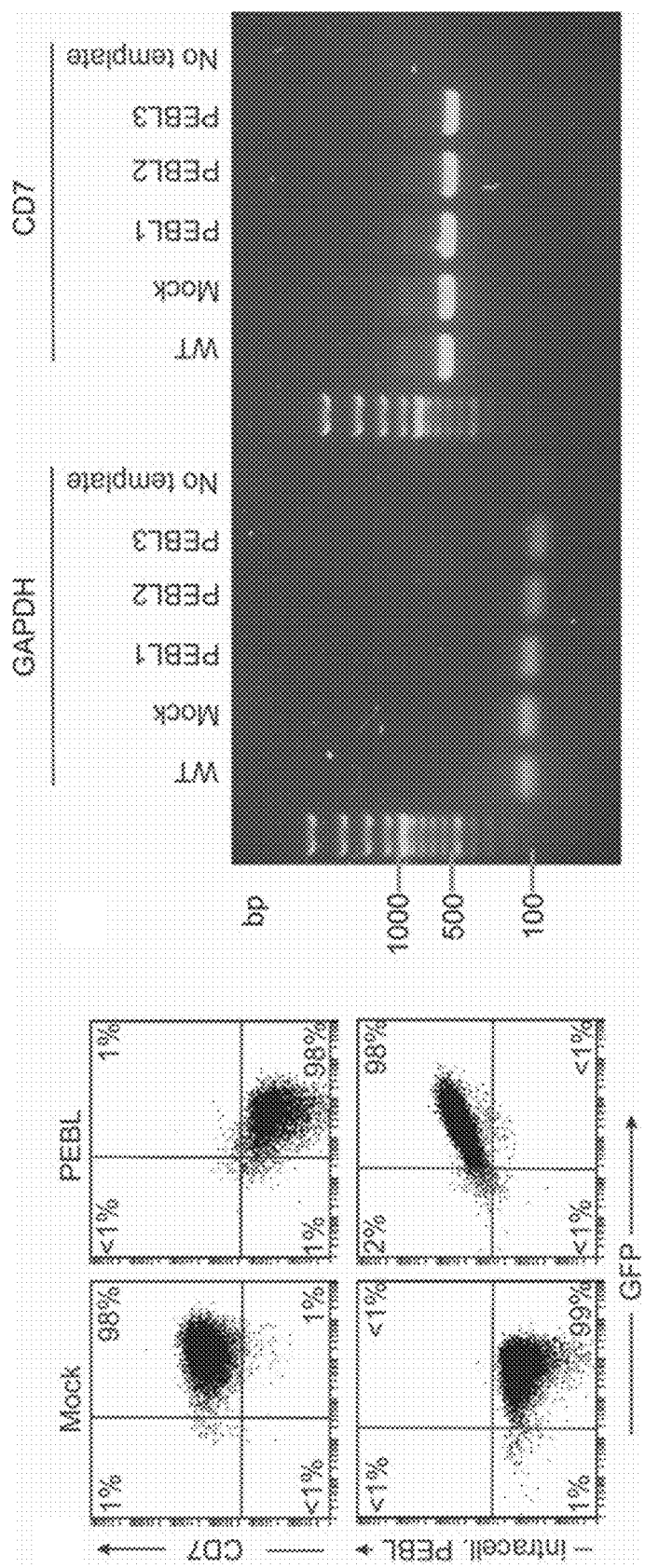
FIG. 10A and FIG. 10B illustrate downregulation of CD7 protein expression with anti-CD7 PEBLs. Flow cytometric dot plot illustrate GFP expression (x axes), CD7 expression (y axes, top row), and intracellular anti-CD7 PEBL-1 expression (y axes, bottom row) (FIG. 10A). T lymphocytes were retrovirally transduced with anti-CD7 PEBL-1 or a vector containing GFP alone ("Mock"). T-cells were stained with an anti-CD7 antibody (M-T701; BD Biosciences) conjugated to phycoerythrin. Intracellular expression of PEBL-1 was tested with a PE-conjugated anti-Myc antibody (9B11; Cell Signaling Technology) which binds to the sequence EQKLISEEDL (SEQ ID NO:40) incorporated in the ER-binding motif. Prior to antibody labelling, cells were permeabilized with 8E reagent (a permeabilization reagent developed in our laboratory).

Downregulation of CD7 Prevents T Cell Fratricide and does not Affect T Cell Function If the poor T-cell recovery was caused by fratricide mediated by CAR binding to CD7 expressed by the T cells, then it should improve by downregulating CD7 prior to CAR expression. To test this prediction, a rapid and practical method recently developed based on the expression of the anti-CD7 scFv linked to amino acid sequences containing the ER retention domains KDEL or KKMP [anti-CD7 Protein Expression Blocker (PEBL)] was applied. (FIG. 3E). These fasten the constructs to the ER/Golgi, preventing secretion or membrane expression of the targeted protein.[39, 40] 3 anti-CD7 PEBL constructs were tested and PEBL-1 was selected PEBL-1 for the next experiments (FIGS. 3E and 3F). CD7 surface expression was essentially abrogated in all T cells transduced with this construct while CD7 mRNA expression was retained (FIG. 3F, FIG. 10A and FIG. 10B); in 5 experiments, 98.1%±1.5% mock-transduced T cells were CD7+ versus 2.0%±1.7% for T cells transduced with the anti-CD7 PEBL (P<0.0001) (FIG. 3G). When the anti-CD7 CAR was expressed by electroporation in cells with downregulated CD7, it was clearly detectable by flow cytometry (FIG. 3H). By expressing the CAR in cells with CD7 knock-down, T cell viability markedly improved (FIG. 3I); in 6 paired experiments, viable cell recovery after CAR mRNA electroporation was consistently superior in T cells that had been previously transduced with the anti-CD7 PEBL (P=0.008).

Figures 4D, 4E, 4F:
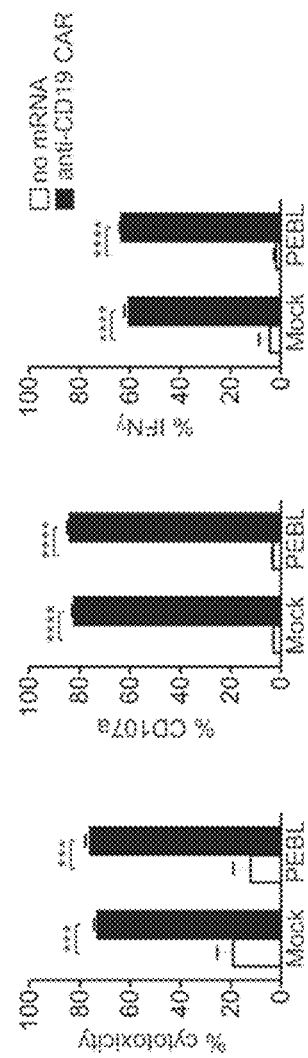

After anti-CD7 PEBL transduction, the proportion of CD4 and CD8 cells was similar to that of mock-transduced cells (FIG. 4A). Absence of CD7 expression on the surface membrane did not affect T-cell survival in culture (FIG. 4B). To further probe the functional capacity of T cells transduced with anti-CD7 PEBL, the cells were engineered to express the anti-CD19-CAR (FIG. CA). Their capacity to exert cytotoxicity, release cytotoxic granules, and secrete IFNγ in the presence of CD19+ ALL cells was tested. As shown in FIGS. 4D, 4E, and 4F, PEBL transduction and lack of surface CD7 did not altered CAR-mediated cell function.

Figure 5A:
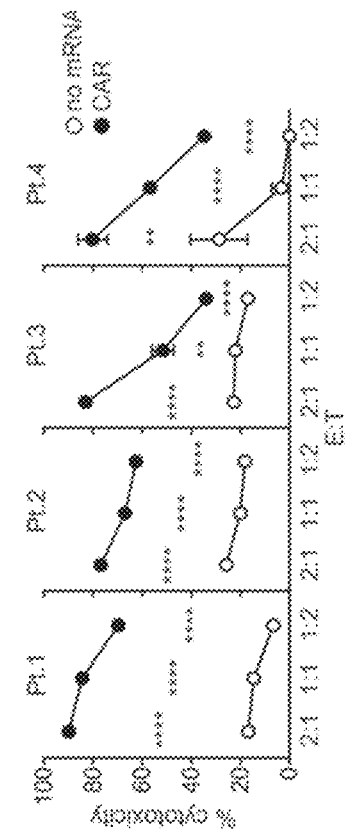
Figure 5C:
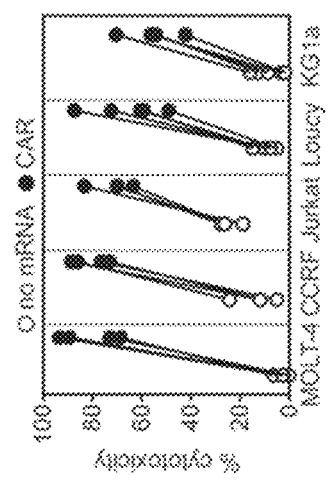
Figure 5B:
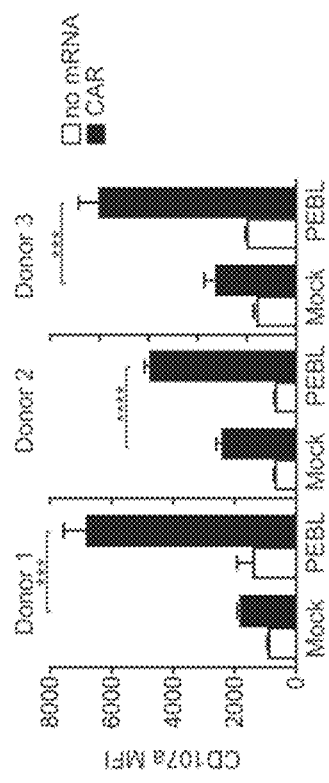

Anti-CD7-41BB-CD3ζ CAR Induces Powerful Cytotoxicity Against CD7+ Leukemic Cells CD7-negative T cells were prepared using anti-CD7 PEBL, and electroporated with the anti-CD7-41BB-CD3ζCAR mRNA. Their anti-leukemic capacity was assessed in co-cultures with the CD7+ leukemia cell lines MOLT-4, CCRF-CEM, Jurkat, Loucy or KG1a. As shown in FIG. 5A, cytotoxicity was dramatically increased by the CAR expression. PEBL-CAR T cells were also highly effective against primary T-ALL cells obtained from patients (FIG. 5B).

Figure 5D:
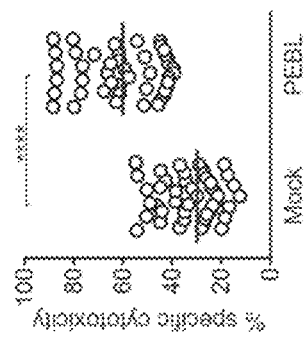
Figure 11A:
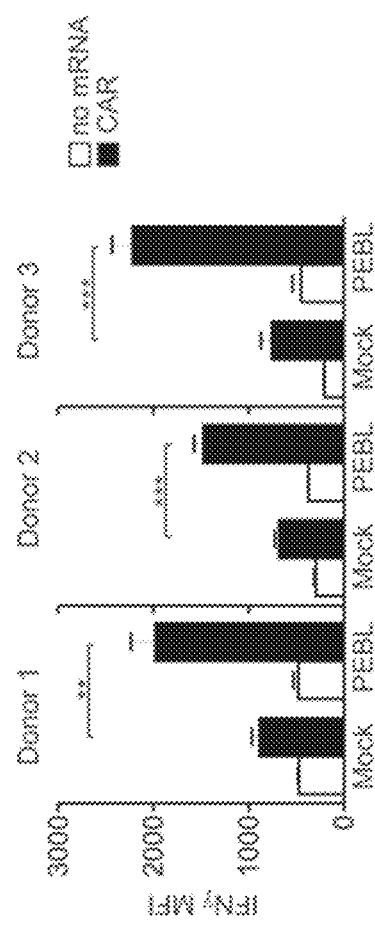
FIG. 11A and FIG. 11B show that anti-CD7 CAR signal elicited higher cytokine secretion in T cells with CD7 knock-down expression by anti-CD7 PEBL. T lymphocytes from 3 donors were transduced with anti-CD7 PEBL or GFP alone ("Mock") were electroporated with either anti-CD7-41BB-CD3ζ mRNA or no mRNA. Intracellular IFNγ (FIG. 11A) and TNFα (FIG. 11B) expression in T cells after 6 hours of co-culture with MOLT4 was measured. Bars represent mean (±SD) of triplicate MFI measurements. , P<0.01; *, P<0.001; ****, P<0.0001.
Figure 11B:
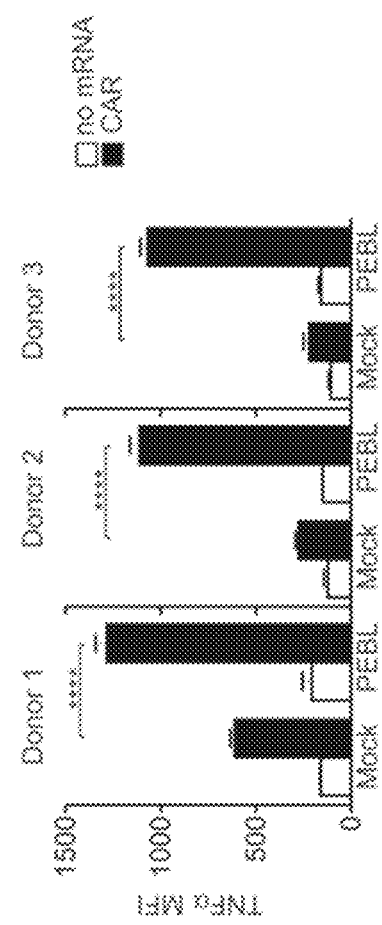
Figure 12:
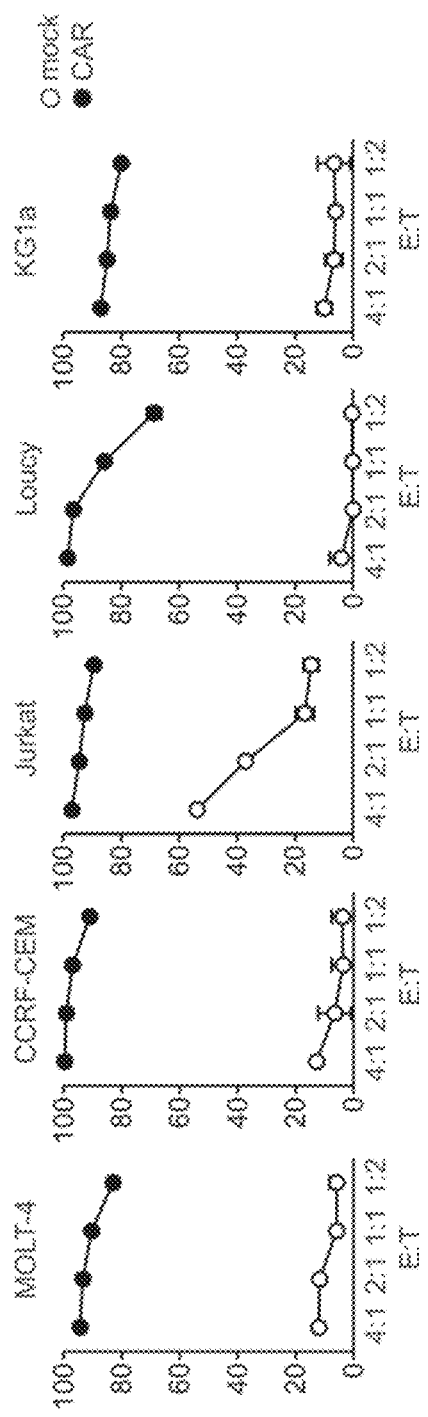
FIG. 12 shows that CD7-negative T-cells expressing anti-CD7-41BB-CD3ζCAR exerted anti-tumour cytotoxicity against CD7+ cell lines. Shown are results of 4-hour cytotoxicity assays performed with T cells transduced with anti-CD7 PEBL and then transduced with either CD7-41BB-CD3ζ or GFP only ("Mock"). Symbols represent mean (±SD) of triplicate experiments at the indicated E:T ratios. P<0.001 for all comparisons.
Figure 13B:
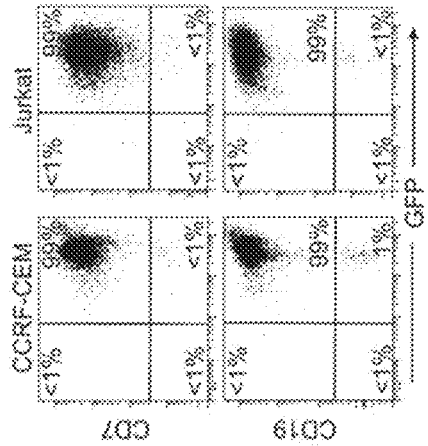
FIG. 13A-FIG. 13E provide functional comparisons of anti-CD7-41BB-CD3ζ and anti-CD19-41BB-CD3ζ CARs.
Figure 13A:
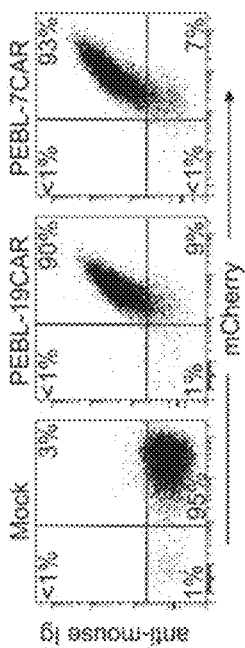
Figure 13C:
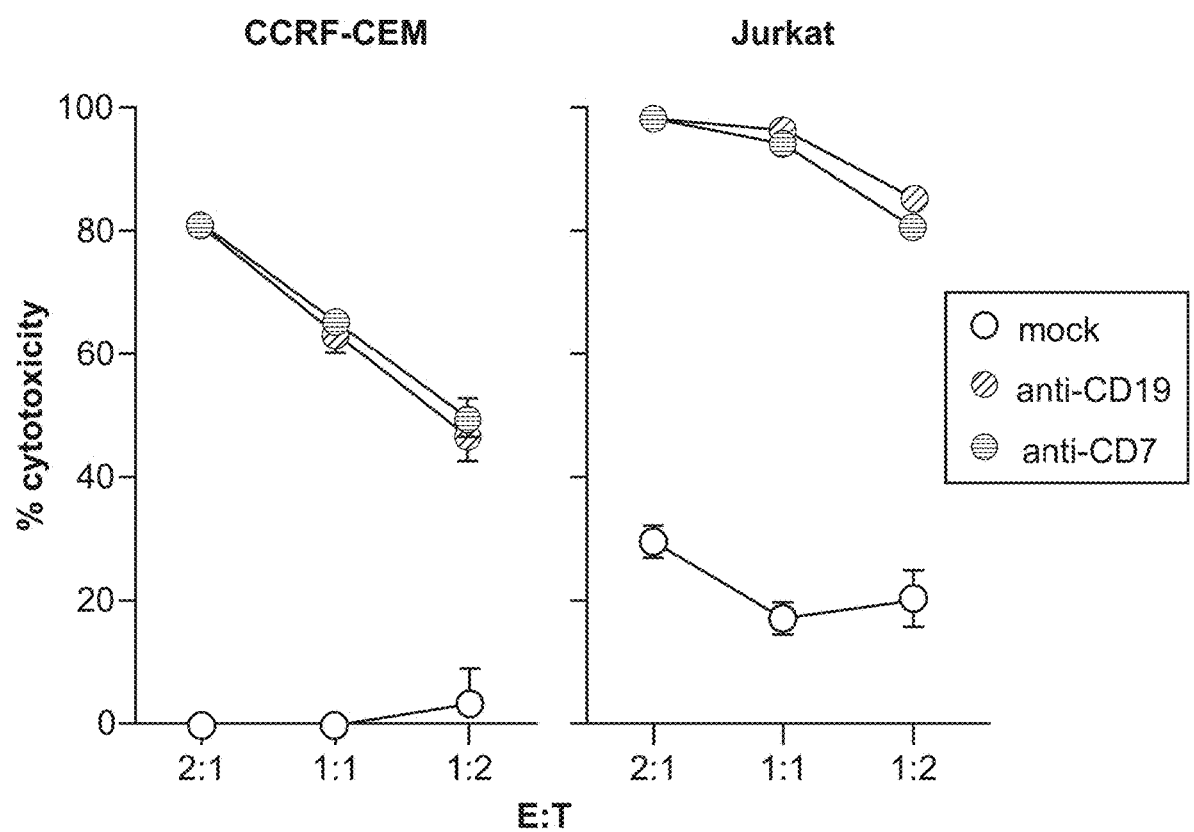
Figure 13D:
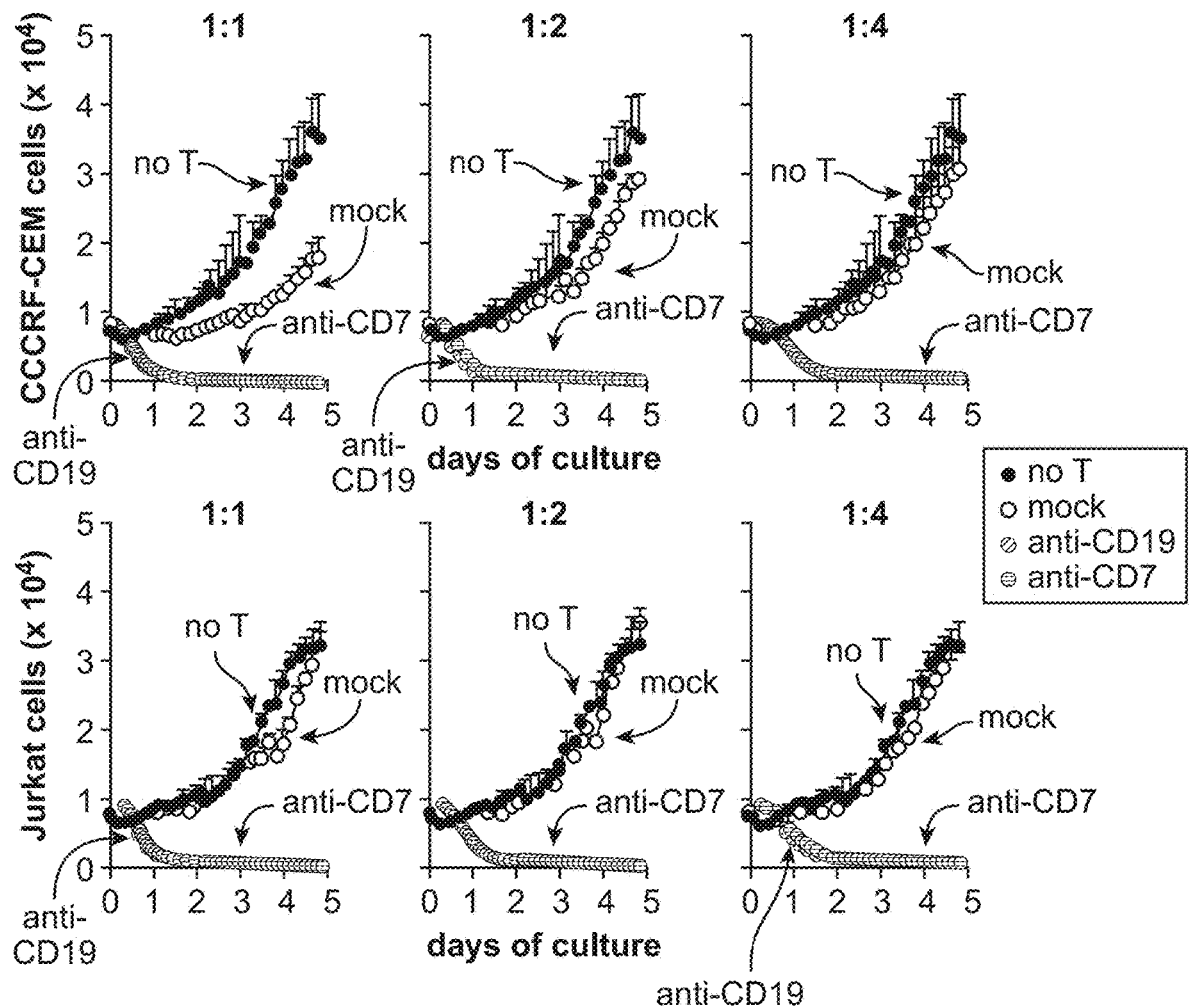
Figure 13E:
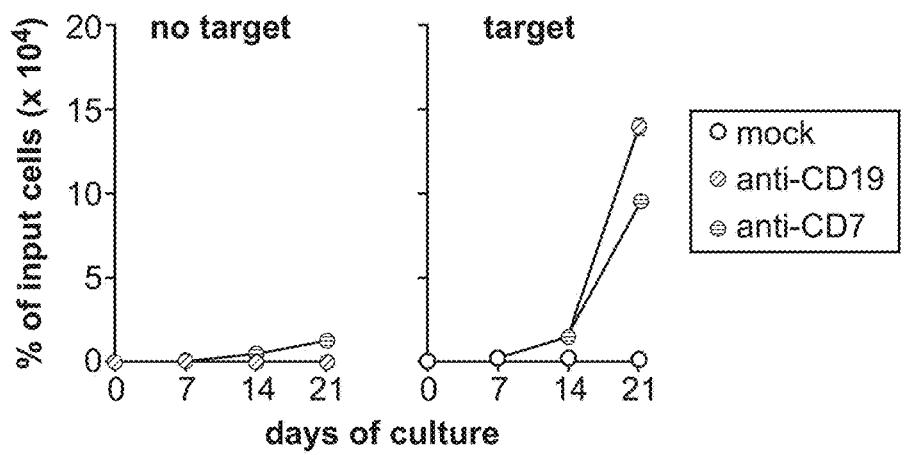

The cytotoxicity of PEBL-CAR T cells was compared to that of the residual T cells recovered after CAR electroporation in cells not transduced with PEBL. In 45 experiments with cells from 3 donors, cytotoxicity of the PEBL-CAR cells consistently surpassed that of non-PEBL T cells (FIG. 5C). The superior activity of the former cells was also observed when comparing the expressions of CD107a (FIG. 5D), IFNγ (FIG. 11A) and TNFα (FIG. 11B). Expression of PEBL and CAR by sequential retroviral transduction also produced powerful cytotoxicity against patient-derived T-ALL cells (FIG. 5E) and cell lines (FIG. 12). Proliferation of anti-CD7 PEBL-CAR-T cells in the presence of CD7+ target cells was much higher than that of CAR-T without CD7 downregulation by PEBL(P<0.01)(FIG. 5F). Finally, the cytotoxicity exerted by anti-CD7 PEBL-CAR T cells was compared to that of T cells expressing an anti-CD19-41BB-CD3ζ CAR[5] against the same target cells. To this end, CCRF-CEM and Jurkat cells were transduced with CD19, and also expressed either CAR in cells previously transduced with anti-CD7 PEBL (FIGS. 13A and 13B). Anti-CD7 and anti-CD19 CAR T cells had similar short- and long-term cytotoxicity (FIGS. 13C and 13D); long-term proliferative capacity in the presence of CD19+ CD7+ target cells was slightly lower for the anti-CD7 CAR-T cells (FIG. 13E), which might be explained by the lower expression of CD7 versus CD19 on target cells (FIG. 13B)

Anti-Leukemic Activity of Anti-CD7 PEBL-CAR T Cells in Murine Models of T-ALL

Figure 6B:
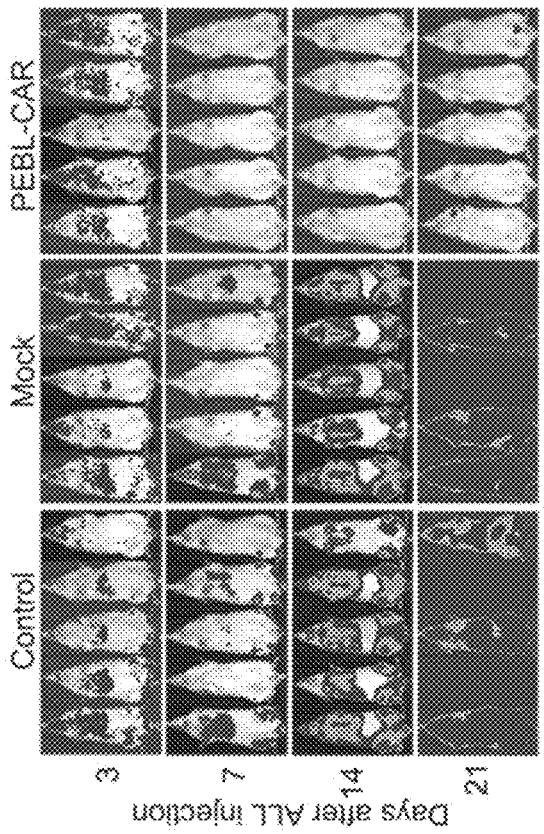
FIG. 6A-FIG. 6D show PEBL-transduced T-cells expressing anti-CD7-41BB-CD3ζ CAR exert antitumor activity in xenografts. NOD-SCID-IL2RG null mice were infused intravenously (i.v.) with $1\times10^6$ CCRF-CEM cells labelled with luciferase. $2\times10^7$ PEBL-CAR T cells were administered i.v. on day 7 (FIG. 6A), or on day 3 and day 7 (FIG. 6B) after leukemic cell infusion to 3 and 5 mice, respectively. The remaining mice received either mock-transduced T cells, or RPMI-1640 instead of cells ("Control"). All mice received 20,000 IU IL-2 once every two days intraperitoneally (i.p.). Shown is in vivo imaging of leukemia cell growth after D-luciferin i.p. injection. Ventral images of mice on day 3 in FIG. 6B are shown with enhanced sensitivity to demonstrate CCRF-CEM engraftment in all mice. The complete set of luminescence images is in FIG. 14.
Figure 6A:
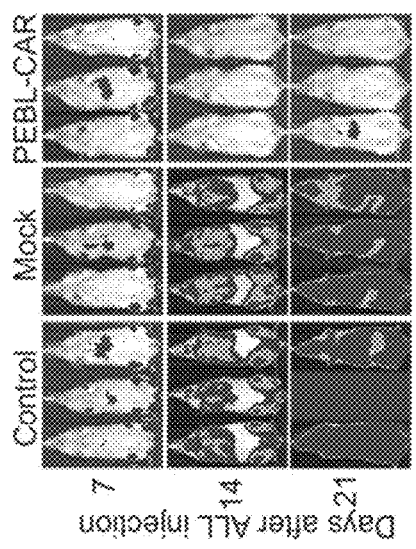
Figure 6C:
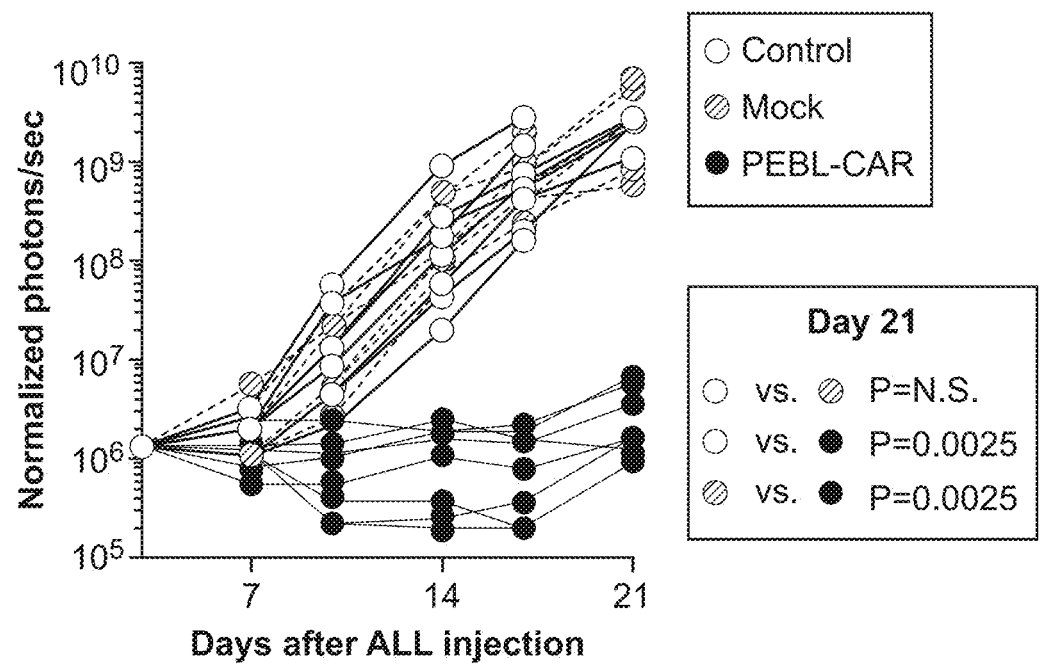
Figure 6D:
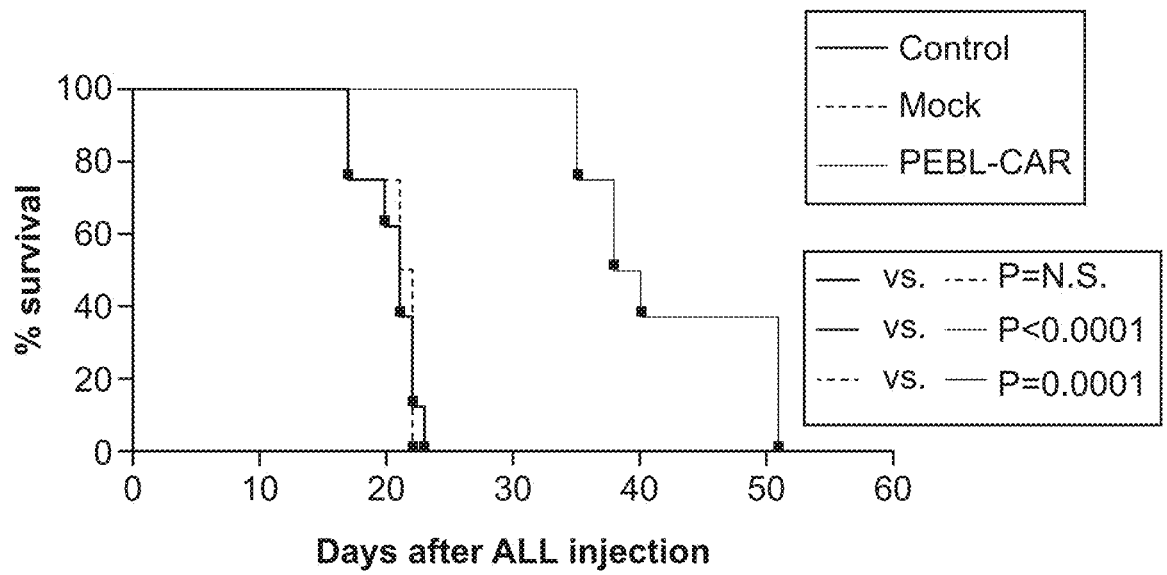
Figure 14A:
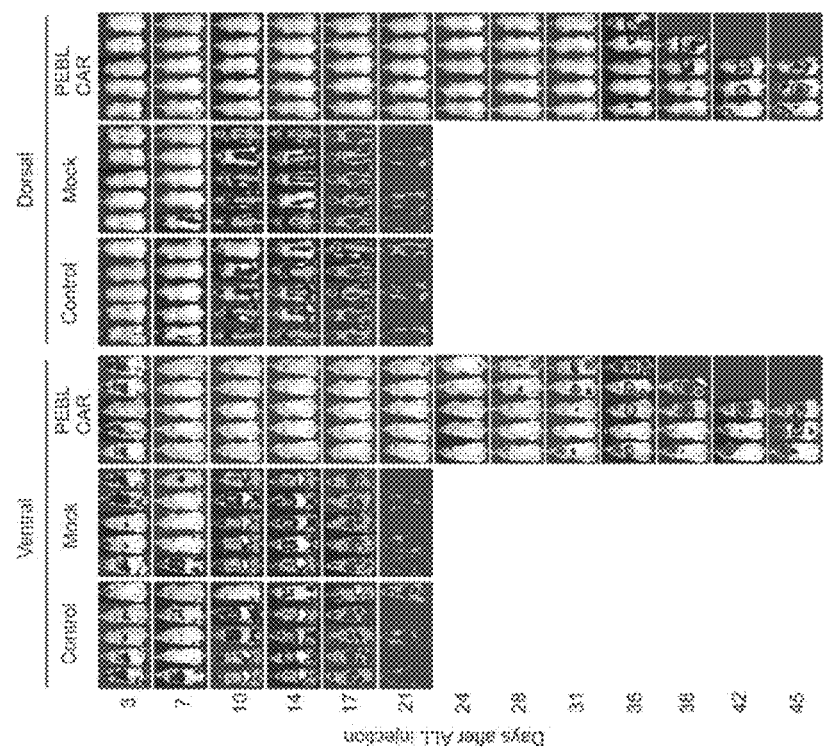
FIG. 14A-FIG. 14C illustrate PEBL-transduced T-cells expressing anti-CD7-41BB-CD3ζ CAR exerted antitumor activity in mouse models. NOD-SCID-IL2RGnull mice were infused intravenously with $1 \times 10^6$ CCRF-CEM cells labeled with luciferase. $2 \times 10^7$ PEBL-CAR T cells were administered intravenously on day 7 (FIG. 14A) or on day 3 and day 7 (FIG. 14B) after leukemic cell infusion to 3 and 5 mice, respectively. The remaining mice received either mock-transduced T cells, or RPMI-1640 instead of cells ("Control"). All mice received 20,000 IU IL-2 once every two days intraperitoneally (i.p.). In vivo imaging of leukemia cell growth was performed after D-luciferin i.p. injection. Ventral images of mice on day 3 in FIG. 14B are shown with enhanced sensitivity to demonstrate leukemia cell engraftment in all mice. Leukemia cell growth expressed as photons per second over time normalised to average of ventral plus dorsal signals in all mice before CAR-T cell infusion (FIG. 14C). Each symbol corresponds to bioluminescence measurements in each mouse.
Figure 14B:
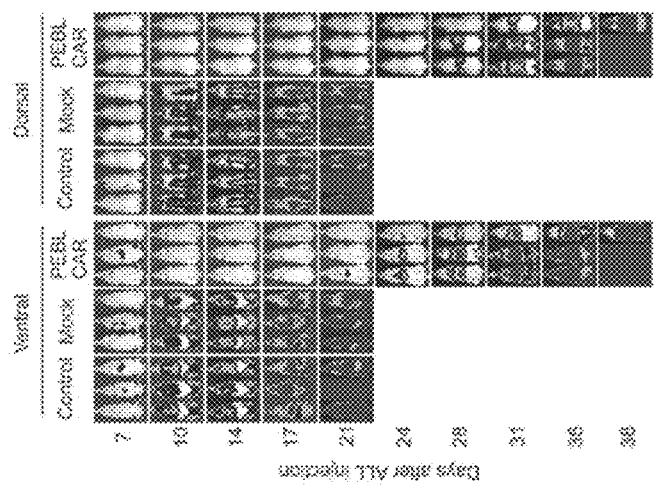
Figure 14C:
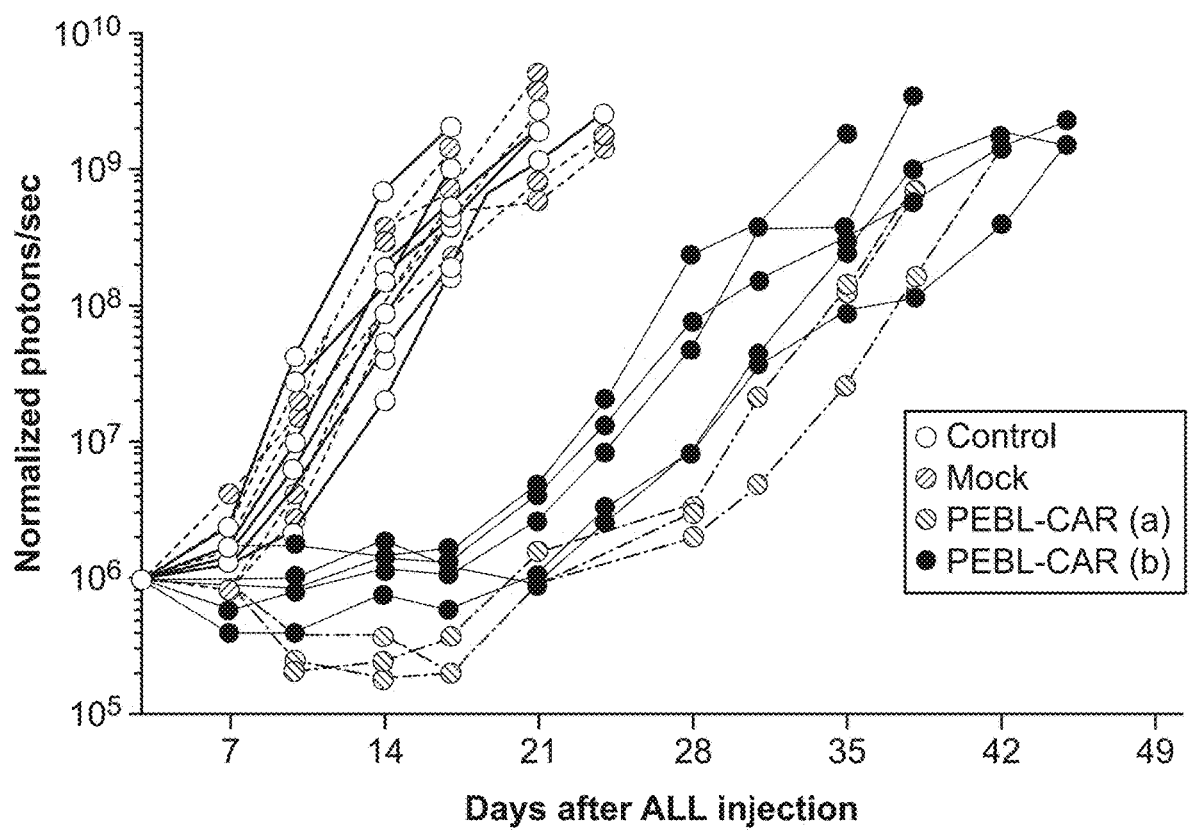

To further gauge the anti-tumor capacity of anti-CD7 PEBL-CAR T cells, NOD/scid IL2RGnull were engrafted with CCRF-CEM cells. T cells retrovirally transduced with anti-CD7 PEBL and anti-CD7 CAR produced considerable anti-leukemic effect, with a marked reduction in leukemia cell burden and a decrease in leukemia cell growth (FIGS. 6A-6C; FIGS. 14A and 14B). Three weeks after leukemic cell injection, median percent CCRF-CEM cells in peripheral blood by flow cytometry was 68% for control mice (n=5) and 67% for those who receive GFP-alone T cells (n=5), but they were undetectable in mice treated with anti-CD7 PEBL-CAR T cells (FIG. 15A). Relapse occurring after anti-CD7 PEBL-CAR T cell treatment was not due to CCRF-CEM cell subsets lacking CD7; leukemic cells continued to express high levels of CD7 and sensitivity to anti-CD7 CAR cytotoxicity remained high regardless of whether CCRF-CEM cells were derived from liver or spleen of relapsing mice or directly from the original cell culture (FIG. 15B).

Figure 7A:
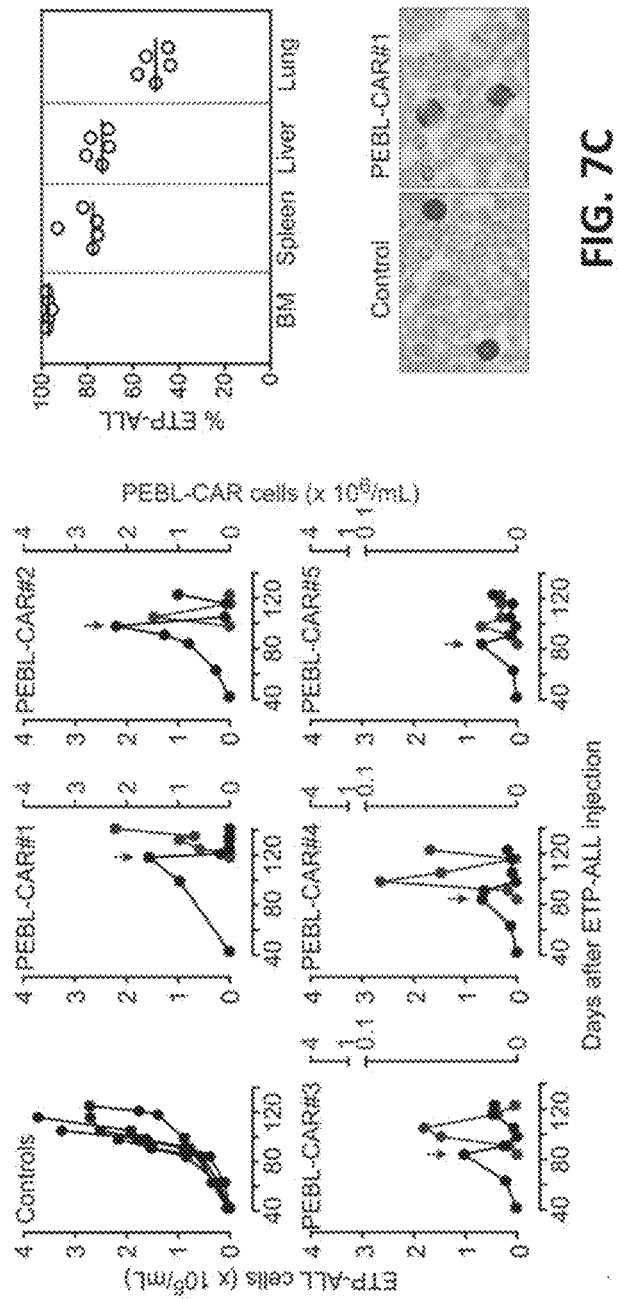
Figure 7B:
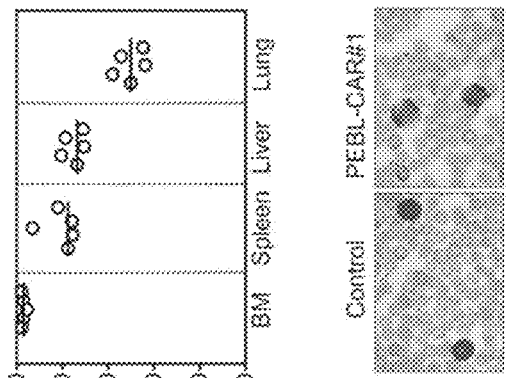
Figure 7C:
Figure 16:
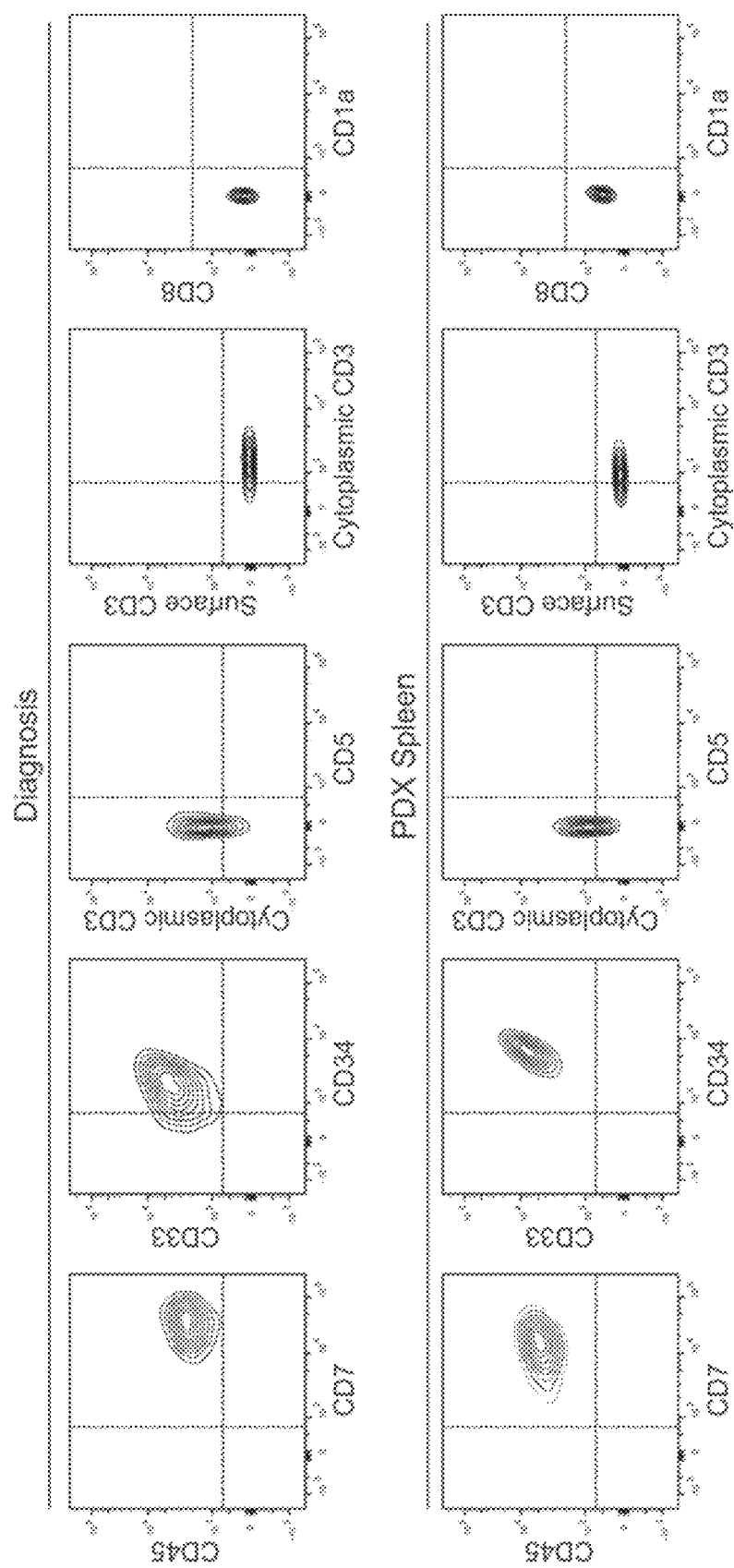
FIG. 16 provides immunophenotypic features of ETP-ALL at diagnosis and after propagation in NOD-SCID-IL2RGnull mice. Flow cytometric contour plots show the immunophenotype diagnostic bone marrow samples of the ETP-ALL used to develop the PDX model in this study and that of the ETP-ALL cells recovered from the spleen of one of the control mice shown in FIG. 7. The following antibodies were used: CD7-PE, CD45-APC-H7, CD34-PerCP, CD8-BV510, CDS-PE-Cy7, CD3-PerCP (for cytoplasmic staining), CD3-V450 (for surface staining), all from BD Biosciences; CD33-BV421 (Biolegend); CD1a-PE (Beckman Coulter). Quadrants were drawn based on staining with isotype-matched non-reactive antibodies conjugated to the same fluorochromes.

To test PEBL-CAR T cells against primary leukemic cells in vivo, a PDX model of ETP-ALL was used. The PDX model allows propagation of leukemic cells derived from a patient with ETP-ALL at diagnosis in NOD/scid IL2RGnull mice. Leukemic cells retained an immunophenotype matching that determined at diagnosis, with expression of CD7, CD34, CD33, and absence of surface CD3ζ, CD1a, CD8 and CD5 (FIG. 16); the cells were unable to survive and expand ex vivo, and needed to be injected in mice for propagation. All mice had ETP-ALL in peripheral blood at the time of CAR-T treatment (FIG. 7A). As shown in FIG. 7B, ETP-ALL cells represented the majority of leukocytes in bone marrow, spleen liver and lung. After administration of PEBL-CAR T cells ($2\times10^7$ in one mouse, $2\times10^6$ in the remaining 4), leukemic cell numbers in peripheral blood decrease dramatically, while PEBL-CAR-T cells became detectable in all mice (FIG. 7A). I n blood smears, smudge cells were prominent suggesting leukemia cell lysis (FIG. 7C). Leukemia progressed in all 5 control mice, which were euthanized after when ETP-ALL were ≥80% of peripheral blood mononucleated cells. The mouse treated with $2\times10^7$ PEBL-CAR-T cells, died of apparent graft-versus-host disease (GvHD) 23 days after PEBL-CAR-T cell infusion. No ETP-ALL could be detected in blood, bone marrow, liver, spleen, lung and brain, while PEBL-CAR T cells were detectable in all tissues (FIGS. 7D and 7E). The 4 mice treated with 2×10⁶ PEBL-CAR T cells are alive, 25 (n=1) to 39 (n=3) days post-infusion, with no signs of GvHD.

DISCUSSION

Durable remissions in patients with B-cell leukemia and lymphoma can be achieved with CAR-T cells but effective options are lacking for patients with T-cell malignancies. To bridge this gap, a CAR-T cell approach that could be rapidly translated into clinical intervention was developed and described herein. CD7, a widely expressed surface T-cell marker, which is highly stable even in T-ALL cells exposed to chemotherapy was targeted. A second-generation anti-CD7 CAR was designed. It was determined that suppression of CD7 surface expression in T cells was essential; without it, the CAR caused severe T-cell loss, and the full functional potential of CAR-T cells could not be achieved. Transduction of anti-CD7 PEBL resulted in virtually instantaneous abrogation of CD7 expression. Expression of anti-CD7 CAR in such cells produced powerful anti-leukemic activity in vitro, as well as in xenograft and PDX models of T-ALL. Thus, by using this strategy, large numbers of CAR-T cells were rapidly generated and were used to exert robust and specific cytotoxicity against T-cell malignancies, including one of the most aggressive forms, ETP-ALL.

The PEBL technology as described herein to downregulate endogenous CD7 is based on the use of a scFv directed against the targeted antigen coupled with an ER/Golgi-retention motif. In this way, any newly synthesized CD7 remains anchored in the ER and/or Golgi, and its surface expression is prevented. This method was remarkably effective in downregulating CD7 and suppressing CAR-mediated fratricide. Importantly, intracellular retention of CD7 did not alter T-cell function and allowed normal expansion, cytokine secretion, and cytotoxicity. This is consistent with results of studies with CD7-deficient mice which showed normal lymphocyte populations in lymphoid tissues.[41,42] An alternative approach to downregulate CD7 would be to apply gene editing methods, such as meganucleases, TALEN, or CRISPR/Cas9.[43] To this end, a recent study reported an anti-CD7 CAR which was expressed in T cells with CD7 gene deletion by CRISPR/Cas.[9,44] Besides differences in co-stimulatory molecules (the CAR described herein has 4-1BB instead of CD28) which may have clinical impact,[45,46] the high specificity and practical nature of the PEBL strategy make it particularly attractive for current clinical use. This method requires a simple transduction with the same viral vector carrying the CAR, either as two sequential transductions or a single transduction with a bicistronic vector carrying both constructs. It fits well with established clinical-grade cell manufacturing processes, and does not raise possible regulatory concerns associated with off-target activity.[47,48]

CD7 is a hallmark molecule for early T-cell differentiation; it is nearly universally expressed in T-ALL, and among normal cells, its expression is limited to T cells.[19,29-32] In a clinical study with an anti-CD7-ricin-A-chain immunotoxin in patients with T-cell lymphoma, the dose-limiting toxicity was vascular leak syndrome, a side-effect seen with other toxin-conjugates; no binding of anti-CD7 was found in endothelial cells of various tissues.[49] Nevertheless, transient expression of the CAR by mRNA electroporation might be considered in early studies assessing potential for acute toxicities of anti-CD7 PEBL-CAR T cells. A concern of anti-CD7 CAR therapy is the depletion of normal T cells by the infused cells, leading to immunodeficiency. One can envisage the initial application of this technology as a means to reduce MRD in patients with high-risk T-ALL, therefore maximizing the success of allogeneic hematopoietic stem cell transplantation.[50] In such instances, anti-CD7 CAR T cells would be eliminated by the transplant conditioning and the T-cell compartment reconstituted from donor stem cells. Outside the transplant setting, "suicide genes" could be activated once leukemia eradication has been achieved.[51] Ultimately, this may not be an issue, as the infused anti-CD7 T cells (which retain their endogenous CD3/TCR complex) might reconstitute a sufficiently wide T-cell repertoire. To this end, it should be noted that subsets of CD4 memory and CD8 effector T cells in human blood lymphocyte which do not express CD7 have been described,[52,53] and that T-ALL cells express CD7 at higher levels than normal T cells. Thus, CD7-dim subsets might help to repopulate the T-cell repertoire even after CD7-directed therapy.

The standard treatment of T-ALL mainly relies on intensive chemotherapy plus hematopoietic stem cell transplant for patients with high-risk disease. Results are far from satisfactory and have considerable morbidity and mortality.[54,55] The findings presented herein suggest the infusion of anti-CD7 PEBL-CAR T cells could significantly enhance, or perhaps replace, existing chemotherapy- and transplant-based strategies. Conceivably, CAR expression together with downregulation of the targeted antigen in T cells should also be applicable to other T cell markers, such as CD3ζ, CD2, and CD5 whose expression is prevalent in T-cell lymphoproliferative neoplasms. Because a fraction of high-risk acute myeloid leukemia cases express CD7,[19,30,56] testing the potential of anti-CD7 CAR-T cells for this leukemia subtype is also warranted.

REFERENCES

1. Eshhar Z, Waks T, Gross G, Schindler DG. Specific activation and targeting of cytotoxic lymphocytes through chimeric single chains consisting of antibody-binding domains and the gamma or zeta subunits of the immunoglobulin and T-cell receptors. Proc Natl Acad Sci USA 1993; 90(2): 720-724.
2. Geiger T L, Leitenberg D, Flavell R A. The TCR zeta-chain immunoreceptor tyrosine-based activation motifs are sufficient for the activation and differentiation of primary T lymphocytes. J Immunol 1999; 162(10): 5931-5939.
3. Brentjens R J, Latouche J B, Santos E, et al. Eradication of systemic B-cell tumors by genetically targeted human T lymphocytes co-stimulated by CD80 and interleukin-15. Nat Med 2003; 9(3):279-286.
4. Cooper L J, Topp M S, Serrano L M, et al. T-cell clones can be rendered specific for CD19: toward the selective augmentation of the graft-versus-B-lineage leukemia effect. Blood 2003; 101(4):1637-1644.
5. Imai C, Mihara K, Andreansky M, Nicholson I C, Pui C H, Campana D. Chimeric receptors with 4-1BB signaling capacity provoke potent cytotoxicity against acute lymphoblastic leukemia. Leukemia 2004; 18:676-684.
6. Rosenberg S A, Restifo N P. Adoptive cell transfer as personalized immunotherapy for human cancer. Science 2015; 348(6230):62-68.
7. Brentjens R J, Santos E, Nikhamin Y, et al. Genetically targeted T cells eradicate systemic acute lymphoblastic leukemia xenografts. Clin Cancer Res 2007; 13(18 Pt 1):5426-5435.
8. Haso W, Lee D W, Shah N N, et al. Anti-CD22-chimeric antigen receptors targeting B-cell precursor acute lymphoblastic leukemia. Blood 2013; 121(7):1165-1174.

9. Nadler L M, Anderson K C, Marti G, et al. B4, a human B lymphocyte-associated antigen expressed on normal, mitogen-activated, and malignant B lymphocytes. J Immunol 1983; 131(1):244-250.
10. Campana D, Janossy G, Bofill M, et al. Human B cell development. I. Phenotypic differences of B lymphocytes in the bone marrow and peripheral lymphoid tissue. J Immunol 1985; 134(3):1524-1530.
11. Porter D L, Levine B L, Kalos M, Bagg A, June C H. Chimeric antigen receptor-modified T cells in chronic lymphoid leukemia. N Engl J Med 2011; 365(8):725-733.
12. Grupp S A, Kalos M, Barrett D, et al. Chimeric antigen receptor-modified T cells for acute lymphoid leukemia. N Engl J Med 2013; 368(16):1509-1518.
13. Till B G, Jensen M C, Wang J, et al. CD20-specific adoptive immunotherapy for lymphoma using a chimeric antigen receptor with both CD28 and 4-1BB domains: pilot clinical trial results. Blood 2012; 119(17):3940-3950.
14. Kochenderfer J N, Dudley M E, Feldman S A, et al. B-cell depletion and remissions of malignancy along with cytokine-associated toxicity in a clinical trial of anti-CD19 chimeric-antigen-receptor-transduced T cells. Blood 2012; 119(12):2709-2720.
15. Davila M L, Riviere I, Wang X, et al. Efficacy and Toxicity Management of 19-28z CAR T Cell Therapy in B Cell Acute Lymphoblastic Leukemia. Sci Transl Med 2014; 6(224): 224ra225.
16. Maude S L, Frey N, Shaw P A, et al. Chimeric antigen receptor T cells for sustained remissions in leukemia. N Engl J Med 2014; 371(16):1507-1517.
17. Lee D W, Kochenderfer J N, Stetler-Stevenson M, et al. T cells expressing CD19 chimeric antigen receptors for acute lymphoblastic leukaemia in children and young adults: a phase 1 dose-escalation trial. Lancet 2015; 385(9967):517-528.
18. Turtle C J, Hanafi L A, Berger C, et al. CD19 CAR-T cells of defined CD4+:CD8+ composition in adult B cell ALL patients. J Clin Invest 2016; 126(6):2123-2138.
19. Coustan-Smith E, Mullighan C G, Onciu M, et al. Early T-cell precursor leukaemia: a subtype of very high-risk acute lymphoblastic leukaemia. Lancet Oncol 2009; 10(2): 147-156.
20. Zhang J, Ding L, Holmfeldt L, et al. The genetic basis of early T-cell precursor acute lymphoblastic leukaemia. Nature 2012; 481(7380):157-163.
21. Inukai T, Kiyokawa N, Campana D, et al. Clinical significance of early T-cell precursor acute lymphoblastic leukaemia: results of the Tokyo Children's Cancer Study Group Study L99-15. Br J Haematol 2012; 156(3):358-365.
22. Neumann M, Heesch S, Gokbuget N, et al. Clinical and molecular characterization of early T-cell precursor leukemia: a high-risk subgroup in adult T-ALL with a high frequency of FLT3 mutations. Blood Cancer J 2012; 2(1):e55.
23. Jain N, Lamb A V, O'Brien S, et al. Early T-cell precursor acute lymphoblastic leukemia/lymphoma (ETP-ALL/LBL) in adolescents and adults: a high-risk subtype. Blood 2016; 127(15): 1863-1869.
24. Marks D I, Rowntree C. Management of adults with T-cell lymphoblastic leukemia. Blood 2017; 129(9):1134-1142.
25. Campana D, Pui C H. Minimal residual disease-guided therapy in childhood acute lymphoblastic leukemia. Blood 2017; 129(14):1913-1918.
26. Coustan-Smith E, Sancho J, Hancock M L, et al. Use of peripheral blood instead of bone marrow to monitor residual disease in children with acute lymphoblastic leukemia. Blood 2002; 100:2399-2402.
27. Mihara K, Yanagihara K, Takigahira M, et al. Activated T-cell-mediated immunotherapy with a chimeric receptor against CD38 in B-cell non-Hodgkin lymphoma. J Immunother 2009; 32(7):737-743.
28. Mamonkin M, Rouce R H, Tashiro H, Brenner M K. A T-cell-directed chimeric antigen receptor for the selective treatment of T-cell malignancies. Blood 2015; 126(8): 983-992.
29. Haynes B F, Eisenbarth G S, Fauci A S. Human lymphocyte antigens: production of a monoclonal antibody that defines functional thymus-derived lymphocyte subsets. Proc Natl Acad Sci USA 1979; 76(11):5829-5833.
30. Vodinelich L, Tax W, Bai Y, Pegram S, Capel P, Greaves M F. A monoclonal antibody (WT1) for detecting leukemias of T-cell precursors (T-ALL). Blood 1983; 62(5): 1108-1113.
31. Janossy G, Coustan-Smith E, Campana D. The reliability of cytoplasmic CD3ζ and CD22 antigen expression in the immunodiagnosis of acute leukemia: a study of 500 cases. Leukemia 1989; 3(3):170-181.
32. Yeoh E J, Ross M E, Shurtleff S A, et al. Classification, subtype discovery, and prediction of outcome in pediatric acute lymphoblastic leukemia by gene expression profiling. Cancer Cell 2002; 1:133-143.
33. Manabe A, Coustan-Smith E, Kumagai M, et al. Interleukin-4 induces programmed cell death (apoptosis) in cases of high-risk acute lymphoblastic leukemia. Blood 1994; 83(7): 1731-1737.
34. Peipp M, Kupers H, Saul D, et al. A recombinant CD7-specific single-chain immunotoxin is a potent inducer of apoptosis in acute leukemic T cells. Cancer Res 2002; 62(10):2848-2855.
35. Kudo K, Imai C, Lorenzini P, et al. T lymphocytes expressing a CD16 signaling receptor exert antibody-dependent cancer cell killing. Cancer Res 2014; 74(1): 93-103.
36. Shimasaki N, Fujisaki H, Cho D, et al. A clinically adaptable method to enhance the cytotoxicity of natural killer cells against B-cell malignancies. Cytotherapy. 2012; 14(7):830-40.
37. Shimasaki N, Campana D. Natural killer cell reprogramming with chimeric immune receptors. Methods Mol Biol 2013; 969:203-220.
38. Chang Y H, Connolly J, Shimasaki N, Mimura K, Kono K, Campana D. A Chimeric Receptor with NKG2D Specificity Enhances Natural Killer Cell Activation and Killing of Tumor Cells. Cancer Res 2013; 73(6):1777-1786.
39. Munro S, Pelham H R. A C-terminal signal prevents secretion of luminal E R proteins. Cell 1987; 48(5):899-907.
40. Jackson M R, Nilsson T, Peterson P A. Identification of a consensus motif for retention of transmembrane proteins in the endoplasmic reticulum. EMBO J 1990; 9(10):3153-3162.
41. Bonilla F A, Kokron C M, Swinton P, Geha R S. Targeted gene disruption of murine CD7. Int Immunol 1997; 9(12): 1875-1883.
42. Lee D M, Staats H F, Sundy J S, et al. Immunologic characterization of CD7-deficient mice. J Immunol 1998; 160(12):5749-5756.

43. Boettcher M, McManus M T. Choosing the right tool for the job: RNAi, TALEN, or CRISPR. Mol Cell 2015; 58(4):575-585.
44. Gomes-Silva D, Srinivasan M, Sharma S, et al. CD7-edited T cells expressing a CD7-specific CAR for the therapy of T-cell malignancies. Blood. 2017 May 24. pii: blood-2017-01-761320.
45. Campana D, Schwarz H, Imai C. 4-1BB chimeric antigen receptors. Cancer J 2014; 20(2):134-140.
46. Zhao Z, Condomines M, van der Stegen S J, et al. Structural Design of Engineered Costimulation Determines Tumor Rejection Kinetics and Persistence of CAR T Cells. Cancer Cell 2015; 28(4):415-428.
47. Tsai S Q, Joung J K. Defining and improving the genome-wide specificities of CRISPR-Cas9 nucleases. Nat Rev Genet 2016; 17(5):300-312.
48. Cameron P, Fuller C K, Donohoue P D, et al. Mapping the genomic landscape of CRISPR-Cas9 cleavage. Nat Methods 2017; 14(6):600-606.
49. Frankel A E, Laver J H, Willingham M C, Burns L J, Kersey J H, Vallera D A. Therapy of patients with T-cell lymphomas and leukemias using an anti-CD7 monoclonal antibody-ricin A chain immunotoxin. Leuk Lymphoma 1997; 26(3-4):287-298.
50. Leung W, Pui C H, Coustan-Smith E, et al. Detectable minimal residual disease before hematopoietic cell transplantation is prognostic but does not preclude cure for children with very-high-risk leukemia. Blood 2012; 120(2):468-72.
51. Straathof K C, Spencer D M, Sutton R E, Rooney C M. Suicide genes as safety switches in T lymphocytes. Cytotherapy 2003; 5(3):227-230.
52. Reinhold U, Abken H, Kukel S, et al. CD7- T cells represent a subset of normal human blood lymphocytes. J Immunol 1993; 150(5):2081-2089.
53. Aandahl E M, Sandberg J K, Beckerman K P, Tasken K, Moretto W J, Nixon D F. CD7 is a differentiation marker that identifies multiple CD8 T cell effector subsets. J Immunol 2003; 170(5):2349-2355.
54. Raetz E A, Teachey D T. T-cell acute lymphoblastic leukemia. Hematology Am Soc Hematol Educ Program 2016; 2016(1):580-588.
55. Jabbour E, O'Brien S, Konopleva M, Kantarjian H. New insights into the pathophysiology and therapy of adult acute lymphoblastic leukemia. Cancer 2015; 121(15): 2517-2528.
56. Kita K, Miwa H, Nakase K, et al. Clinical importance of CD7 expression in acute myelocytic leukemia. The Japan Cooperative Group of Leukemia/Lymphoma. Blood 1993; 81(9):2399-2405.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An expression vector comprising:
   a) a first nucleic acid comprising a nucleotide sequence encoding a target-CD7 binding molecule linked to an endoplasmic reticulum (ER) localizing domain, wherein said target-CD7 binding molecule comprises a first scFv antibody that binds to an endogenous CD7 in an engineered immune cell, and wherein the ER localizing domain comprises an amino acid sequence selected from the group consisting of SEQ ID NO:8, SEQ ID NO:9, and SEQ ID NO: 13, and wherein the first nucleic acid comprises a nucleotide sequence encoding a CD8 alpha signal peptide; and
   b) a second nucleic acid comprises a nucleotide sequence encoding a CD7 CAR, wherein said CD7 CAR comprises a second scFv antibody that binds to CD7, a transmembrane domain, and an intracellular signaling domain;

wherein the first scFv antibody and the second scFv antibody comprise:
   (i) a heavy chain variable domain having at least 95% sequence identity to the amino acid sequence of SEQ ID NO: 1, comprising:
      a heavy chain (HC) complementarity determining region (CDR) 1 comprising amino acids 31-35 of SEQ ID NO: 1,
      a HC CDR2 comprising amino acids 50-65 of SEQ ID NO: 1, and
      a HC CDR3 comprising amino acids 98-106 of SEQ ID NO: 1, and
      a light chain variable domain having at least 95% sequence identity to the amino acid sequence of SEQ ID NO: 2, comprising:
      a light chain (LC) CDR1 comprising amino acids 28-38 of SEQ ID NO: 2,
      a LC CDR2 comprising amino acids 54-60 of SEQ ID NO: 2, and
      a LC CDR3 comprising amino acids 93-101 of SEQ ID NO: 2,
   (ii) a heavy chain variable domain having at least 95% sequence identity to the amino acid sequence of SEQ ID NO: 14, comprising:
      a HC CDR1 comprising amino acids 31-35 of SEQ ID NO: 14,
      a HC CDR2 comprising amino acids 50-66 of SEQ ID NO: 14, and
      a HC CDR3 comprising amino acids 99-112 of SEQ ID NO: 14, and
      a light chain variable domain having at least 95% sequence identity to the amino acid sequence SEQ ID NO: 15, comprising:
      a LC CDR1 comprising amino acids 24-34 of SEQ ID NO: 15,
      a LC CDR2 comprising amino acids 50-56 of SEQ ID NO: 15, and
      a LC CDR3 comprising amino acids 89-97 of SEQ ID NO: 15, or
   (iii) a heavy chain variable domain having at least 95% sequence identity to the amino acid sequence of SEQ ID NO: 16, comprising:
      a HC CDR1 comprising amino acids 31-35 of SEQ ID NO: 16,
      a HC CDR2 comprising amino acids 50-66 of SEQ ID NO: 16, and
      a HC CDR3 comprising amino acids 99-109 of SEQ ID NO: 16, and
      a light chain variable domain having at least 95% sequence identity to the amino acid sequence of SEQ ID NO: 17, comprising:
      a LC CDR1 comprising amino acids 24-38 of SEQ ID NO: 17,
      a LC CDR2 comprising amino acids 54-60 of SEQ ID NO: 17, and
      a LC CDR3 comprising amino acids 93-101 of SEQ ID NO: 17,
      wherein the binding of endogenous CD7 to the CD7 binding domain reduces surface expression of the endogenous CD7 in the engineered immune cell, thereby increasing the effectiveness of the engineered immune cell against CD7 positive cancer cells.

2. The expression vector of claim 1, wherein the amino acid sequence of the first scFv antibody and the amino acid sequence of the second scFv antibody are identical.

3. The expression vector of claim 1, wherein the first scFv antibody comprises:
   a) a heavy chain variable domain comprising the amino acid sequence of SEQ ID NO:1 and a light chain variable domain comprising the amino acid sequence of SEQ ID NO:2;
   b) a heavy chain variable domain comprising the amino acid sequence of SEQ ID NO: 14 and a light chain variable domain comprising the amino acid sequence of SEQ ID NO: 15; or
   c) a heavy chain variable domain comprising the amino acid sequence of SEQ ID NO: 16 and a light chain variable domain comprising the amino acid sequence of SEQ ID NO: 17.

4. The expression vector of claim 1, wherein the second scFv antibody comprises:
   a) a heavy chain variable domain comprising the amino acid sequence of SEQ ID NO:1 and a light chain variable domain comprising the amino acid sequence of SEQ ID NO:2;

b) a heavy chain variable domain comprising the amino acid sequence of SEQ ID NO: 14 and a light chain variable domain comprising the amino acid sequence of SEQ ID NO: 15; or c) a heavy chain variable domain comprising the amino acid sequence of SEQ ID NO: 16 and a light chain variable domain comprising the amino acid sequence of SEQ ID NO: 17.

5. The expression vector of claim 1, wherein the first scFv antibody and the second scFv antibody both comprise a heavy chain variable domain comprising the amino acid sequence of SEQ ID NO: 1 and a light chain variable domain comprising the amino acid sequence of SEQ ID NO: 2.

6. The expression vector of claim 1, wherein the CD7 CAR comprises a 4-1BB intracellular signaling domain, and a CD3ζ intracellular signaling domain.

7. An engineered immune cell comprising the expression vector of claim 1.

8. The engineered immune cell of claim 7, wherein the engineered immune cell is a T cell.

9. A method for treating CD7 positive cancer in a patient in need thereof, comprising administering a therapeutically effective amount of an engineered immune cell, wherein said engineered immune cell comprises the expression vector of claim 1.

10. The method of claim 9, wherein the CD7 positive cancer is a T cell malignancy.

11. The method of claim 9, wherein the engineered immune cell is a T cell.

12. The method of claim 11, wherein the amino acid sequence of the first scFv antibody and the amino acid sequence of the second scFv antibody are identical.

13. The method of claim 9, wherein each of first and second scFvs comprises:

a) a heavy chain variable domain comprising the amino acid of SEQ ID NO: 1 and a light chain variable domain comprising the amino acid of SEQ ID NO:2;

b) a heavy chain variable domain comprising the amino acid of SEQ ID NO: 14 and a light chain variable domain comprising the amino acid of SEQ ID NO:15; or c) a heavy chain variable domain comprising the amino acid of SEQ ID NO: 16 and a light chain variable domain comprising the amino acid of SEQ ID NO:17.

14. The expression vector of claim 1, wherein the second nucleic acid further comprises a nucleotide sequence encoding a CD8 alpha signal peptide.

15. The expression vector of claim 1, wherein the CD8 alpha signal peptide comprises the amino acid sequence of SEQ ID NO: 7.

* * * * *